United States Patent [19]

Dupont et al.

[11] Patent Number: 6,028,118
[45] Date of Patent: *Feb. 22, 2000

[54] METHODS OF USING EXTRACTS OF SHARK CARTILAGE

[75] Inventors: Eric Dupont, St. Nicholas; Paul Brazeau, Montreal; Christina Juneau, Ste. Foy, all of Canada; Daniel H. Maes, Huntington; Kenneth Marenus, Dix Hills, both of N.Y.

[73] Assignee: Les Laboratoires Aeterna Inc., Quebec, Canada

[*] Notice: This patent is subject to a terminal disclaimer.

[21] Appl. No.: 08/693,535

[22] Filed: Aug. 8, 1996

[51] Int. Cl.$^7$ .................................................. A61K 35/12
[52] U.S. Cl. .................... 514/863; 514/859; 514/828; 424/520
[58] Field of Search ................... 514/863, 859, 514/828; 424/520

[56] References Cited

U.S. PATENT DOCUMENTS

| | | |
|---|---|---|
| 3,478,146 | 11/1969 | Balassa . |
| 4,042,457 | 8/1977 | Kuettner et al. . |
| 4,243,582 | 1/1981 | Spilburg et al. . |
| 4,350,682 | 9/1982 | Balassa ..................................... 424/64 |
| 4,356,261 | 10/1982 | Kuettner . |
| 4,473,551 | 9/1984 | Schinitsky ................................ 424/95 |
| 4,656,137 | 4/1987 | Balassa . |
| 4,746,729 | 5/1988 | Kuettner et al. . |
| 4,749,522 | 6/1988 | Kamarei . |
| 4,822,607 | 4/1989 | Balassa . |
| 5,075,112 | 12/1991 | Lane . |

FOREIGN PATENT DOCUMENTS

| | | | |
|---|---|---|---|
| WO 94/12510 | 6/1994 | WIPO ............................ C07G 17/00 |
| WO 95/03036 | 2/1995 | WIPO ............................. A61K 9/16 |
| WO95/32722 | 12/1995 | WIPO ............................ A61K 35/60 |

OTHER PUBLICATIONS

Arnett, F.C. et al. (1988). Arthritis & Rheumatism, 31: 315–324.

Chabot–Fletcher, M. et al. (1994). "Interleukin–8 Production is Regulated by Protein Kinase C in Human Keratinocytes". *The Journal of Investigative Dermatology* 103(4): 509–515.

Elias, P.M. (1993). *J. Invest. Dermatol.* 80: 044s–049s.

Folkman, J. and M. Klagsbrun (1987). "Angiogenic Factors". *Science.* 235: 442–446.

Grove, G.L. (1994) "Age–Related Differences in Healing of Superficial Skin wounds in Humans" In *The effects of aging in oral mucosa and skin*. Ed. Squier & Hill CRC Press, pp. 121–127.

Langer, R et al. (1976). "Isolation of a Cartilage Factor That Inhibits Tumor Neovascularisation". *Science.* 193: 70–72.

Lee, A. and R. Langer (1983). "Shark Cartilage Contains Inhibitors of Tumor Angiogenesis". *Science.* 221: 1185–1187.

Luer. C.A. (1986). "Inhibitors of Angiogenesis from Shark Cartilage". *Fed. Proc.* 45(4): 949, Abstract 4624.

Matsui, M.S. et al. (1992). "Protein Kinase C in Normal Human Epidermal Keratinocytes During Proliferation and Calcium–Induced Differenciation". *J. Invest. Dermatol.* 99: 565–571.

Medina, D. and K.B. DeOME (1969). "Response of Hyperplastic Alveolar Nodule Outgrowth–Line D1 to Mammary Tumor Virus, Nodule–Inducing Virus, and Prolonged . . . " *J. Natl. Cancer Inst.* 42: 303–310.

Medina, D. (1976). Mammary Tumorigenesis in Chemical Carcinogen–Treated Mice, VI. Tumor–Producing Capabilities of Mammary Dysplasias in BALB/cCrgl Mice. *J. Natl. Cancer Inst.* 57: 1185–1189.

Moses, M.A. and R. Langer (1991). "Inhibitors of Angiogenesis". *Biotechnology* 9:630–634.

Nickoloff, B.J. et al. (1994). "Aberrant Production of Interleukin–8 and Thrombospondin–1 Psoriastic Keratinocytes Mediates Angiogenesis". *Am. J.Pathology* 144(4): 820–828.

Oikawa, T. et al. (1990) "A novel angiogenic inhibitor derived from Japanese shark cartilage (I). Extraction and estimation of inhibitory activities toward tumor and embyronic angiogenesis". *Cancer Letters* 51: 181–186.

Oresago, C. et al. (1987). "Eye Area Problems Puffiness, Bags, Dark Circles and Crowsfeet" *Cosmetics and Toiletries* 102: 29–34.

(List continued on next page.)

*Primary Examiner*—Frank C. Eisenschenk
*Assistant Examiner*—Brett Nelson
*Attorney, Agent, or Firm*—Rick Matos; Akin, Gump, Strauss, Hauer & Feld, L.L.P.

[57] ABSTRACT

The present invention relates to cartilage extracts and to a method of producing the same. Shark cartilage extracts having anti-angiogenic, anti-tumoral, anti-inflammatory and anti-collagenolytic activities have been obtained by an improved process. The process comprises the steps of obtaining a homogenate of cartilage in an aqueous solution, this homogenate being separated in a solid fraction (SOLID EXTRACT) and a liquid fraction which was further fractionated to obtain a LIQUID EXTRACT having molecules of a molecular weight comprised between 0 to 500 kDa. The composition of the liquid extract has then been investigated by different ways. Further fractionation of this extract led to the preliminary characterization of some of its active components. Due to the multiplicity of biological activities of the total liquid extract, it can be used for treating numerous diseases or conditions such as those having components selected from the group consisting of tumor proliferation, angiogenesis, inflammation and collagenolysis. Several cosmetic applications based on the capacity of the liquid extract to improve skin barrier function are also under the scope of this invention. These extracts have no offensive effect on normal body functions. Therefore, these shark cartilage extracts have a very promising therapeutic value. The process for the obtention of cartilage extracts is simple and efficient. The unexpectedly valuable products obtained by this process are therefore an indication of a new and nonobvious process.

12 Claims, 26 Drawing Sheets

OTHER PUBLICATIONS

Pinnagoda, J. et al. (1990). Guidelines for transepidermal water loss (TEWL) measurement *Contact Dermatitis* 22: 164–178.

Ritchie, D.M. et al. (1968). "Clinical Studies with an articular index for the assessment of joint tenderness in patients with rheumatoid arthritis". *Quarterly J. Med. New Series XXXVII,* 147: 393–406.

Suzuki, F. et al. (1984). "Cartilage–derived Antitumor Factor (CATF): A High Molecular Weight Fraction in Cartilage Extract Inhibits Solid Tumor Growth". *J. of Bone and Mineral Metabolism* 2(3): 3–7.

Weingarten, H. et al. (1985). "Synthetic Substrate of Vertebrate Collagenase". *Biochemistry* 24: 6730–6734.

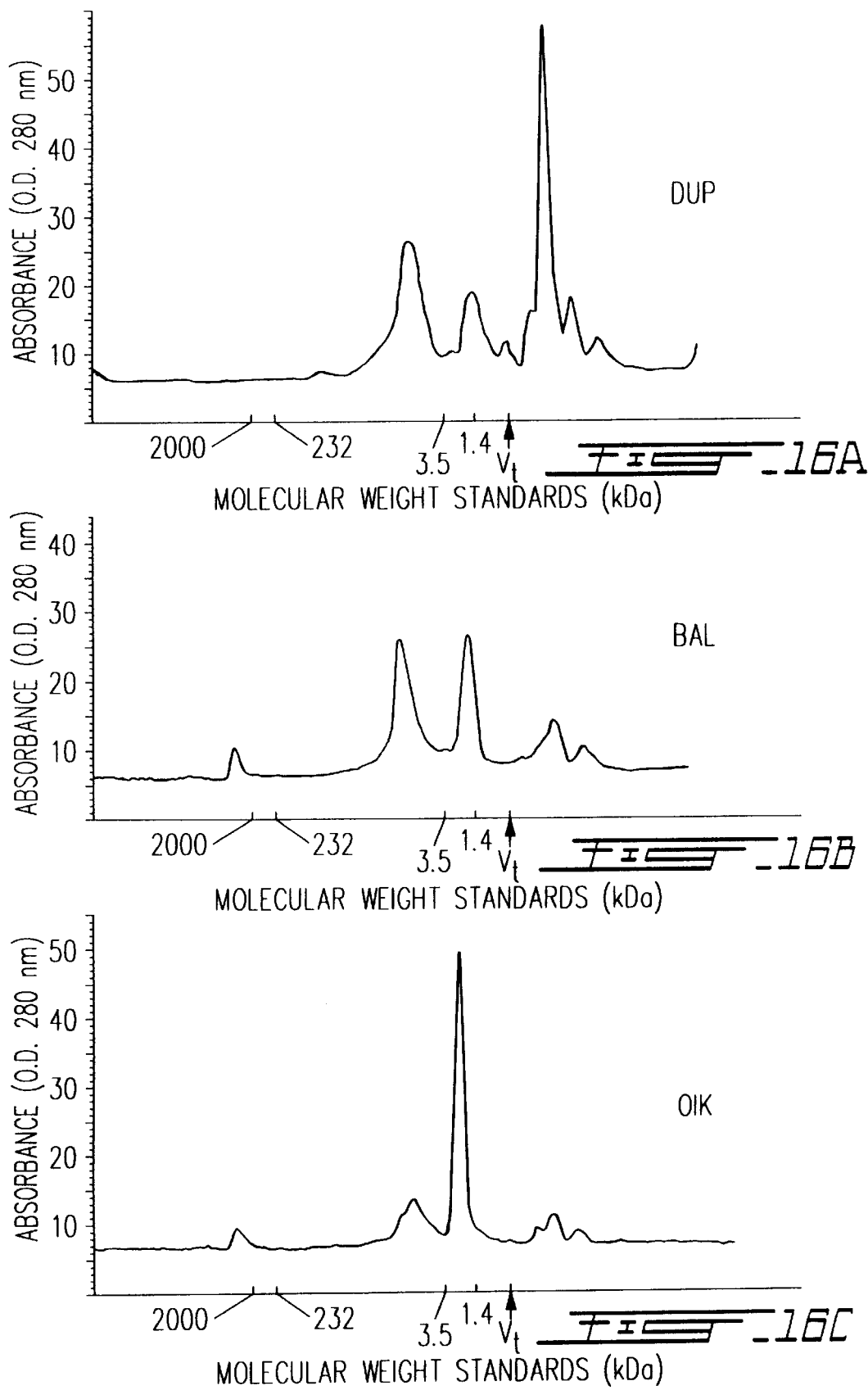

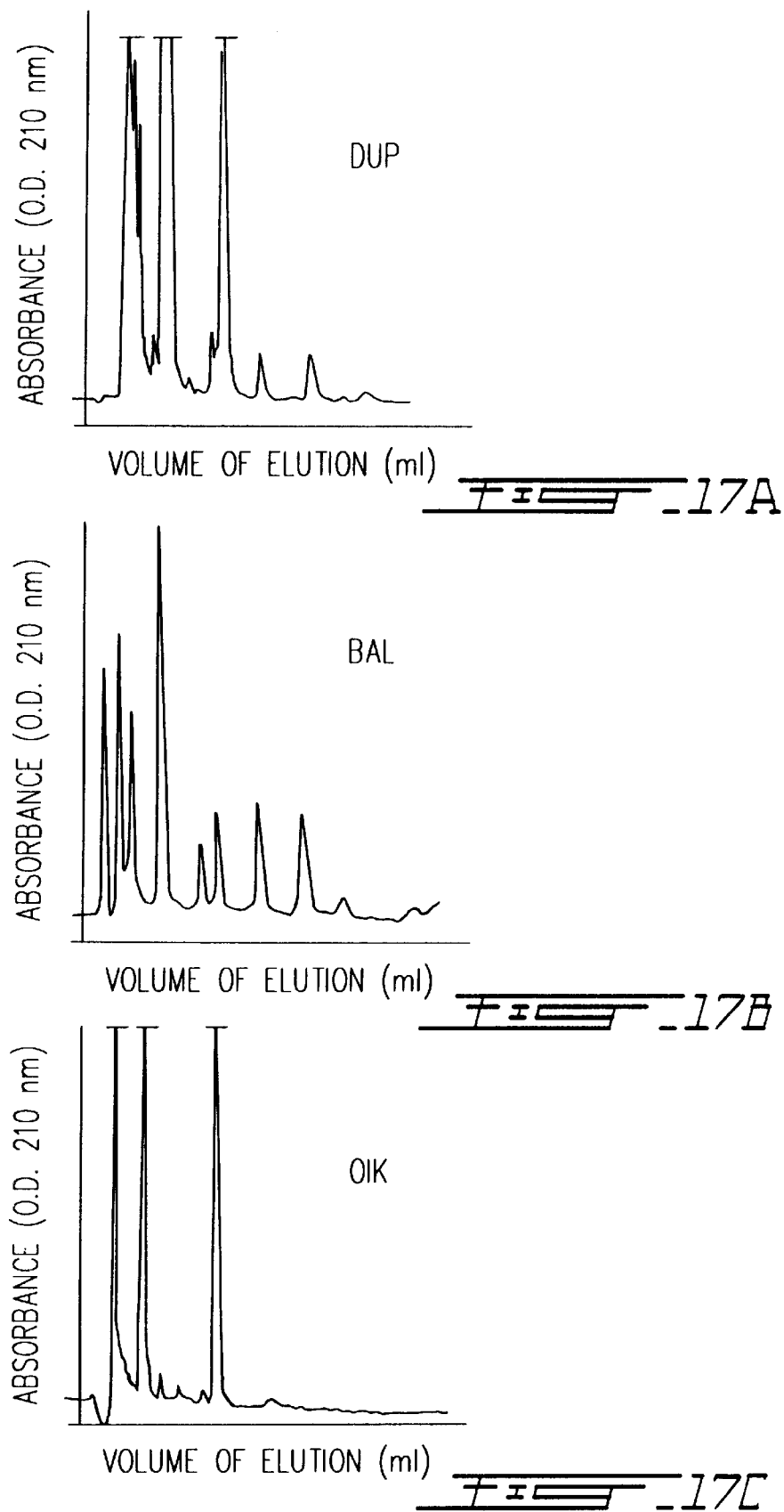

METHODS OF USING EXTRACTS OF SHARK CARTILAGE

BACKGROUND OF THE INVENTION

Cartilage is an avascularized tissue and has been studied as a potential candidate containing anti-angiogenic factors. It is also a tissue which is relatively resistant to tumor development. The tumor associated with cartilage, chondrosarcoma, is the least vascularized of solid tumors. Angiogenesis is one of the important factors in the development of a tumor. Discrete solid tumoral masses appear if the tumor cells can provoke the adjacent vascular network to expand to supply their nutritional needs. Therefore, the factors involved in the stimulation of angiogenesis have been studied for their role in the development of tumor and anti-angiogenic factors as well as drugs having an angiogenic inhibitory activity have been also investigated as tools for controlling the growth or for effecting regression of tumors.

It has been discovered that scapular cartilage in calves contains a substance that inhibits the vascularization of solid tumors (Langer et al., 1976). Because of its encouraging potential as anti-tumor agent, sources of greater supply of cartilage have been looked for.

Sharks are animals being a potential source of this kind of angiogenesis inhibitor because their endoskeleton is composed entirely of cartilage (6% of their body weight versus 0.6% in calves). Sharks have also as an interesting characteristic a low propensity to developing tumors. Many hypotheses have been elaborated to explain this low probability of developing tumors in sharks. Marchalonis et al. (1990) have shown IgM antibodies able to readily attack any aggressing agent. McKinney et al. (1990) have shown that sharks have macrophages capable of differentiating normal cells from neoplastic cells and of destroying the latter. Rosen and Woodhead (1980) have postulated that the rarity of tumors in elasmobranchs (a group to which pertain sharks and rays) might be due to the high ionic strength of their tissues, which is equivalent to a high body temperature. In these conditions, these authors believe that the immune system exerts a close to 100% immunological surveillance. Moore et al. (1993) have discovered that sharks produce an aminosterol having antibacterial and antiprotozoal properties. Finally, Lee and Langer (1983) and Folkman and Klagsbrun (1987) have shown that sharks produce a substance which inhibits neovascularization. Lee and Langer (op.cit.) have isolated this substance by extracting it from shark cartilage in denaturing conditions (guanidine extraction). This process of extraction is however very long (41 days), might generate extracts having denatured factors and the yield of active components is far from excellent. While the active substance isolated from calves has a molecular weight of about 16 kiloDas (kd), the same group of researchers have not given a precise molecular weight to the one retrieved in sharks. This substance is only defined has having a molecular weight higher than 3500 Da. Oikawa et al. (1990) have applied the same method of extraction as the one described by Lee and Langer, but of a much shorter duration (2 days instead of 41 days). The anti-angiogenic substance isolated from shark cartilage by Oikawa et al. is restricted to a molecule having a molecular weight ranging from 1000 to 10,000 Da. Schinitsky (U.S. Pat. No. 4,473, 551) has described a water extract of crude powdered shark cartilage which fraction of more than 100,000 Da has an anti-inflammatory activity alone or in combination with glucosamine. No suggestion of a component of this extract having an anti-angiogenic or anti-tumor activity is made in this patent. Kuetner et al. (U.S. Pat. No. 4,746,729) have isolated a polymorphonuclear neutrophil (PMN) elastase inhibitor from bovine cartilage. This inhibitor has been obtained from an aqueous extract of cartilage from which molecules of a molecular weight of less than 50,000 Da have been retained. Fractionation on Sephacryl S-200 has given numerous fractions from which those of 10–40 kDa have been pooled after they have demonstrated an anti-elastase activity. The active component has an isoelectric point of 9.5 and might have a molecular weight of about 15,000 Da. Kuetner et al. (U.S. Pat. No. 4,042,457) have also shown that bovine cartilage has a component of a molecular weight of less than 50,000 Da which has a cell proliferation inhibitory activity without any activity on endothelial cell growth. Balassa et al. (U.S. Pat. No. 4,822,607) have obtained a cartilage extract in an aqueous solution, which extract has an anti-tumoral activity. However, we have observed no anti-angiogenic activity in an extract obtained by reproducing Balassa's method. Spilburg et al. (U.S. Pat. No. 4,243,582) have isolated two glycoproteins of molecular weight of 65 kDa and of pI 3.8 from bovine cartilage (guanidine-extraction) which show anti-trypsin activity and an endothelial cell growth inhibitory activity.

Calf and shark cartilage contain many biological activities such as pro-inflammatory activity, anti-inflammatory activity, anti-angiogenic activity, lysozyme activity, cell growth-promoting activity, inhibitory activity against types I and IV collagenase, elastase, and other proteases like trypsin, chymotrypsin and plasmin. However, nobody has yet obtained a cartilage extract which comprises a pool of clinically valuable activities.

Shark cartilage anti-angiogenic component(s) have been generally tested in rabbit corneal pocket assay or in chick chorioallantoic membrane (CAM) assay. Up to date, whole powdered cartilage has been tested directly on tumors in vivo, on human melanoma xenograft implanted in nude mice (U.S. Pat. No. 5,075,112), as well as tested in CAM tests for its anti-angiogenic effect. Even though an anti-tumoral effect has been assigned to cartilage extracts, this effect has most often been attributed to the anti-angiogenic component which deprives the tumor of blood supply. Up to now, there is no evidence that a shark cartilage has a direct effect on tumor cell proliferation.

A few methods of obtaining shark cartilage extracts and fractions are already known. Some of them produce a powdered crude cartilage without any extraction (U.S. Pat. No. 5,075,112). Others use denaturing agents like guanidine (U.S. Pat. No. 4,243,582). Others perform a pre-treatment of cartilage by way of an enzymatic digestion to get rid of any muscular, nervous or vascular structures surrounding the cartilage, which pre-treatment step is followed by the elimination of fats in organic solvents, and then the active components are extracted in an aqueous phase. (Balassa et al. U.S. Pat. Nos. 3,478,146, 4,350,682, 4,656,137 and 4,822,607). The effect of such pre-treatment on the preservation of the integrity of the biologically active cartilage components is not known. If too extensive, an enzyme digestion may hydrolyse active proteic components. For example, Balassa's method (U.S. Pat. No. 4,822,607) produces a liquid extract without anti-angiogenic activity; this lost may be the result of such enzymatic degradation. Balassa's method does not include a fractionation step which would further enrich an extract in active components. Others simply produce aqueous extracts (in water (U.S. Pat. No. 4,473,551) or salt solutions (U.S. Pat. No. 4,746,729)) of cartilage by eliminating the unsolubilized material.

Among the latter, specific fractions of specific molecular weights have been particularly retained for further study and purification (see discussion above).

The above-cited methods have several drawbacks. They may denature some valuable components. When such might not be the case, they have the disadvantage of being too lengthy to be of a practical purpose. Moreover, the lengthy methods do not necessarily yield sufficient amounts of active components, and among the recovered components, some are not recovered at all or in insufficient yield to show detectable activity or some have been disregarded by focusing on the obtention of specific activities.

Angiogenesis is not only involved in cancer development. Many diseases or conditions affecting different physiological systems (indicated in parentheses) are angiogenesis-dependent among which the following examples: arthritis and atherosclerotic plaques (bone and ligaments), diabetic retinopathy, neovascular glaucoma, macular degeneration, ocular herpes, trachoma and corneal graft neovascularization (eye), psoriasis, scleroderma, rosacea, hemangioma and hypertrophic scarring (skin), vascular adhesions and angiofibroma (blood system). Therefore, any new and potent anti-angiogenic "factor" could find an use in the treatment of these diseases as well as in cancer therapy and other angiogeno-dependent diseases. Moreover, since many of the above-mentioned diseases and conditions also have an inflammatory component, any new and potent anti-inflammatory "factor" could find a use in the treatment of these diseases and conditions as well as of any other inflammatory diseases or conditions. Furthermore, since proteases like collagenases are involved in a diversity of diseases and conditions like cancer and premature aging because of its collagen degrading activity, a new and potent anti-collagenolytic "factor" could find a use in the treatment of diseases or conditions having a collagenolytic component. Because angiogenesis, inflammation and proteolysis may be encountered alone or in combination in a large variety of diseases or conditions, a product capable of antagonizing at least all these activities without affecting normal body functions would be of a great therapeutic value.

STATEMENT OF THE INVENTION

The present invention provides a new method of producing cartilage extracts which have the advantage of containing a multiplicity of therapeutically valuable activities. Among those, anti-angiogenic, anti-inflammatory, anti-collagenolytic, in vivo anti-tumor proliferating and direct in vitro anti-tumor proliferating activities have been confirmed to be present in satisfying concentrations in a shark cartilage extract. Other activities await identification or confirmation. All activities have been obtained in a liquid extract of shark cartilage, and some of them have been obtained or verified in a solid extract of the same.

The present invention relates to a new process for the obtention of a liquid extract of cartilage having a substantial portion of the biologically active hydrosoluble components present in intact cartilage, which comprises the following steps:

a) homogenizing the cartilage in an aqueous solution in conditions compatible with the preservation of the integrity of said biologically active components until the cartilage is reduced to particles whose size is lower than or equal to about 500 µm, resulting in a mixture of particles and of a crude liquid extract having said biologically active components;

b) centrifuging said homogenate to separate particles from the crude liquid extract; and c) further separating the crude liquid extract so as to obtain a final liquid extract containing cartilage molecules having a molecular weight lower than or equal to about 500 kDa.

This new process has the advantage of being easy to perform and efficient. High yields of cartilage extract have been obtained, which extract, particularly obtained from shark cartilage, contains at least all the above-mentioned biological activities. It is preferably performed at cold temperature (about 0 to 20° C.), in non-denaturing conditions (preferably in pure water), at a near neutral pH (about 5 to 8) to maximize the probability of recovering compounds of unknown physico-chemical characteristics. According to this process, cartilage components can be extracted in a low volume of solution (as low as 1 L for 1 Kg of cartilage), and after a short period of homogenization (as short as 10 to 20 minutes). For the recovery of a solid extract, the same process is used, except that the pellet is recovered and lyophilized, disregarding the supernatant.

This invention relates to cartilage extracts, particularly to extracts from elasmobranch species, more particularly the shark. The solid extract has shown activity. It may contain collagen and non-hydrosoluble components. It may also contain a residual activity of what was extracted in the total liquid extract. The total liquid extract is very rich in activity. It can be used as such or it can be concentrated. A concentration step which favors the maintenance of biological activities has been privileged. Recourse to methods which could deteriorate the active components like heat-evaporation has been avoided by caution. Ultrafiltration on a membrane having a molecular weight cut-off value of about 1 kDa has been used to concentrate the liquid extract of this invention. Nanofiltration on a membrane having a molecular weight cut-off value of about 100 Da was even better to concentrate the biological activities of the liquid extract (anti-antiangiogenic, anti-collagenolytic). As a result, a concentrated extract containing molecules of a molecular weight comprised between about 0.1 and about 500 kDa was tested.

The liquid extract (0 to 500 kDa) has been further fractionated to characterize the active components thereof. Numerous active fractions have been obtained by different methods. Some of them tested for their anti-tumoral activity on tumor cell lines have been grossly characterized by their molecular weight and isoelectric point. Others have been assigned an activity, particularly anti-collagenolytic or anti-angiogenic. These fractions await complete characterization and identification. Therefore, valuable activities are recovered in a total liquid extract and fractions thereof, which may be advantageously used. In "lieu" of administering high amounts of powdered cartilage, a more acceptable and enriched extract may now be administered.

The present invention also relates to any therapeutic or cosmetic compositions comprising as an active ingredient an effective amount of one of the above-cartilage extracts. Most interest has been drawn to formulations for use in dermatology and cosmetology. This interest comes from the observed activities of the cartilage extracts. In this respect, the observed anti-angiogenic, anti-collagenolytic and anti-inflammatory activities, and the antagonistic effect of cellular differentiation mediated by signalization pathways like Protein Kinase C in keratinocytes have been considered as opening avenues to the use of the shark cartilage extracts in compositions and methods for the reduction of inflammation or irritation, the regulation of wrinkle or skin atrophy, the retardation of premature aging, the reduction of acne, the improvement of skin barrier function, the reduction of dark circle around the eyes, the reduction of the spider veins and varicosous, the regression of warts, and a skin soothing effect. Such methods are under the scope of this invention. Furthermore, since the shark cartilage liquid extract has been successfully tested in cancer, arthritis, psoriasis and acne cases, compositions and methods for treating diseases or conditions having one or more components selected from the groups consisting of tumor proliferation, angiogenesis, inflammation and collagenolysis, are under the scope of this invention.

DESCRIPTION OF THE PRESENT INVENTION

The present invention will be more readily understood by way of the specific embodiments shown in the appended figures, which purpose is to illustrate the invention rather than to limit its scope:

BRIEF DESCRIPTION OF THE FIGURES

FIG. 13a) shows the profile of fractions 1 to 13 while FIG. 13b) shows the profile of fractions 14 to 20.

FIGS. 16a), b) and c) show a FPLC migration pattern of three different extracts of shark cartilage. In FIG. 16a), DUP stands for a cartilage liquid extract according to this invention.

FIGS. 17a), b) and c) show a HPLC migration pattern of the same extracts defined in FIGS. 16a), b) and c).

In a specific embodiment, cartilage has been obtained from healthy sharks Black Spiny Dog Fish and Common Spiny Dog Fish. Any muscular and connective tissue has been removed by scraping with ethanol-treated scalpels and scissors. The cartilage was then vacuum-packed in plastic bags and frozen to −20° C. for further use. In the present process embodiment any source of cartilage may be used. We have chosen shark cartilage for reasons enunciated in the BACKGROUND section. It is believed that starting from elasmobranch cartilage (which includes sharks and rays as animal species of this group), near equivalent products would be obtained. The products will most probably be different both in nature and concentration of the active principles if mammalian source of cartilage is used.

Figure 19:
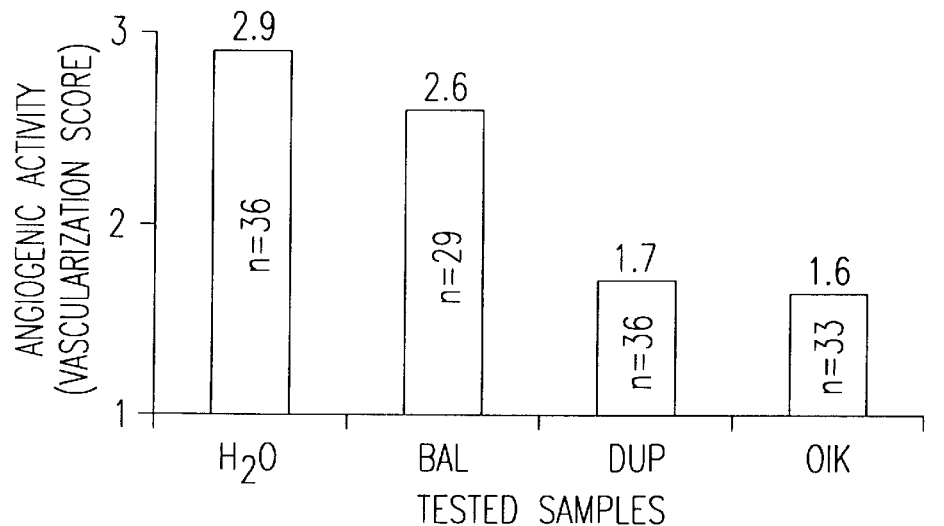
FIG. 19 shows an EVT comparison of the liquid extract of the present invention with the prior art.

Any variation in the preparation of cartilage prior to its extraction may be used as long as it does not substantially affect the activity of the product of interest (a total liquid extract or a particular fraction thereof, for example). Some active components may resist to proteolytic digestion as taught by Balassa et al. (U.S. Pat. No. 4,822,607) to rid the cartilage of any surrounding tissues, while others may not resist to such treatment. One of the activities which does not appear to resist to such pre-treatment is the anti-angiogenic activity (FIG. 19). Therefore if one wants to produce a liquid extract containing as much as possible of all the hydrosoluble active components to which are assigned separate activities, such a digestion step during the extraction procedure should be avoided or carefully monitored to prevent extensive hydrolysis or proteolysis.

PREPARATION OF CARTILAGE EXTRACTS

Clean cartilage was used fresh, thawed to 4° C., or frozen. Cartilage was then passed numerous times (more particularly three times) through the pores of an ethanol-aseptized meat chopper together with an adequate volume of water (an equal quantity (weight/volume) is about a minimal volume but can be increased without bearing any effect on the yield of recovery of valuable components). A low volume is preferred since it is more convenient to manipulate than unnecessary high volumes, from a practical point of view. In the practice, water has been purified by inverse osmosis and multiple filtration down to 0.1 µm filter. Many aqueous solutions (containing salts, for example) could be used in lieu of water. When recovery of a plurality of hydrosoluble activities is contemplated, working at a near neutral pH (5.0 to 8.0) and non-denaturing conditions are preferred to avoid lysis or denaturation of some of the cartilage active components. The behaviour of unknown proteins in aqueous solvents is not predictable; some may be more "comfortable" in an acidic pH, some at a basic pH. Furthermore, some proteins may be extractable in mild denaturing conditions, if such denaturation does not irreversibly affect the re-naturation of these proteins in aqueous solutions. For sake of clarity, any condition of extraction which is compatible with the preservation of biologically active hydrosoluble cartilage component is under the scope of this invention. Therefore, taking all these factors in consideration, performing a process of extraction of cartilage active components in pure water has been shown to be a judicious choice to recover with a very good yield, components having a yet to be define structure and behaviour.

The blend cartilage/water was then made homogenized by an agitation at a maximal speed in an kitchen blender at about 4° C. during 20 minutes; during the homogenisation the homogenate temperature increases near 20° C. Of course, the speed of the agitation as well as the volume of aqueous solution may influence both time and yield of extraction. Therefore, a reasonable range of homogenization time (defined to less than 500 µm particles) could be as low as about 10 minutes to as high as 24 hours, preferably between about 10 and 60 minutes. The temperature should be maintained to below about 10° C., to avoid any degradation of active components by endogenous enzymes, when no enzyme inhibitors are used. Ideally, a temperature close to 0° C. should be sought. Since normally such experimentation is made in a cold room, wherein the temperature can be maintained between 4 and 10° C., this range of temperature is judged acceptable in the present process. For sake of clarity and brevity, the terms "about 4° C." is hereinbelow used to designate this acceptable range of temperatures.

A liquefaction of this homogenate can be further obtained by submitting the latter to Polytron disintegrator during 10 minutes at about 4° C. if the blender did not sufficiently reduce the size of the particles. Alternatively, the blend can be simply homogenized in a more performing blender-disintegrator which, in our hands, saved the 10 min in the liquefaction step. At the end of the completed homogenisation step, residual particle size is less than about 500 µm. Of course, the same acceptable ranges of time and temperature discussed for the obtention of the first grinded cartilage equally apply. The size of the particles after homogenization does not need to be ultra small. Therefore, the need to pulverize the cartilage before extraction can be avoided. Indeed, pulverization of cartilage in the form of a powder before aqueous extraction may on the contrary denature valuable activities, specially when such pulverization is performed in a freeze-dry state and/or in a heat-dry state.

The homogenate was centrifuged at 13,600×g during 15 minutes at about 4° C., which step is one way to separate quickly and efficiently a supernatant from a pellet. Variation and adjustment of these parameters are well within the knowledge of the skilled artisan, merely depending on the volume of homogenate and of the equipment used.

The resulting pellet was lyophilized for 24 to 48 hours. This first fraction will hereinbelow be defined as the lyophilizate or SOLID EXTRACT.

The supernatant can be filtered on a 24 µm Whatman filter, if necessary, to get rid of particles susceptible to affect the performance of an ultrafiltration column. The filtrated material was then ultrafiltrated at about 4° C. on an tangential flow filtration column having a porosity of about 500 kDa, which allows a first crude permeate to be obtained comprising hydrosoluble molecules of a molecular weight comprised between 0 and about 500 kDa. This crude permeating extract was filtered on 0.22 µm filter, and aliquoted in aseptic bottles for further use. This fraction will be further referred to as the crude permeate or the LIQUID EXTRACT.

An alternative, higher performing centrifuging procedure has been developed to obtain the pellet and the supernatant. The step of centrifuging at 13600×g for 15 minutes followed by a gross filtration on Whatman filters has been replaced by a centrifugation in a CEPA centrifuge equipped with a nylon pocket of a porosity of 1 µm, at 3000–4000×g. A 25 kg/25 L preparation can be centrifuged in that manner within 30 minutes and provide about 29 liters of supernatant. The aqueous volume obtained is higher than the starting volume of water, suggesting that a part of the water content of the cartilage itself has been harvested. The lyophilizate and the total liquid extract may have the following approximate composition which grossly takes into account the variations observed from batch to batch, and when using different material:

| SOLID EXTRACT: | |
|---|---|
| Lipids | 7.35%[1] |
| Proteins | 46.2%[2] |
| Humidity | 20.4% |
| Sodium | 4.16 mg/g[3] |
| Potassium | 2.64 mg/g |
| Calcium | 114 mg/g |
| Magnesium | 1.49 mg/g |
| Zinc and iron traces | |

| LIQUID EXTRACT: | |
|---|---|
| Lipids | 0.10–0.20%[1] |
| Proteins | 8–25 mg/ml[2] |
| Dry weight | 8–25 mg/ml |
| Humidity | 97–99% |
| Sodium | 30–220 mg/100 g[3] |
| Potassium | 30–40 mg/100 g |
| Calcium | 2.0 mg/100 g |

-continued

| LIQUID EXTRACT: | |
|---|---|
| Magnesium | 1.1 mg/100 g |
| Zinc and iron traces | |

[1,2] Measured following directives published in AOAC Official (1984) sections 16.219–220 and 2.055, respectively;
[3] Measured following the SAA procedure.

The protein content is evaluated by the Kjeldahl method, which indeed measures organic nitrogen (N). Organic nitrogen is converted to equivalent protein by using the following equation:

$$\text{Proteic content (mg/ml)} = (\% \text{ N} \times 6.25) \text{ OVER } 100$$

Carbohydrates being not detectable, one can presume that they are in one or another extract but under the form of proteoglycanes and/or mucopolysaccharides. It is possible that these compounds are included in the measured level of humidity. The lyophilizate contains an unexpected level of humidity which was measured by the OH— groups. Since the 20% water content is close to the percentage of carbohydrates normally retrieved in cartilage while the humidity of a lyophilizate should be close to 0%, this hypothesis remains to be verified.

Figure 1:
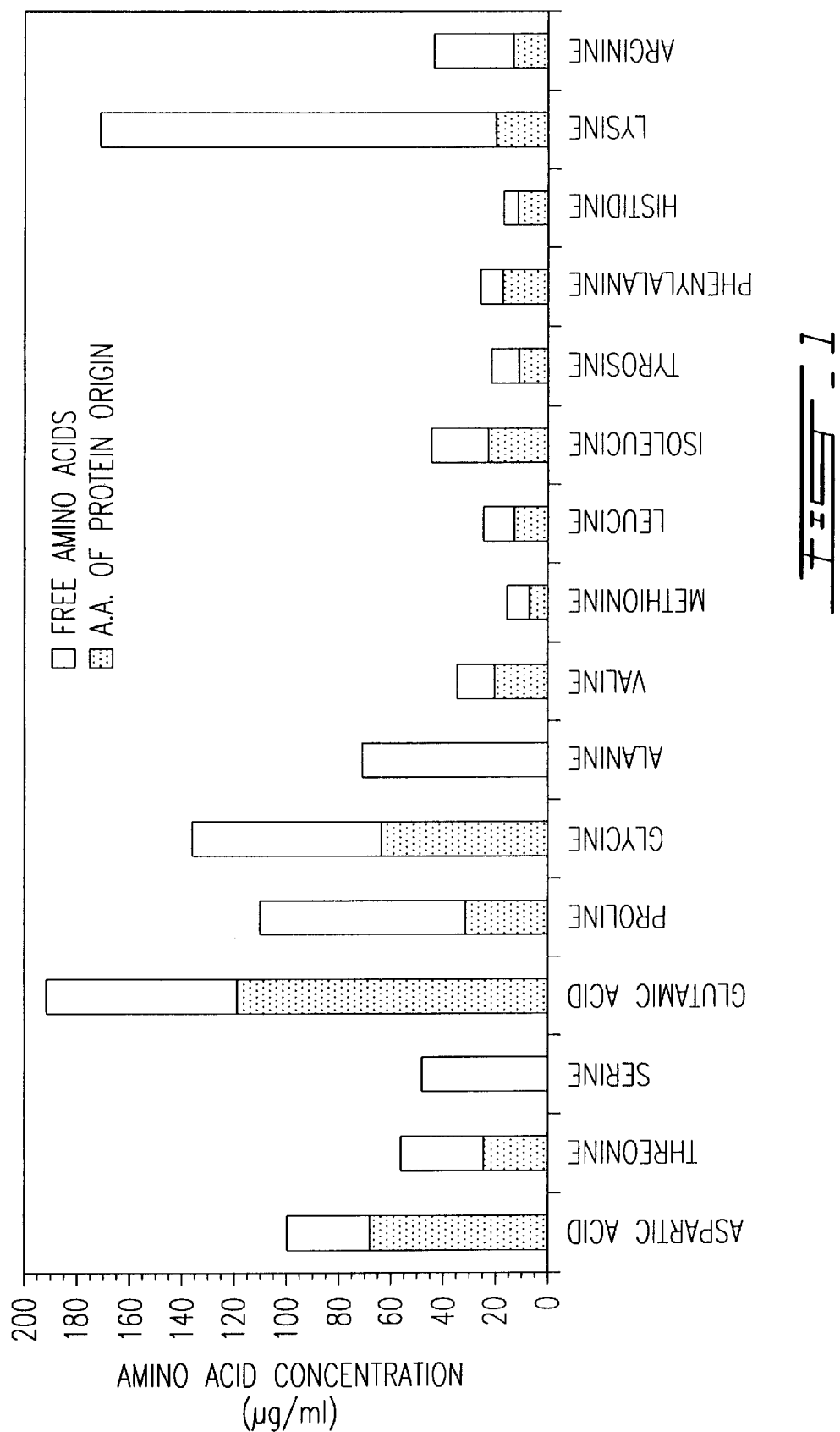
FIG. 1 shows the specific amino acid composition of the liquid extract.

The liquid cartilage extract was analyzed for its amino acid content. The average amount of total amino acids was approximately 1.1 mg per ml, with the free amino acids accounting for 0.67 mg (61%) and the amino acids of protein origin accounting for 0.44 mg (39%). The distribution of each amino acids is shown in FIG. 1. Significant amount of taurine was also detected (not shown).

The major amino acids present in the liquid extract are representative of proteins and peptides from cartilage. For example, Lysine, Glycine, Aspartic acid and Glutamic acid represent a large proportion of the amino acid content of the liquid extract and are the main components of the N-telopeptide intermolecular cross-linking in collagen (Hanson et al. (1992) J. Bone & Min. Res. 7: 1251–1258).

Microbial limit of the liquid extract has been controlled, applying U.S. Pat. No. XXIII <61> standards.

ACTIVITY ASSAYS

Solid Extract

In vitro assays:

These assays have been conducted on the hormono-dependent cancer cell lines MCF-7 and ZR75-1 (ATCC (R) numbers 22-HTB and 1500-CRL, respectively).

ZR75-1 cells:

a. Basal RPMI medium: 52 g RPMI 1640 without phenol red (Sigma R8755), 17.875 g Hepes (free acid; Sigma H0763), 0.55 g sodium pyruvate (Sigma P5280) and 10 g NaHCO$_3$ were mixed in 5 L of pure water and made pH 7.40 with NaOH.

If not used immediately, this solution must be protected from light to preserve photolabile substances. This solution was filtered, distributed in 500 ml sterile bottles and stored at 4° C. for a maximal period of three months.

b. Cell culture maintenance medium: Basal RPMI medium was supplemented with 10% (v/v) FBS (fetal bovine serum), 100 U penicillin G/50 µg streptomycin sulfate (Sigma P0906)/ml medium, 2 mM L-Glutamine (Sigma G1517) and 1 nM E$_2$ (β-estradiol Sigma E8875).

c. Experimental medium: Basal RPMI medium was supplemented with 5% FBSA (fetal bovine serum adsorbed on dextran-charcoal), 2 mM L-Glutamine, 100 U penicillin G/50 µg streptomycin sulfate/ml medium and 50 ng/ml insulin (Sigma). To this medium was added increasing concentrations of the above-described lyophilizate as well as different concentrations of E$_2$ ($10^{-12}$ to $^{-5}$M)

MCF-7 cells:

a. BASAL DME-F12 medium: DME-F12 medium (without bicarbonate and without red phenol; Sigma) was reconstituted following the manufacturer's directives in pure water. For one liter, 1.2 g of sodium bicarbonate was added and the pH made to 7.40 with NaOH/HCl. This solution was filtered, distributed in 500 ml sterile bottles and stored at 4° C. for a maximal period of three months.

b. Cell culture maintenance medium: Basal DME-F12 medium was supplemented with 10% (v/v) FBS (fetal bovine serum), 100 U penicillin G/50 µg streptomycin sulfate/ml medium, 2 mM L-Glutamine (Sigma) and 1 nM E$_2$.

c. Experimental medium: Basal DME-F12 medium was supplemented with 5% FBSA (fetal bovine serum adsorbed on dextran-charcoal), 2 mM L-Glutamine, 100 U penicillin G/50 µg streptomycin sulfate/ml medium and 50 ng/ml insulin (Sigma). As described for the ZR75-1 cells, lyophilizate and E$_2$ were added at the same concentrations.

d. Preparation of FBSA: Fetal bovine serum was mixed with 1% (w/v) charcoal (carbon decolourizing alkaline). A solution of dextran T70 was added to the charcoal-serum solution to achieve a concentration of 0.1% (w/v). The mixture was agitated overnight at 4° C. After centrifugation at 4° C. for 30 minutes at 10,000×g, the serum was decanted, mixed again with the same proportions of charcoal and dextran, agitated at room temperature for three hours and re-centrifuged. The serum was then heat-inactivated at 56° C. for 20 minutes, sterile filtered and aliquoted in sterile conical Falcon tubes.

Experimental culture assays and results:

ZR75-1 and MCF-7 cells were grown to reach a density of population of 20 000 cells/well on 24-well plaques or 150 000 cells/well on 6-well plaques, and treated in the presence or absence of different concentrations of lyophilizate as prepared above. To this effect, the solid cartilage extract is resuspended in culture medium and sterile filtered, so that hydrosoluble components thereof are recovered and tested. All experiments have been performed in triplicates. Culture media have been withdrawn and replaced by fresh media every two days. Cells were grown in an incubator under a constantly humidified atmosphere containing 5% CO$_2$, at 37° C., for 17, 7, 3 or 3 days, corresponding to the first, second, third or fourth experiment, respectively. Cell growth inhibition was measured by direct counting of the cells or by measuring the total DNA content of a well.

| | Cell Inhibition (%) | |
|---|---|---|
| Concentration of lyophilizate | MCF-7 | ZR75-1 |
| 1st experiment: 17 days | | |
| 1 mg/ml | 1.5 | 2.0 |
| 5 mg/ml | 14.33 | 33.6 |
| 10 mg/ml | 62.66 | 90.8 |
| 2nd experiment: 7 days | | |
| 1 mg/ml | 3.73 | 0.97 |
| 5 mg/ml | 15.7 | 29.0 |
| 10 mg/ml | 68.37 | 66.0 |

-continued

| Concentration of lyophilizate | Cell Inhibition (%) | |
|---|---|---|
| | MCF-7 | ZR75-1 |
| 3rd experiment: 3 days | | |
| 50 mg/ml | 95.8 | 95.0 |
| 100 mg/ml | 94.6 | 98.0 |
| 4th experiment: 3 days | | |
| 10 mg/ml | 34.4 | 51.5 |
| 20 mg/ml | 62.5 | 70.5 |
| 50 mg/ml | 95.8 | 95 |
| 100 mg/ml | 94.6 | 98 |

The above percentages of inhibition of cell growth demonstrate that the solid cartilage extract can inhibit in a dose-dependent manner the growth of the cells of these two cell lines.

Figure 2:
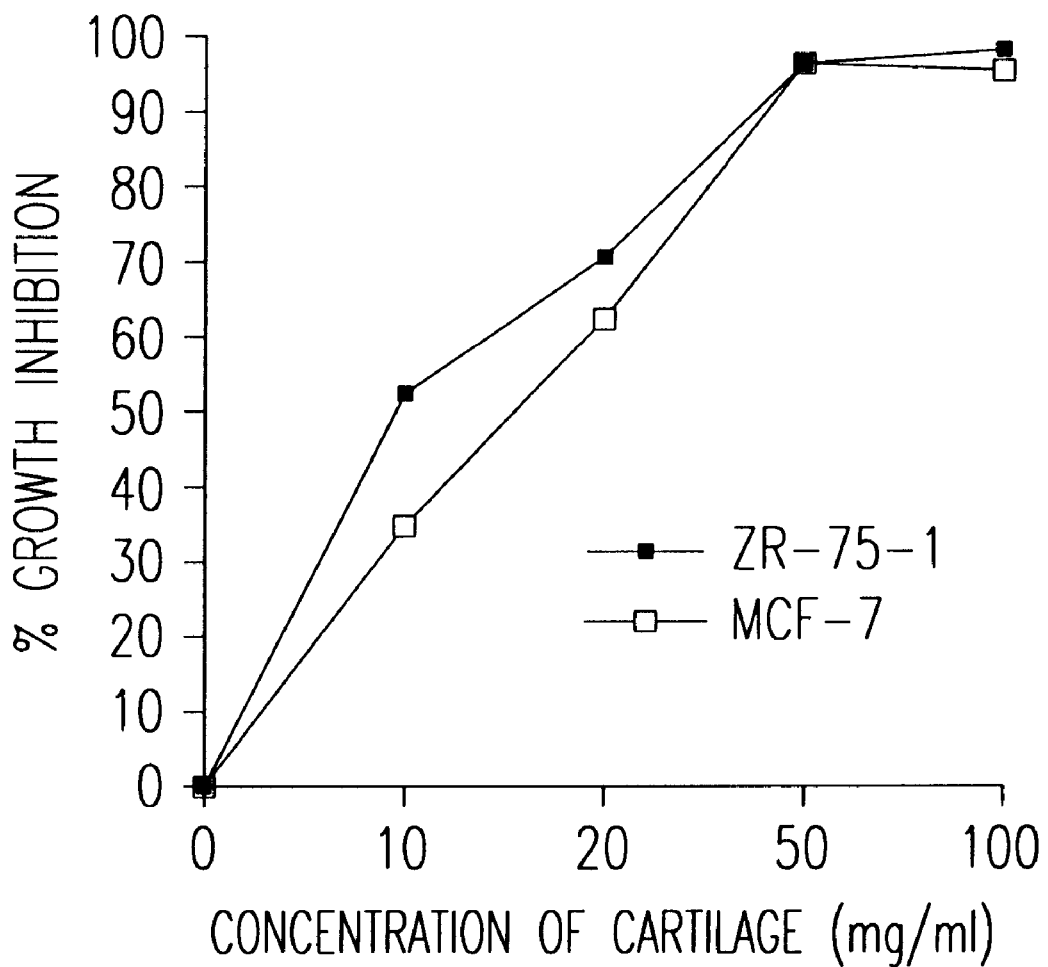
FIG. 2 shows a dose-response inhibitory activity of shark cartilage (solid extract) on ZR75-1 and MCF-7 cell lines.

FIG. 2 shows that doses of 50 and 100 mg/ml of the solid extract clearly provoke hypoplasia on these cell lines, after three days of treatment.

Figure 3:
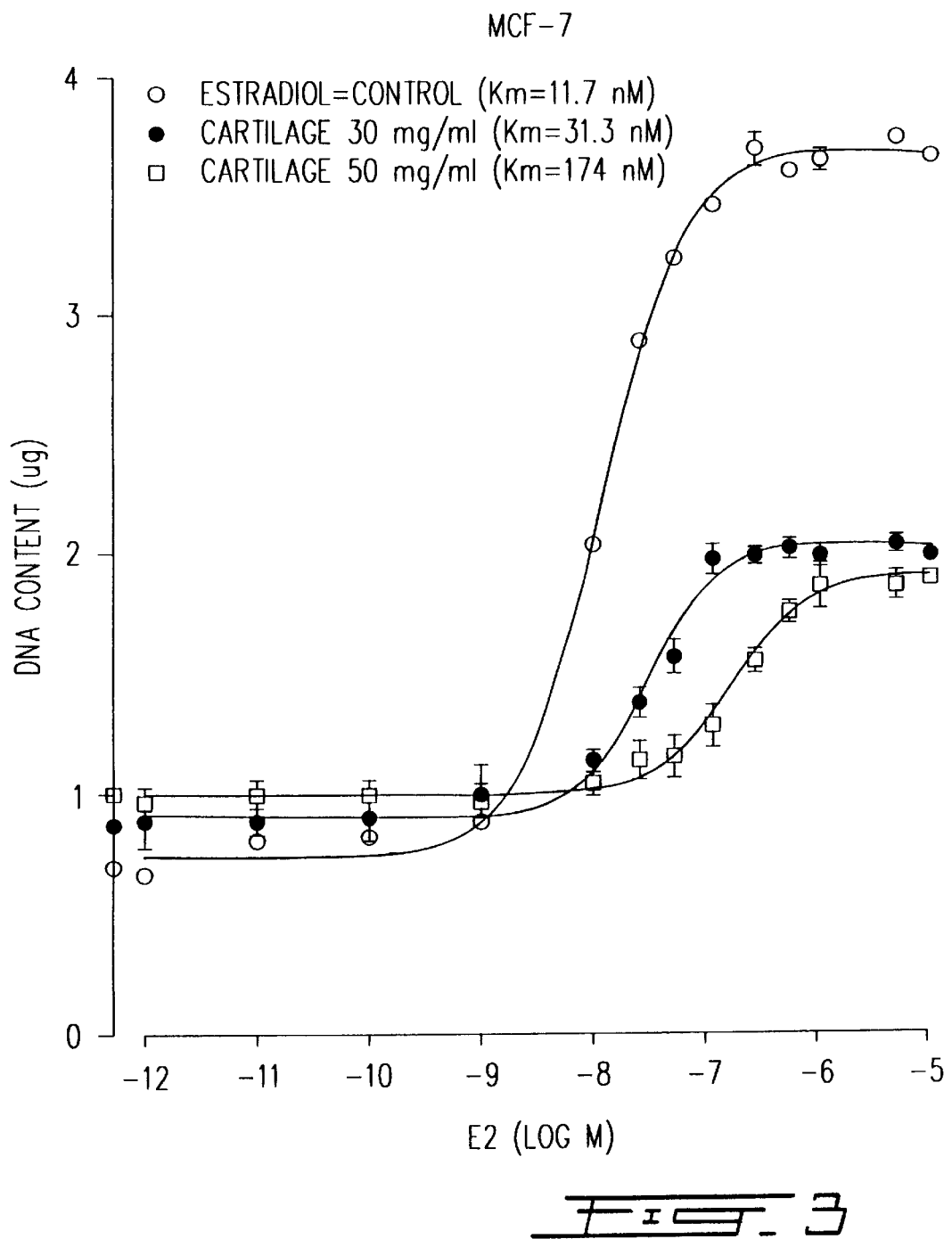
FIG. 3 illustrates dose-response curves of the quantity of MCF-7 cells in the presence of increasing concentrations of estradiol with or without two concentrations of solid cartilage extract.

FIG. 3 shows that, in the presence of $10^{-12}$ to $10^{-9}$M estradiol, treated cells respond like control cells by being non-stimulated by these hormone dosage rates. However, above 1 nM, control cells are strongly stimulated, and concentration of DNA reaches 3.75 $\mu$g in the presence of $10^{-7}$M estradiol (versus 0.69 $\mu$g in control without estradiol). In cells treated with 30 and 50 mg/ml of lyophilizate, DNA measured at the maximal stimulation is 1.9 and 1.8 $\mu$g, respectively. FIG. 3 shows that the affinity constant (Km) of the treated cells for estradiol is 3 and 16 times higher (31.3 nM and 174.0 nM) than the value of Km of the control cells (11.7 nM), in the presence of 30 and 50 mg/ml, respectively. This means that higher concentrations of estradiol are necessary to achieve the same growth of the cells when solid cartilage extract is present. Therefore, this extract diminishes the maximal response (90% inhibition thereof) and increases the affinity constant of the treated cells to estradiol.

In vivo assays:

DMBA induced rat mammary breast cancer model a. Description of the test system: Four hundred 40 day old female Sprague-Dawley rats (purchased from Charles River Co., St-Constant, Quebec) where adapted to their environment for 12 days. At that time, 20 mg DMBA/1 ml corn oil (9, 10-Dimethyl-1, 2-Benzanthracene; purchased from Sigma Chemical Co.) was administered by gavage. Three months after this treatment, 240 rats having developed a mammary breast cancer have been selected and distributed in two groups. The first group consisted of five sub-groups of rats. The rats of the treated groups were given a daily dose of increasing concentrations of the lyophilizate extract in 3 ml of water for eight weeks while the control group received the same volume of water. The second group consisted in four sub-groups of rats. The rats of the treated groups were also given a daily dose of the lyophilizate in 3 ml of water combined with or without the liquid extract, for ten weeks while the control group received the same volume of water. Only one sub-group of the second group of rats treated with a concentration of 3000 mg/Kg/day of the lyophilizate and 3 ml of the liquid extract was also given an intraperitoneal (i.p.) injection of a smaller dose of the liquid extract (about 8 mg of protein in 1 ml of water).

Rats were weighing 151–175 g at the beginning of the two experiments and received food and water ad libitum. The first group of rats had tumors of average diameter of 0.9 cm while the second group of rats had a tumor of average diameter of 0.6 cm.

b. Anti-tumor activity: The results are summarized as follows

| Daily doses of cartilage extract administered by gavage | % tumor growth inhibition (decrease of tumor diameter vs control) |
|---|---|
| 1st experiment: duration 8 weeks | |
| Placebo | 0 |
| 500 mg/Kg/day | 2 |
| 1000 mg/Kg/day | 4 |
| 3000 mg/Kg/day | 14 |
| 5000 mg/Kg/day | 15 |
| 2nd experiment: duration 10 weeks | |
| Placebo | 0 |
| 3000 mg/Kg/day | 12 |
| 3000 mg/Kg/day + 3 ml liquid extract | 18 |
| 3000 mg/Kg/day + 3 ml liquid extract + 1 ml inj. | 20 |

These results demonstrate that the lyophilizate contains an active component which is absorbed in the gastro-intestinal tract and slows down tumoral progression. This inhibition might be a direct effect on the tumor cells or an anti-angiogenesis mediated effect interfering with tumor growth.

The liquid extract also contains inhibitory activity since its administration caused an additional reduction of tumor size of about 6%.

These results also suggest that the lyophilizate may contain active components that are not hydrosoluble and/or that it may contain residual hydrosoluble active components. Therefore, in the last eventuality, one may consider that the pellet could be re-extracted in an aqueous solution to recover hydrosoluble components maximally, if the yield can be still improved.

c. HISTOPATHOLOGY: For evaluating the non-toxicity of the solid cartilage extract, the animals used in the above in vivo experiments were killed by decapitation and the following tissues were taken for analysis: liver, lung, kidneys, heart, brain, muscle and mammary glands. Fat was taken out of these tissues, after what they were fixed for two days in Bouin fluid. After dehydration in ethanol, the fixated tissues were embedded in paraffin. Sections thereof were obtained and mounted on glass slides, stained with haematoxylin and visualized under microscope.

The histological examination revealed that no deleterious effect was visible when using the largest doses of solid extract alone or when using the solid extract in combination with the liquid extract (data not shown).

This suggests that the lyophilizate and the liquid extract have a selective tumor size regressive activity.

Figure 4A:
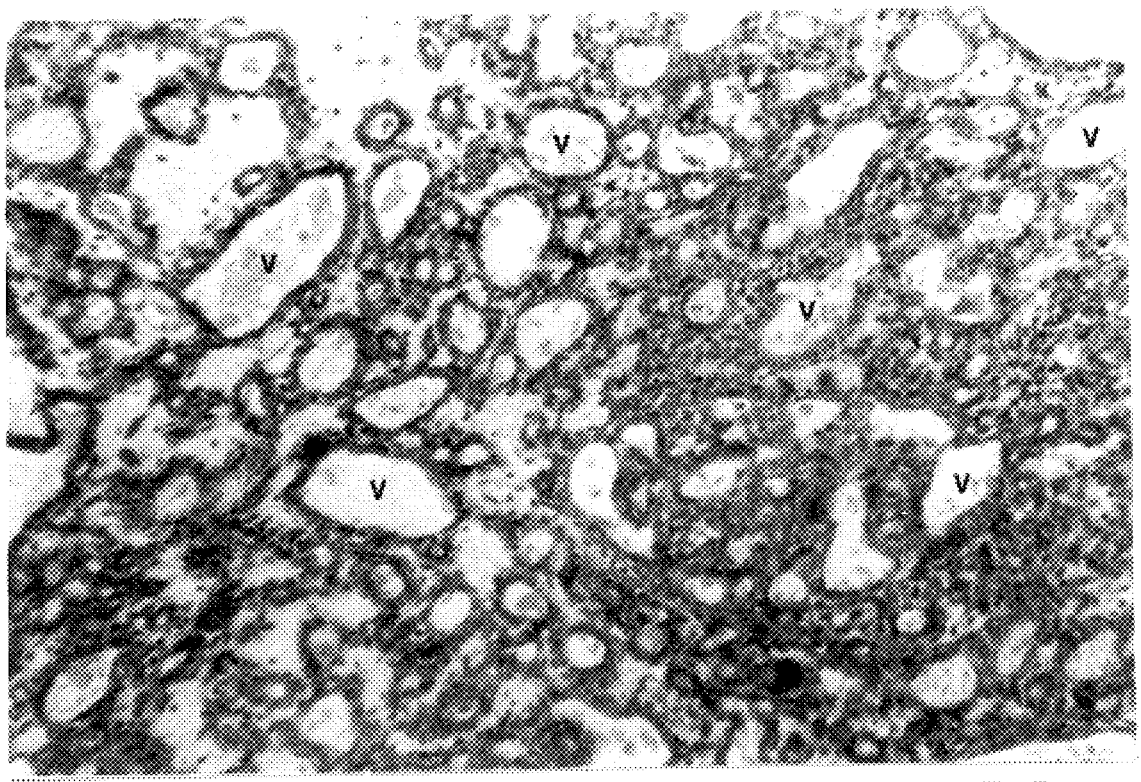
FIGS. 4 a) and b) show a comparison of mammary gland tumor sections of rats which have been administered by gavage water FIG. 4a) or a combination of solid and liquid cartilage extract FIG. 4b)). There are major histological changes due to the decrease in the number and size of blood vessels (V). Magnification X 120.
Figure 4B:
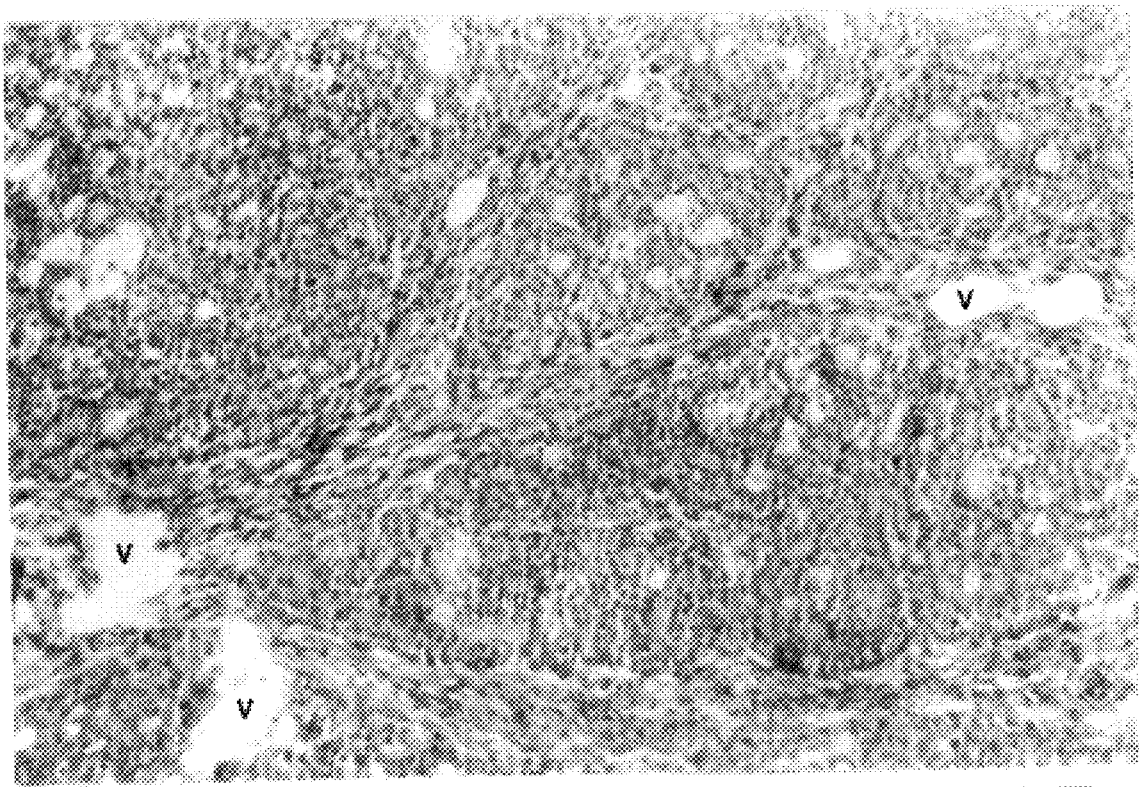
Figure 5:
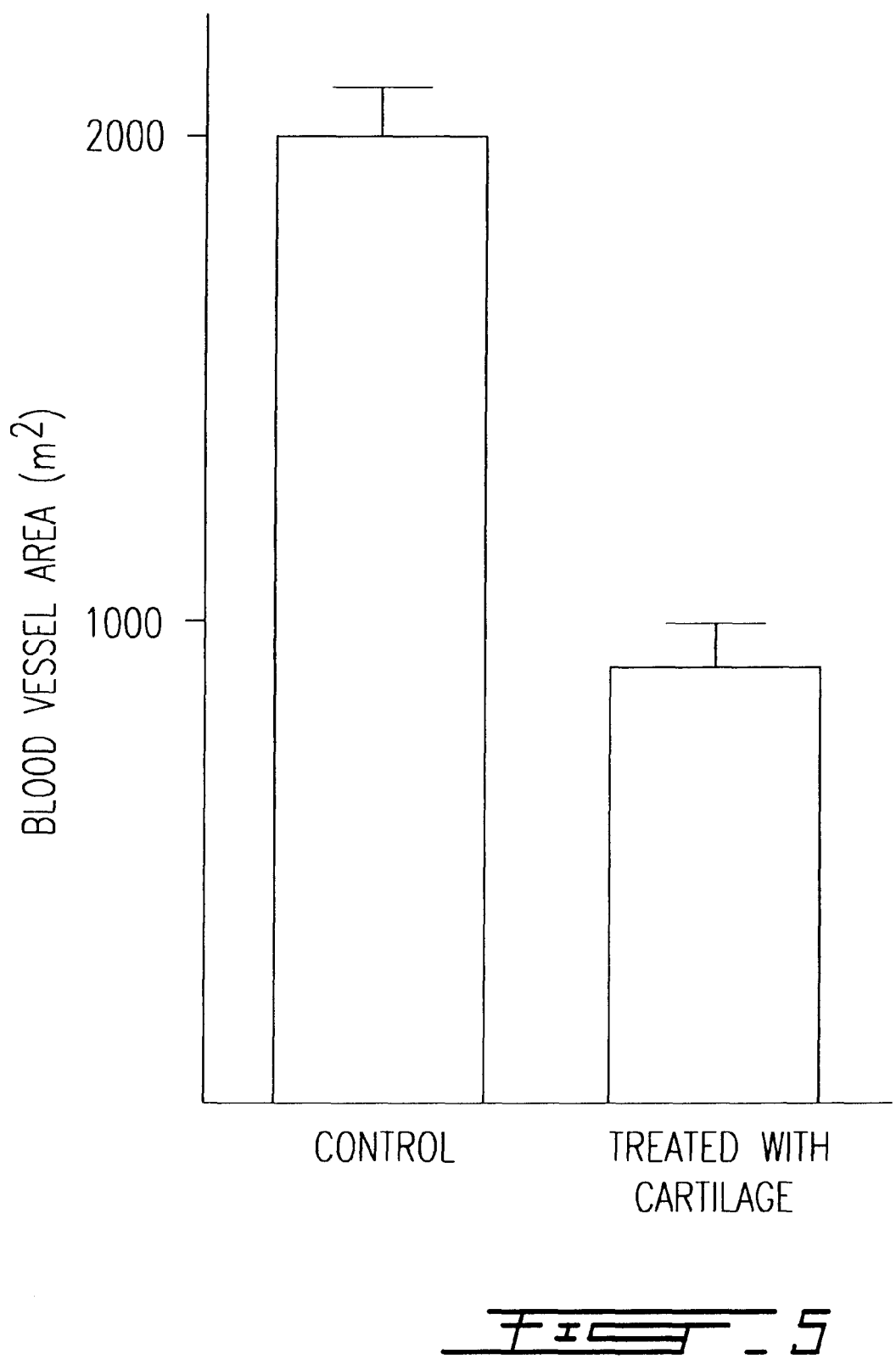
FIG. 5 is an histogram illustrating that cartilage treated rats have 50% decrease of the vascularization area in their tumor.

In mammary gland tumors (see FIGS. 4a and b), an important diminution (55%) of the area of blood vessels was observed in the group of rats having received solid and liquid cartilage extracts (FIG. 5).

The diminution of the tumor size might be due to an important decrease in its vascularization, to a direct effect on tumor cells, or a combination of both phenomenons. The anti-angiogenic effect of these extracts is well depicted above. The direct hypoplasiant effect has been observed in vitro on hormono-dependent cells, which remains to be confirmed in vivo.

Because the above-mentioned results showed that the liquid extract had an increasing effect over and above the effect of the solid cartilage extract on ZR75-1 cells, the components thereof were further investigated.

Liquid Extract

In vitro assay:

Tumoral cell lines:

Several tumoral cell line were grown in presence of liquid cartilage extract to examine whether the hypoplasiant activity observed with the solid extract (above section) was present.

Briefly cells were plated in 96 well plates and grown in culture media (specific for each cell type; for example, MCF-7 cells were grown as described in above section) in presence or not of various concentrations of liquid extract. Cell proliferation was measured using a MTT assay following 3 to 5 days of culture. The tumoral cell lines were:

CHANG: Tumoral hepatocytes
Hep-G2: Tumoral hepatocytes
A2780: Ovarian adenocarcinoma cells
MCF-7: Breast adenocarcinoma cells (estrogen dependent)
MCF-7-ADR: Breast adenocarcinoma cells Adriamicin resistant The liquid cartilage extract showed antiproliferative activity on all tumoral cell lines. The strongest inhibitions, 50 and 80%, were obtained at a concentration of 8.5 mg/ml (dry weight of liquid extract/ml of culture medium) on MCF-7 and A2780 cells, respectively.

Non-lyophilized and lyophilized liquid cartilage extract were equipotent in their ability to inhibit tumoral cell proliferation. This suggest that the inhibiton factor(s) is not denatured by this procedure of concentration.

Primary cultured cells:

a. Fibroblasts from neovascular glaucoma: In order to evaluate the specificity of activity on tumor cells, the permeate obtained after ultrafiltration was tested on mesenchyme originating cells, human TENON fibroblasts (HTFs), which are normal fibroblasts. Only the HTFs from two patients (one with neovascular glaucoma, NVG, and the other with primary open angle glaucoma, POAG) have been used.

Subculturing and Maintenance of HTFs: Each confluent culture were passaged by washing and detaching with 0.5 ml of 0.05% trypsin/0.5 mM EDTA (Gibco 610-5300 AG) for 5–10 minutes at 37° C. 1.5 ml of DME/F-12 medium containing 15% fetal bovine serum (FBS) was then added to neutralize trypsin/EDTA.

Association of the cells was made by triturating and transferring into 25 $cm^2$ T-flasks, into which additional medium containing 10%(FBS) was added. After confluence was reached, the HTFs were transferred into 75 $cm^2$ and eventually, into 180 $cm^2$ T-flasks. When enough cells were obtained, some cells were utilized for the experiments as described below, and others were simultaneously frozen to preserve identical passages for future experiments.

Experimental Protocols: When confluence was reached, cells from one patient growing in two or three identical 180 $cm^2$ T-flasks were dissociated by the procedure described above. After a short low speed centrifugation, they were counted with a ZMI Coulter Counter 216013, equipped with a 256-Channelyzer.

For all the in vitro experiments which follow, approximately fifty thousand cells were inoculated in 1 ml of DME/F-12 medium containing 1% FBS into each 16 mm dish and a 12-well plate. Seventeen hours (hrs) after seeding, 1 ml of fresh identical medium supplemented with 1% FBS ("absolute" controls) was added. Depending on the experimental design (see above and below), the 1% FBS medium was supplemented or not with GFs (Growth Factors) or with the liquid cartilage extract, and sterile filtered. On this day (day 0), some samples of cells were also counted to determine plating efficiency (which should be equal or greater than 95%).

Forty-eight hours after the onset of the experiments, the cells were rinsed, dissociated and counted again. The number of cells was expressed as a percentage of that obtained in the "absolute" controls.

Each "absolute" control, containing 1% or 5% FBS, respectively, and each experimental group, supplemented with 1% FBS and with an individual GF or liquid cartilage extract consisted of triplicate samples.

Each experiment was carried out on the cells of one or two patients at a time, and was repeated at least twice.

In these experiments, GFs, porcine platelet-derived growth factor (pPDGF) and human recombinant basic fibroblast growth factor (hr bFGF) (gift to Dr. P. Brazeau from Farmitalia Carlo Erba, Milan, Italy) were added in concentrations of 10 to 100 ng/ml in 1% FBS, respectively. Forty-eight hours after the onset of the experiment, the cells were dispersed by Trypsin-EDTA and counted on the Coulter counter. All triplicate values (columns 1, 2 and 3) appearing below equal one twentieth of counts per well.

Figure 6:
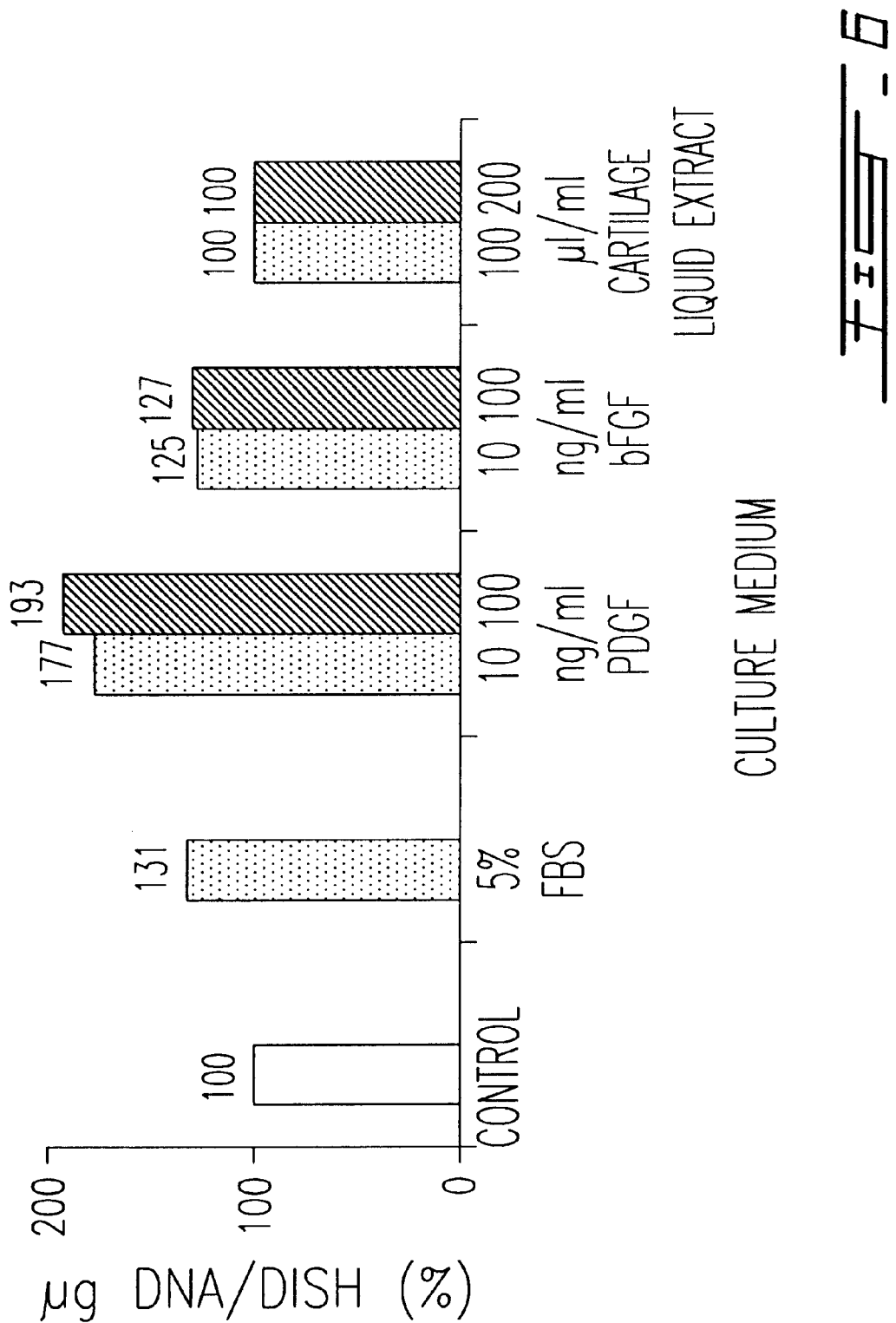
FIG. 6 shows that liquid cartilage extract has no effect on fibroblast cell proliferation.

Results: The results are summarized in FIG. 6. HTFs were obtained from the glaucoma of a 53 years old man. While growth factors like PDGF and bFGF showed a stimulating activity on HTFs (* $P<0.02$, ** $P<0.01$; determined by Student-Fisher Test), no effect, positive or negative, was obtained when these cells were grown in the presence of cartilage liquid extract (1 Kg/2 L). This suggests that the hypoplasiant activity of the liquid cartilage extract on tumoral cells is not universal and does not affect the growth of fibroblasts. The same cartilage extract neither had an effect on another type of fibroblast cells, HSF (Human Skin Fibroblasts; data not shown). Even though not tested, it is assumed that the solid extract also produces no effect on normal cells.

b. Endothelial cells from human umbilical vein (HUVECs): HUVECs were extracted with collagenase-controlled digestion as described in Jaffe et al. (1973). Pure endothelial cells were used before the fourth passage (trypsin-EDTA at each passage). Quality of the cells were analysed for their capacity to incorporate di-aceyl LDL and to be labeled with factor VIII.

Endothelial cells were plated at a density of 2 500 cell/$cm^2$ into sterile dished coated with gelatin. Cells were cultured with complete medium (Med199+heparin (90 µg/ml)+L-glutamine (2 mM)+bicarbonate+FBS (10%)+ECGS (120 µg/ml)) during 24 h to insure cell adhesion. Then, cells were washed 3 times with PBS and culture medium was added according to experimental conditions. The last PBS wash was considered as time 0.

Each experiment was performed in triplicate and statistic analysis was performed for comparison. Culture medium was changed after 24 h, and every other day. After 168 h of culture, BrdU (10 mM final) was added to each culture media and incubated 2h at 37° C. Then, cells were free with short trypsin-EDTA digestion and transferred into 96 well plates to allow ELISA detection of BrdU. ELISA was performed with a Boehringer Mannheim kit and method. A control was performed without cells to determine the basal level of background. Another control was performed by measuring the DNA content in the culture medium at the end of the incubation period to sort out whether the liquid cartilage extract affected cellular adhesion.

Cell proliferation was also evaluated with the amount of DNA present in the petri dishes. Each experiment was performed in triplicate and statistic analysis was performed for comparison. Culture medium was changed daily. After 168 h of culture, cells were lysed with Na-Citrate-SDS solution and incubated with Hoescht 33358. Samples were read at 365 nm with a spectrofluorometer.

Finally, the amount of cell present in petri dishes was also evaluated by measuring acid phosphatase activity. Each experiment was performed in triplicate and statistic analysis was performed for comparison. The activity of this enzyme showed a strong correlation with the number of endothelial cells in petri dishes (BrdU incorporation and Hoescht labeling; data not shown). Acid phosphatase activity was measured with a kit from Sigma Chemical Company (according to the manufacturer procedures with some modifications).

Figure 7:
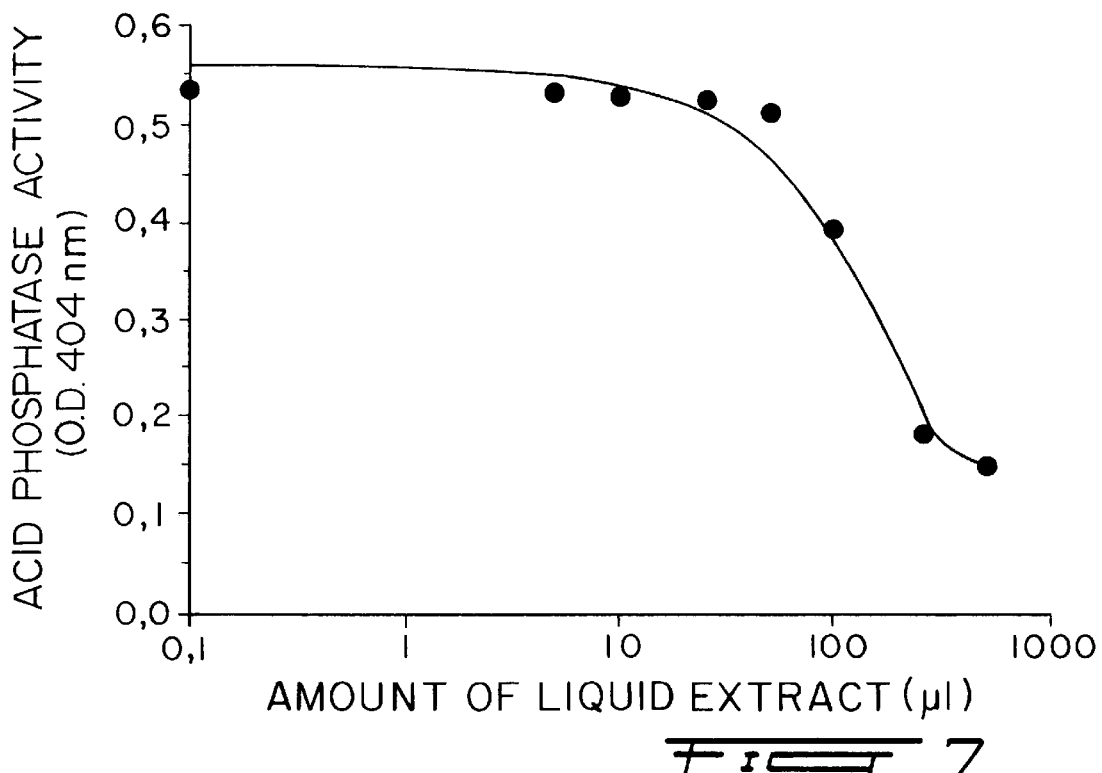
FIG. 7 shows a dose-response curve inhibition of liquid cartilage extract on HUVECs proliferation.

The results demonstrated a dose-response inhibition of endothelial cell proliferation with the liquid cartilage extract (FIG. 7). The ED50 obtained is approximately 90 $\mu$l of liquid extract (equivalent to approximately 1.5 mg dry weight present in the liquid extract).

c. Keratinocytes: Liquid cartilage extract was tested in keratinocytes which Protein Kinase C (PKC) was activated by triphorbol acetate (TPA), a known agonist of this cellular transduction pathway. Normal human epidermal keratinocytes were established as primary cultures (Matsui et al. (1992) J. Invest. Dermatol. 99: 565–571). Cultures were grown in a serum-free defined medium (KGM) containing epidermal growth factor (10 ng/ml), insulin (5 $\mu$g/ml), hydrocortisone (0.5 $\mu$g/ml) and bovine pituitary extract (70 $\mu$g/ml) in a modified MCDB 153 formulation.

Figure 8:
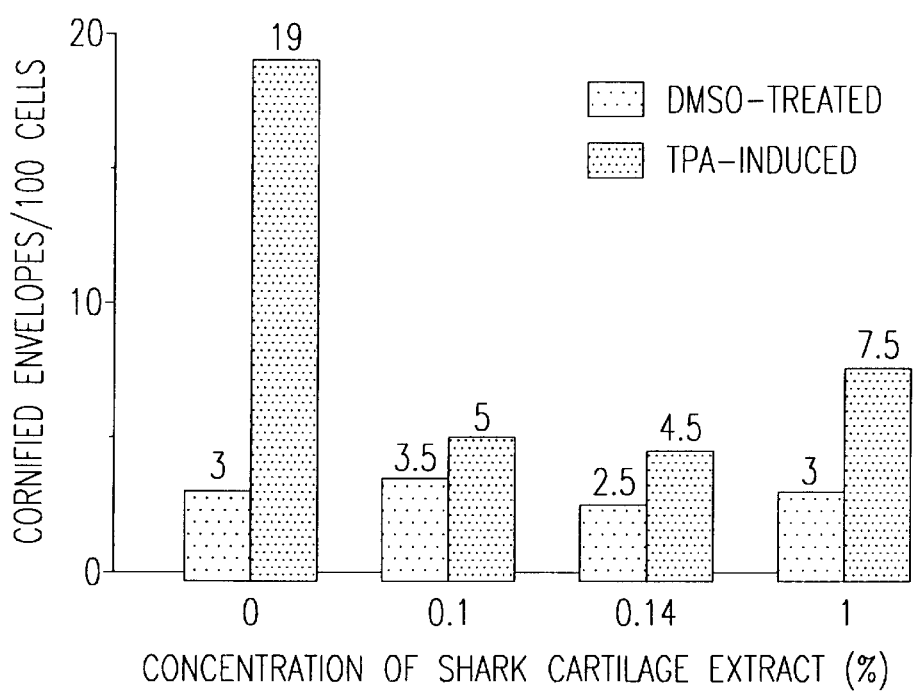
FIG. 8 shows that liquid cartilage extract inhibits TPA-induced keratinocyte differentiation.

Keratinocytes were grown to 70% confluence, and 48 h after refeeding with fresh medium, treated with either 200 ng/ml TPA or 2 $\mu$l/ml DMSO with no additional refeeding. Various concentrations of liquid cartilage extract were added or not to the culture medium. The results showed no effect of the liquid extract on keratinocyte proliferation; it also had no effect on TPA-induced inhibition of proliferation. However, liquid cartilage extract was able to inhibit TPA-induced keratinocyte differentiation (FIG. 8). The level of differentiation of the keratinocytes was increased 5-fold by TPA. Liquid cartilage extract by itself had no effect on cornified envelope formation. However, its presence inhibited TPA-induced cornified envelope formation by more than about 60%.

Recent publications have shown that PKC activation led normal keratinocytes to produce increased amounts of interleukin-8 (IL-8), a mediator of inflammation (Chabot-Fletcher et al. (1994) J.Invest.Dermatol. 103: 509–515). Moreover, psoriatic keratinocytes produce very high amounts of IL-8, which further promote neovascularization in psoriatic plaques (Nickoloff et al. (1994) Am.J.Pathol. 144: 820–828). Other growth factors and integrins are also involved and it may be important to widen the target molecule family that can be involved (Il-1, TNF, etc.). We do not know whether TPA-induction mimics psoriatic keratinocytes. If such is the case, these results suggest that cartilage may have no effect on normal keratinocytes in vivo, while it may have an effect on psoriatic (or activated) keratinocytes. Inhibition of the production of IL-8 in TPA-activated keratinocytes as well as in psoriatic plaques or keratinocytes by the liquid cartilage extract remains to be verified. Decreased IL-8 levels and/or other growth factors is an interesting possibility explaining the anti-inflammatory and anti-angiogenic effects of this extract.

Collagenase assays:

a. Assay 1: This assay is described in Knight et al. (1992) FEBS Let. 296, 263–266. The method utilizes a fluorogenic peptide substrate (Mca-pro-leu-glu-leu-Dpa-ala-arg-NH$_2$) mimicking the active site of metalloproteinases. This substrate has a fluorescent group (Mca) at one end and a fluorescence quenching group (Dpa) at the other. In the intact substrate, the quenching group effectively masks the fluorescence. Upon enzyme cleavage of the substrate the fluorescence in the test tube increases.

Collagenase activation is described in Weingarten et al. (1985) Biochemistry 24, 6730. 1 $\mu$g was diluted to 100 $\mu$l with 50 nM Tris-HCl, 10 mM CaCl$_2$. pH 7.5, 1 $\mu$l at 10 mg/ml solution of trypsin (in 1 mM HCl) was added and incubated for 15 min at 20° C. Activation was terminated by adding 10 $\mu$l of Soybean trypsin inhibitor (SBTI, 5 mg/ml). To each microcuvette was added:

25 or 50 $\mu$l inhibitor* (made up to 50 $\mu$l with water);

40 $\mu$l 50 mM Tris-HCl, 200 mM NaCl, 10 mM CaCl$_2$, pH 7.5;

8 $\mu$l activated collagenase** (67 ng final); and

2 $\mu$l substrate (1 mM stock solution in DMSO, 20 $\mu$M final).

Fluorescence was recorded at $\lambda$ex=328 nm, $\lambda$em=393 nm.

*: the inhibitor is defined as control substance (such EDTA, Ortho-phenanthrolene) or liquid cartilage extract.

**: the collagenase is defined as human type I, type IV, and amphibian tadpole collagenase; gelatinase has also been used.

b. Assay 2: This assay is described in Welgus et al. (1979) JBC 256, 9511–9516. The method uses SDS-PAGE to examine cleavage by collagenase, type 1 (MMP1). Collagenase type 1 makes a single cut in the native collagen molecule giving two fragments of 75% and 25% the size of the original collagen. After cleavage for several hours, the reaction is monitored by separating the products from the substrate by SDS-PAGE. The ratio of cleaved to uncleaved collagen is assessed visually after staining the gels with Comassie blue (or silver stain).

Figure 9:
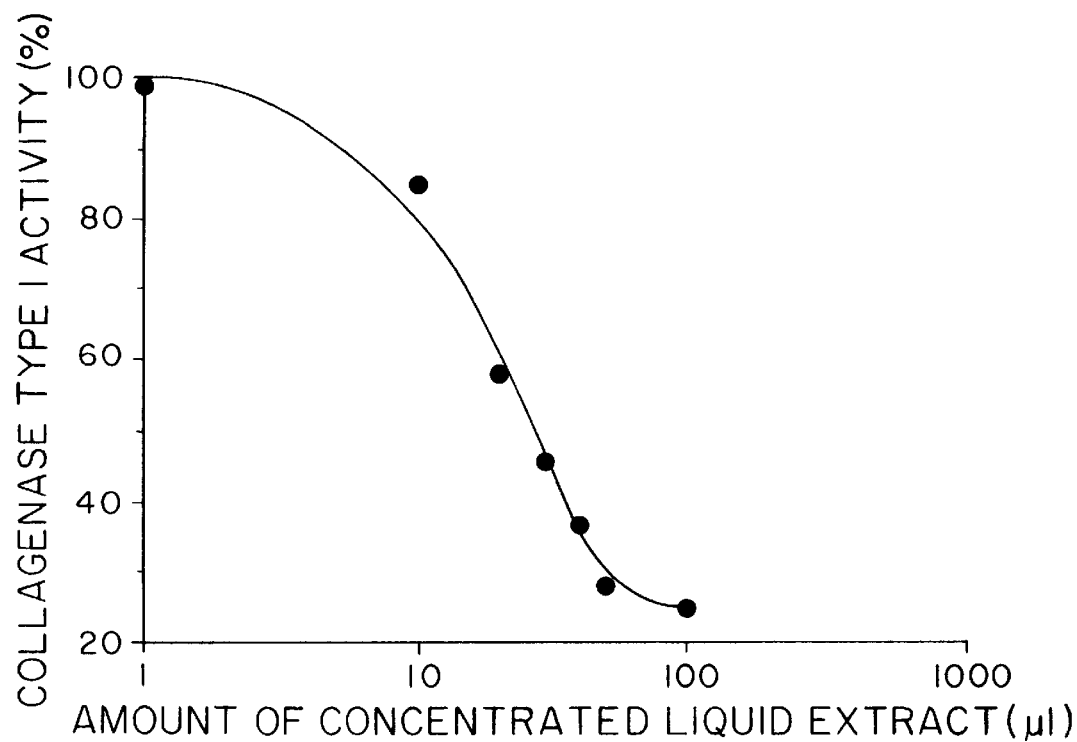
FIG. 9 shows a dose-response curve inhibition of liquid cartilage extract on collagenase activity.

21 ng of activated collagenase (see Assay 1) was added to 5 $\mu$g of calf skin collagen (Worthington) +/− inhibitor in a final volume of 20 $\mu$l. Reactions were incubated for 16 h at 35° C., then stopped by adding SDS-PAGE sample with 40 mM EDTA, boiled and loaded on a 8% acrylamide gel.

c. Dose-response inhibition: The results obtained with liquid cartilage extracts showed a dose-response inhibition of collagenase activity with both assays. FIG. 9 shows results obtained with assay 1. The ED50 is obtained with 30 $\mu$l of liquid extract (or 0.51 mg dry weight present in 30 $\mu$l of liquid extract).

In vivo assays:

Embryonic Vascularization Test (EVT):

a. Definition of the test-system: The normal development of the chick embryo involves the formation of an external vascular system located in the vitelline membrane which carries nutrients from the vitellus (yolk of an egg) to the developing embryo. When placed onto the vitelline membrane, anti-angiogenic substances can inhibit the blood vessel development that occurs in the vitelline membrane. To facilitate access to the vitelline membrane, chick embryos are transferred to a sterile culture box (Petri dish) and placed in a humidity- and temperature-controlled incubator. Embryos can then develop in this ex ovo condition for several days.

An aliquot of liquid cartilage extract is mixed with a methylcellulose solution and allowed to air-dry into thin discs. During this procedure intrinseque NaCl present in the liquid cartilage extract concentrates and interferes with the EVT when the amount per disc is over 25 $\mu$g. Therefore, desalinating the liquid extract may be necessary; dialysis with a membrane cut-off smaller to 100 Da or electrodialysis have been found acceptable methods.

Methylcellulose forms an inert matrix from which the liquid extract can diffuse slowly. Methylcellulose discs containing the liquid extract are placed on the external border of the vascular perimeter of the vitelline membrane where the angiogenic process is still active.

The effect of discs-containing liquid cartilage extract on proximal vascular developement is always compared to that of discs-containing water plus equimolar amount of NaCl. The discs are placed on the embryo's vitelline membrane on Day 0 or Day 1 of the ex ovo growth process; at this point, only beginnings of the main blood vessels are invading the vitellus. The embryos are then put in culture conditions until vascularization is assessed (approximately 24 h). Water- and liquid extract-containing discs are always added simultaneously on the vitelline membrane of the same embryo. Both discs are arranged in a symmetric fashion with respect to the cephalo-caudal axis of the embryo in order to minimize inter-individual variations when comparing shark cartilage extracts with controls.

b. Anti-angiogenic activity: EVTs were performed using different concentrations of protamine (37, 75 and 150 μg) as a positive control or liquid cartilage extract. After one day of culture, the level of vascularization in the area covered by the disc is graded by a pair of scientists in the usual blind fashion. To facilitate the location of the discs, a black O-ring is placed around it just after its deposition on the vitelline membrane. Evaluation scale for the EVT-test is based on the 1–2–3 score: (score=3) Normal vascularisation when compared to the opposite horizontal quadrant or the matching quadrant of a control embryo; (score=2) Blood vessels enter the area covered by the disc but vanish at mid-course. Major blood vessels cross the area covered by the disc but their trajectory is clearly affected or a decrease in the lateral branching density is observed; (score=1) No blood vessels are observed in the area covered by the disc or their parh is rapidly deviated in a way to escape from the area covered by the disc. Blood vessels do not grow beyond the area covered by the disc except if they bypass the latter and go beyond it.

Figure 10:
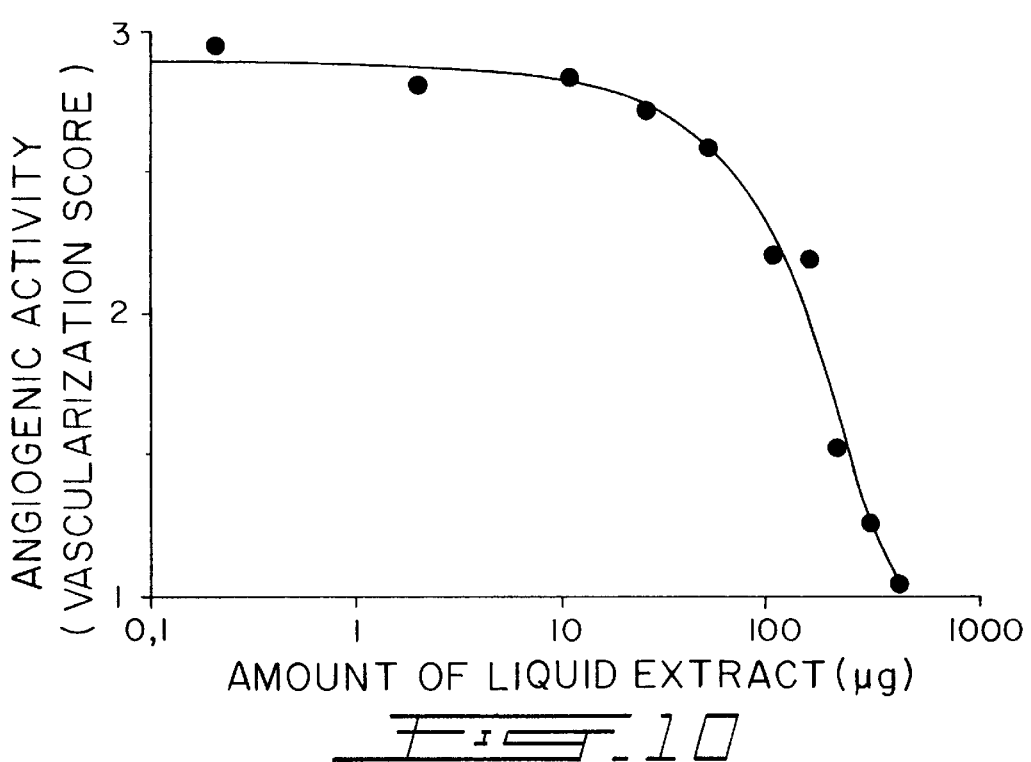
FIG. 10 shows a dose-response curve inhibition of liquid cartilage extract on the Embryonic Vascularization Test (ex ovo).

A dose-response inhibition was obtained with protamine (data not shown) and the liquid cartilage extract (FIG. 10). The ED50 was obtained with about 170 μg of dry liquid extract (dry weight present in the liquid extract). Wilcoxon-signed rank statistical test was used to compare the significance of the differences between the two discs (water and cartilage extract) placed on the same egg.

Mouse mammary adenocarcinoma model:

a. Description of the test-system: The anti-tumoral potential of the liquid cartilage extract was tested with a mouse mammary adenocarcinoma model (allograft). The test-system consisted to subcutaneously inoculate BALB/C mice with $1\times10^6$ DA3 cells. These cells originate from a murine mammary adenocarcinoma induced by 7,12-dimethylbenzanthracene (DMBA). The model was established by Daniel Medina (J. Natl. Cancer Inst. (1969) 42: 303–310; ibid. (1976) 57: 1185–1189). Inoculated cells grow slowly in vivo and form a solid tumor with a low metastatic prognosis.

DA3 cells were maintained in RPMI 1640 medium supplemented with 1 mM mercaptoethanol, 1M Hepes buffer solution, 100 mM Na pyruvate, 200 mM L-glutamine, 10 mM non-essential amino acids, 1M vitamins, 10% fetal bovine serum, 1% penicillin-streptomycin at 37° C. with 5% $CO_2$. For tumor induction, cells were grown to 70% confluence in complete medium and then collected using trypsin-EDTA solution. Cells were then centrifuged and washed three times with phosphate buffer solution, and resuspended at a dilution of $1\times10^6$ cells/0.1 ml.

Figure 11:
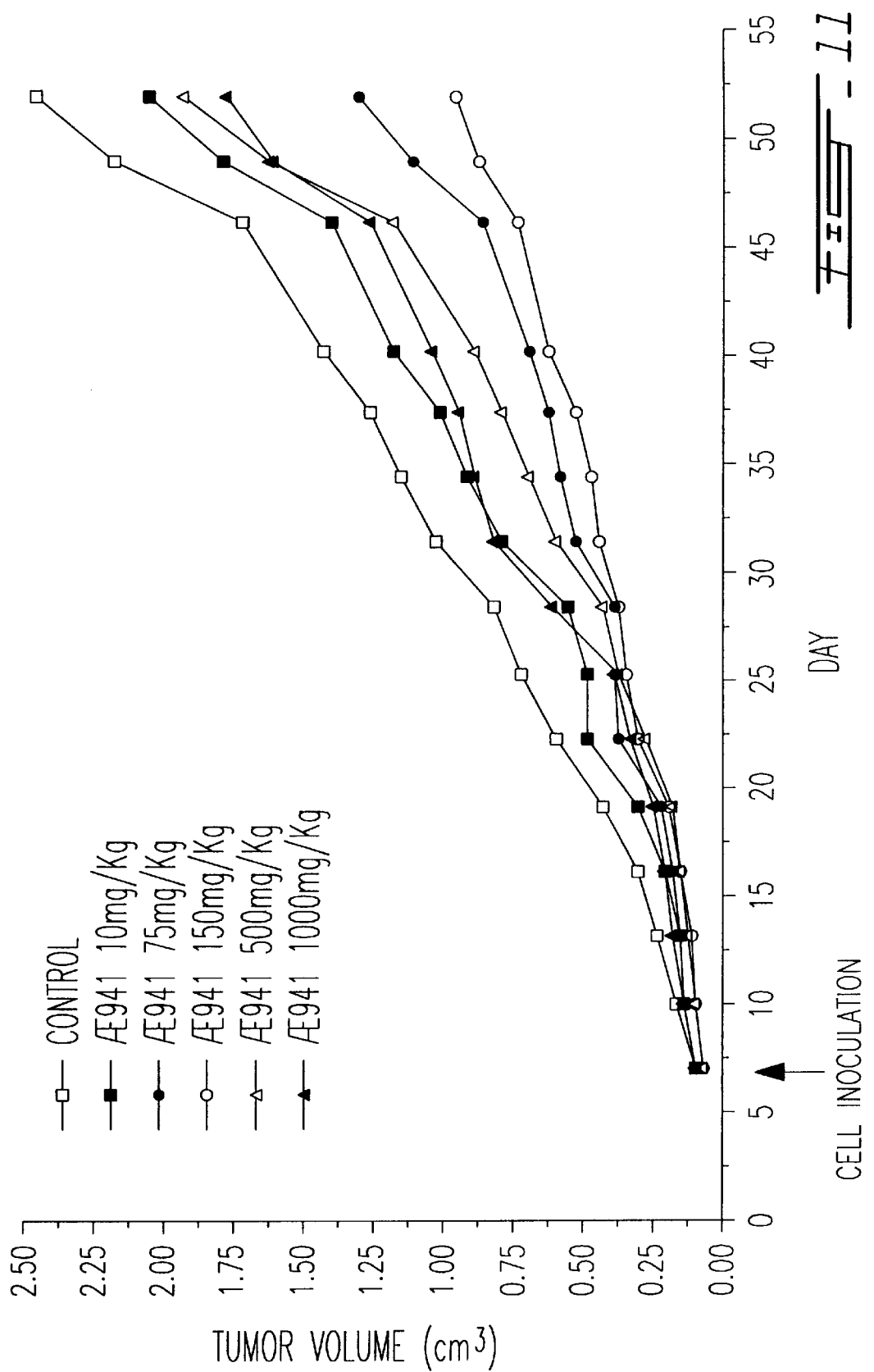
FIG. 11 shows the effect of various doses of liquid cartilage extract on tumoral growth inhibition in mice.

DA3-cells inoculated mice (n=15) received daily oral administration of a shark cartilage liquid extract or a placebo (saline solution). The treatments began 7 days after DA3 cells inoculation. Various concentrations of liquid extract were tested. The amount of liquid extract administred is expressed with the amount of dry weight present in the liquid extract. The test articles were prepared as described here: liquid extract was lyophilized and resuspended in water at various concentrations (0.2, 1.5, 3, 10, and 20 mg per 200 μl). The final doses that were administred daily were 10, 75, 150, 500, and 1000 mg/kg of body weight.

b. Anti-tumor activity: Results show that the maximum inhibition of tumoral progression was obtained with the administration of about 75 mg/kg of liquid extract (FIG. 11). Interestingly, larger doses were less potent. This suggests that the liquid extract contains substances that can inhibit tumoral progression and other substances that can inhibit the action of the tumoral inhibitors. This phenomenon has already been reported for biological drugs.

Figure 12:
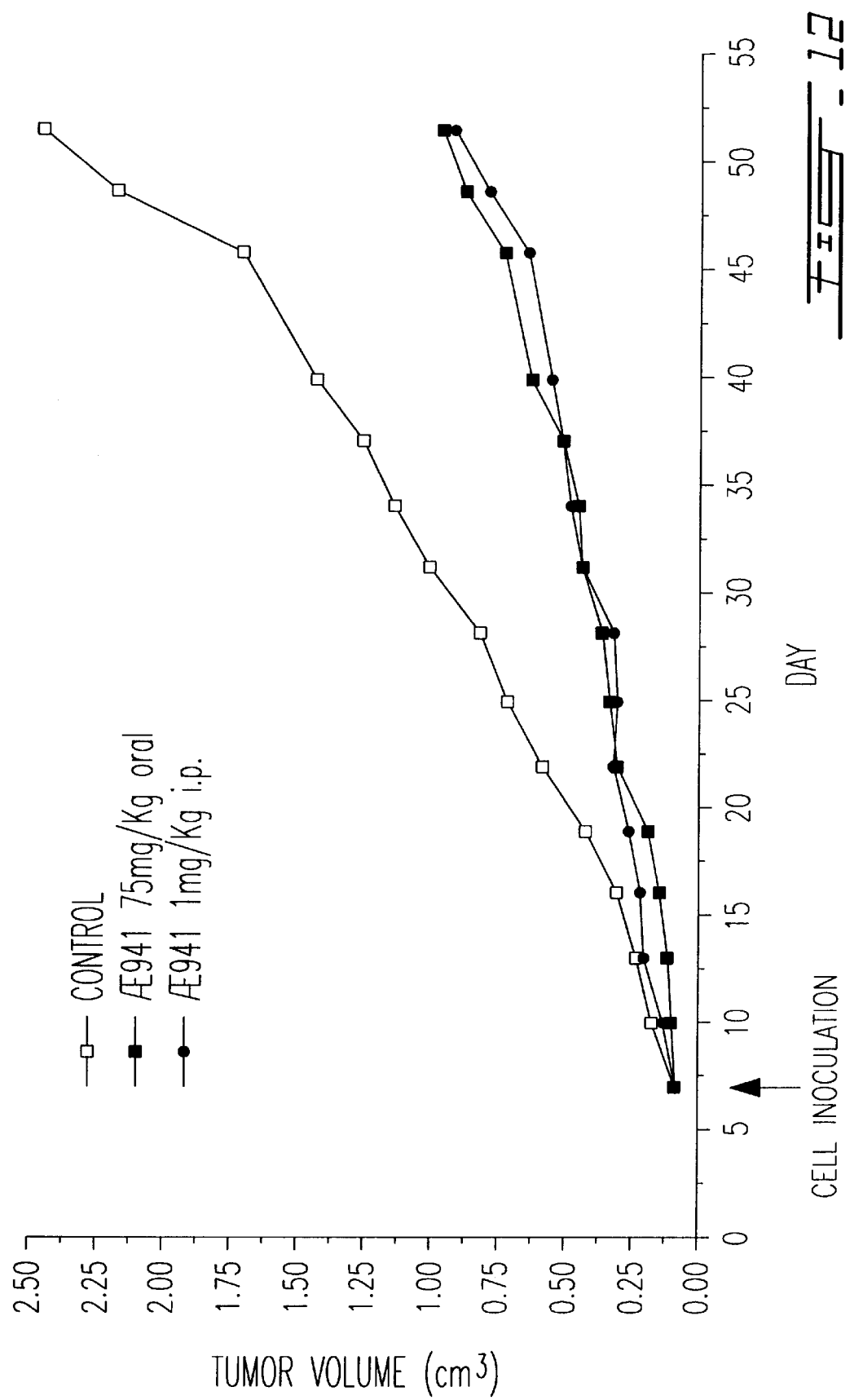
FIG. 12 shows that intraperitoneal administration of the liquid cartilage extract can increase significantly the efficacy of the product to inhibit tumoral growth.

Finally intraperitoneal administration of the liquid extract decreased drastically (75×) the maximal efficacy dose for inhibition of tumor growth (FIG. 12).

c. Toxicity: With all treatments there was no loss in body weight or liquid extract-related death. There were no symptoms or behaviour changes observed with daily examination of mice during the treatment period. At the end of the treatment, mice were sacrificed and the gross morphology of all organs was analyzed by a certified pathologist; no abnormality was detected. Blood analyses did not show any sign of abnormality.

d. Histopathology: Tumor histopathology did not reveal any gross changes between tumor from placebo- or liquid extract-treated mice. The extent of tumor viability was quite high in all groups. Analyses of various organs (lung, liver, kidney, pancreas, stomach, intestine, ovary, breast, brain, and heart) did not reveal any specific alteration that can be related to the liquid extract.

Mouse hypersensitivity model (CHS):

a. Description of the test system: Dinitrofluorobenzene (DNFB) is a powerful skin irritant that can induce a strong inflammatory reaction in BALB/C mice. At day 0, 10 mice were sensitized by painting their belly with DNFB. Mice were challenged on the right ear by painting 10 μl of DNFB 5 days after sensitization. Ear swelling was measured over several postexposure times as an index of tissue irritation.

The liquid cartilage extract was tested to examine whether it could reduce the inflammation response to DNFB in mouse. Vehicle alone (0.2 ml of a saline solution; 5 mice) or the liquid extract (0.2 ml of liquid-extract containing 20 mg/ml of dry weight; 5 mice) were administrated orally for 3 consecutive days before sensitization and the 4 following days.

b. Anti-hypersensitivity activity: One day after ear challenging, mice treated with the vehicle alone showed ear swelling to 8.2 mm thick. Interestingly, mice treated with cartilage liquid extract showed ear swelling of only 2.8 mm. The statistical significance of these data has a p value<0.001. These results demonstrate that liquid cartilage extract is a powerful inflammatory inhibitor.

Obtention of Liquid Fractions Containing Active Molecules

In vitro assays:

Tumoral cell lines:

a. Preparation of test-system: Shark cartilage was harvested and processed the same as described above. After centrifugation, the pellet was discarded and the supernatant was ultrafiltrated as described, up to the sterile filtration on 0.22 µm filter. The so obtained liquid extract was further fractionated by different methods. Tumoral cell lines were grown as descibed in above section.

b. FPLC conditions: Column: Hiload 26 mm×60 cm Sephacryl S-300. FPLC system: from Pharmacia. All samples were filtered on 0.22 µm filter before loading on the column. The elution buffer was phosphate buffer saline (PBS) filtered and degazed during 15 minutes. The volume of the loaded sample was usually 3.2 ml (could be up to 13 ml). The flow rate was 1 ml/minute. Fractions of 10 ml were collected. The eluted compounds were detected by their U.V. absorbance (280 nm). A calibration chart was obtained by using the MW-GF-1000 calibration kit from Sigma, this calibration sample having the same volume as the loaded sample to analyse (3.2 ml). The elution volume of a sample was deduced from the plotting of the molecular weight of the compounds of the calibration kit versus their elution volume to which was subtracted the void volume of the column. The void volume was obtained by injecting dextran blue (M.W.= 2,000,000).

The fractions were tested on ZR75-1 cells for their activity. The fractions of interest were identified and their characteristics were corroborated by further study (hereinbelow).

Additional characterization of the active components of the permeate was conducted on Rotofor (Biorad 170-2950; see isoelectrofocalization below) and on Amicon filters of different cut-off values to obtain fractions of molecular weight between 10–30 kDa, 30–100 kDa and over 100 kDa.

c. Isoelectro focalization conditions: A preparation of shark cartilage liquid extract (46 ml of permeate 1 Kg/L) was dialysed overnight against 4 liters of pure water containing 5% glycerin at 4° C. using a membrane Spectra pore #7 MWCO 3500 kDa (Spectrum 132110). The dialyzed solution was mixed with 2.75 ml of ampholytes (Pharmacia #80-1125-87) pH 3.5–10.0 and 0.5 g CHAPS (Sigma C3023; 3-[(3-Cholamidopropyl)-dimethylammonio]-1-propane-sulfonate). The volume was completed to 55 ml with pure water. The solution was loaded on Rotofor. Isoelectrofocalization was conducted at 4° C., at a constant power of 12 watts (3000 xi power supply Biorad 165-0554), under constant water circulation for insuring maintenance of the temperature. At the beginning of the separation, the voltage was 380 volts and the amperage 31 mA. When the amperage was stabilized (at 14 mA), the voltage read 870 volts. The isoelectrofocalization was stopped and 20 fractions were collected.

| FRACTION | VOLUME (ml) | pH |
|---|---|---|
| 1 | 3.7 | 3.56 |
| 2 | 2.1 | 4.01 |
| 3 | 2.2 | 4.18 |
| 4 | 2.3 | 4.31 |
| 5 | 2.2 | 4.63 |
| 6 | 2.1 | 5.03 |
| 7 | 2.5 | 5.30 |
| 8 | 2;1 | 5.50 |
| 9 | 2.4 | 5.81 |
| 10 | 2.5 | 6.26 |
| 11 | 2.3 | 7.00 |
| 12 | 2.4 | 7.29 |
| 13 | 2.4 | 7.64 |
| 14 | 2.5 | 7.94 |
| 15 | 2.3 | 8.32 |
| 16 | 2.5 | 8.62 |
| 17 | 2.4 | 8.94 |
| 18 | 2.9 | 9.30 |

-continued

| FRACTION | VOLUME (ml) | pH |
|---|---|---|
| 19 | 3.1 | 9.88 |
| 20 | 3.6 | 10.71 |

The identification of these proteins was made by estimating their molecular weight on an electrophoresis gel (Laemmli, U.K. (1970) Nature (Lond.) 227: 680).

Figure 13A:
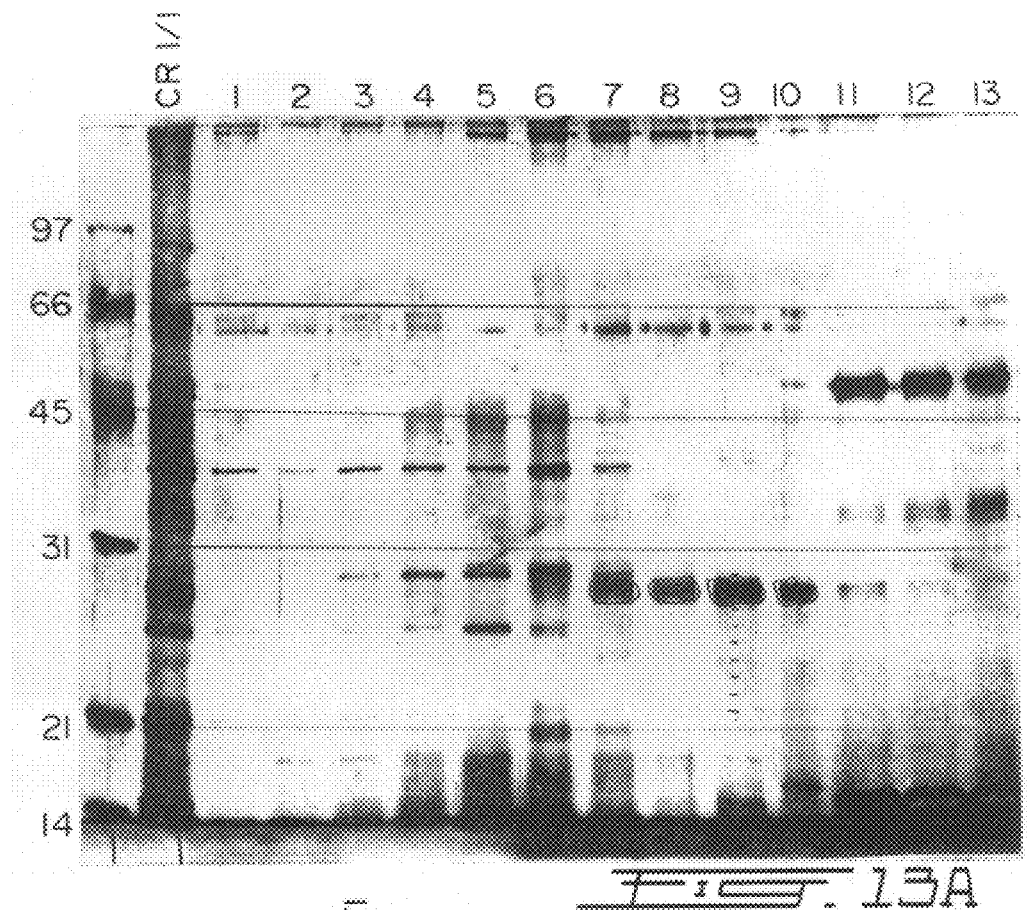
FIGS. 13a) and b) represent the electrophoretic profile in non-denaturing conditions of liquid fractions separated on Rotofor; molecular weight markers appear at the left followed by a sample of liquid extract before fractionation, for comparison with the isolated fractions.
Figure 13B:
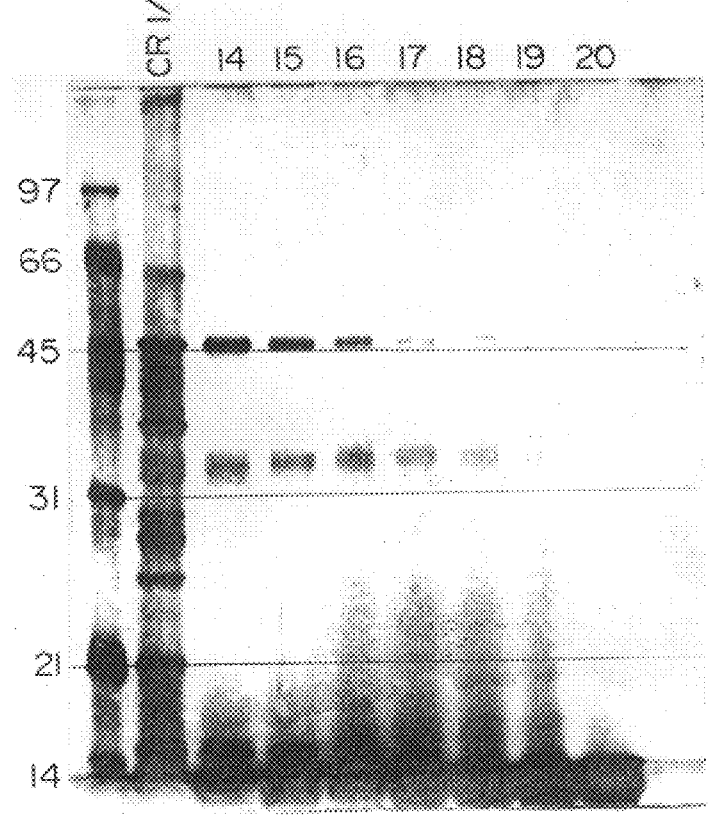

These fractions were four-fold diluted with a loading buffer (see Laemmli) and 8 µL aliquots were submitted to electrophoresis in non-reducing conditions. FIG. 13 shows the electrophoretic profile of each fraction and of the material before isoelectro-focalization.

All the fractions were sterile-bottled under a laminar flow hood by passing them through a sterile Millipack-60 filter having a porosity of 0.22 µm.

d. Inhibitory activity on tumoral cells: The protein content of the fractions was evaluated by the Lowry dosage method. Solutions of 1 Kg/2 L (expressed as the crude cartilage weight per liter of permeate) were tested on ZR75-1 cells at different concentrations in culture medium. The results are summarized as follows:

1st test: Tests performed on Rotofor fractions (the permeate was concentrated by evaporation). Protein identification:

| Fractions Identified | Isoelectric Point | Median Value | Molecular Weight |
|---|---|---|---|
| 7-8-9-10 | 5.30 to 6.26 | 5.78 | 29 +/− 1 kDa |
| 7-8-9 | 5.30 to 6.26 | 5.68 | 60 +/− 1 kDa |
| 12-13-14 | 7.29 to 7.94 | 7.62 | 48 +/− 1 kDa |
| 13-14 | 7.64 to 7.94 | 7.79 | 35 +/− 1 kDa |

2nd Test performed on FPLC fractions (the permeate was concentrated by evaporation):

| Fractions | Molecular Weight |
|---|---|
| 6 and 7 | 0.1–2.5 kDa |

3rd test performed on 100 µl fractions obtained on Amicon molecular filters:

| Concentration tested | Molecular Weight | Inhibition of ZR75-1 Cell Cultures |
|---|---|---|
| 100 µg/ml | MW > 100 kDa | 64% |
| 100 µg/ml | 30 kDa < MW < 100 kDa | 114% |
| 100 µg/ml | 10 kDa < MW < 30 kDa | 127% |
| 400 µg/ml | MW < 10 kDa | 149% |

FPLC fractions 6 and 7 contain active components of a molecular weight: 0.1 to 2.5 kDa.

The hypoplasiant effect of the fractions can be up to 33 000 times higher than the one observed with the lyophilizate.

e. Further identification of the active components of the eluate: The active fractions (tested on ZR75-1 cells) are retrieved in the following range of molecular weight, determined by another type of purification starting with the same permeate (1 Kg/L) on a 10 mm diameter×30 cm length Superose-12 column using the FPLC and rotofor procedures described above. A flow rate of 1 ml/minute was selected. 45 fractions of 1 ml were collected.

| Fractions 20–21 | activity in fractions corresponding to a molecular weight of 70 to 120 kDa |
| --- | --- |
| Fraction 22 | activity in fractions corresponding to a molecular weight of 60 to 70 kDa |
| Fraction 29–32 | activity in fractions corresponding to a molecular weight of 35 to 46 kDa |
| Fraction 34–35 | activity in fractions corresponding to a molecular weight of 29 kDa |
| Fraction 38–39 | activity in fractions corresponding to a molecular weight of 0 to 2.5 kDa |

Collaaenase assay:

a. HPLC chromatography: A 980 ml sample of liquid extract (DUP) was filtered through a 10 kDa cutoff membrane in a tangential flow ultrafiltration unit (PELLICON, Millipore). The unit was rinsed first with 1 L of water. Final yields were 480 ml of >10 kDa fraction and 1.8 L of <10 kDa fraction. The <10 kDa was concentrated by cold-finger evaporation to 180 ml (<10-10×). Eight times 100 μl aliquots of <10-10× were loaded onto CDC-S Hexyl, 5 μm HPLC column (25×0.94 cm) and eluted first with 100% $H_2O$ at 4 ml/min; then at 8.5 ml/min with 100% MeOH. Fractions were collected corresponding to $OD_{214}$ peaks.

Figure 14:
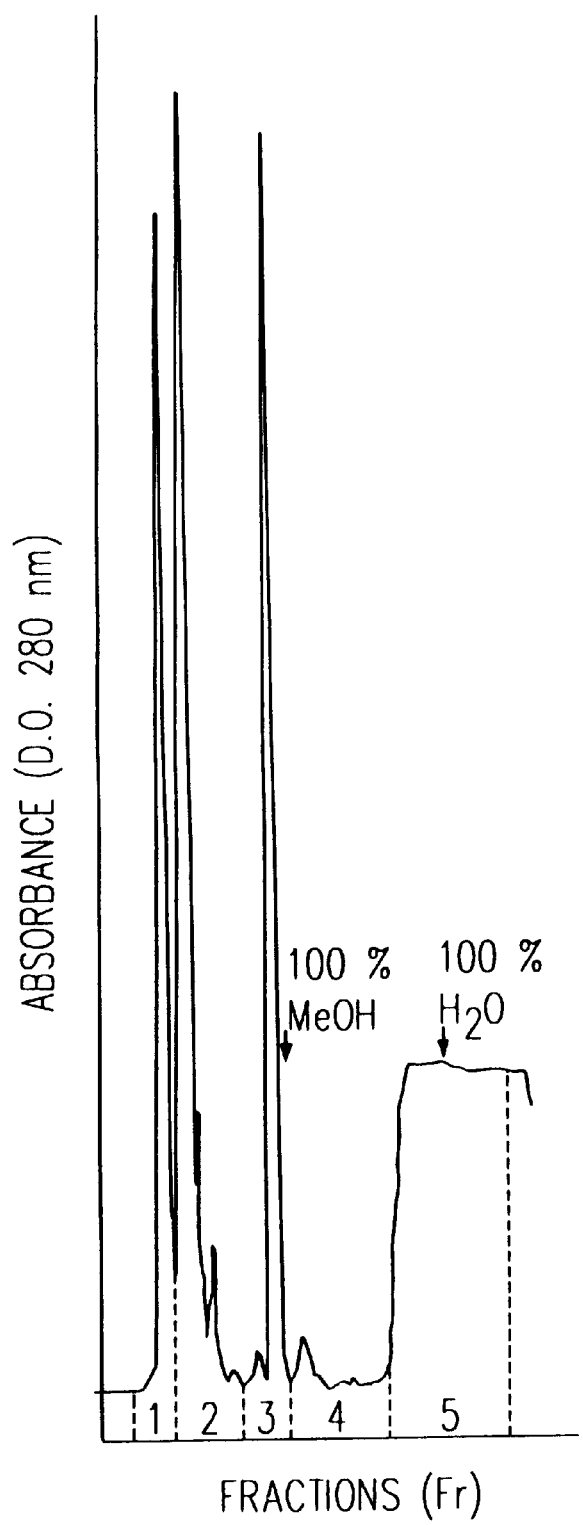
FIG 14 shows a HPLC migration pattern of a fraction of the total liquid extract of thin invention having molecular weight lower than 10,000 Da, which friction has been concentrated and separated in five sub-fractions.

Five fractions were collected (FIG. 14): Fr1, Fr2, Fr3, Fr4 and Fr5. The first three fractions include at least a major peak.

b. Anti-collagenolytic activity: The results show that Fr1 is the most active fraction to inhibit the collagenase; a lower level of activity is present in all other fractions: assay 1 see FIG. 14; assay 2 see the following table:

| SAMPLE | COLLAGEN STAINING | COLLAGEN FRAGMENT STAINING |
| --- | --- | --- |
| Collagen Only (C) | ++++ | – |
| C + Enz | + | +++ |
| C + Enz + EDTA | ++++ | – |
| C + Enz + DUP | + | ++ |
| C + Enz + Fr1 | ++++ | – |
| C + Enz + Fr2 | +++ | + |
| C + Enz + Fr3 | +++ | + |
| C + Enz + Fr4 | +++ | + |
| C + Enz + Fr5 | +++ | + |
| C + Enz + >10 kDa | + | +++ |

EDTA 40 mM inhibited collagenase. The total liquid extract DUP showed a low anti-collagenolytic activity. Fractions 1 to 5 were active; the most active was fraction 1. The fraction of a molecular weight higher than 10 kDa showed no significant inhibitory activity.

c. Further definition of the anti-collagenolytic factor: The liquid cartilage extract was fractionated using a tangential flow filtration apparatus and a 10 kDa filter (Pellicon, Millipore). The filtrate (<10 kDa fraction) was found to contain all of the anti-collagenase activity and was characterized further, as follows: The <10 kDa fraction was dialysed further using a 100 Da nominal molecular weight cut-off membrane (Spectra/Por_ CE (cellulose ester) MWCO: 100 Da, Cat# 131015). The anti-collagenolytic activity was recovered in the filtrate (<100 Da fraction). The <100 Da fraction was applied to a C8 reverse phase column (EM Science Lichroprep_ RP-8, Cat# 9242) and eluted with $H_2O$, then 60% methanol and finally by 100% methanol. The majority of the anti-collagenolytic activity (98%) was recovered in the $H_2O$ eluate, with 2% of the activity being eluted with 60% methanol.

In summary, anti-collagenolytic activity in the extract is due to a low molecular compound (or compounds) which can dialyse or pass through a Spectra/Por_ CE (cellulose ester) MWCO: 100 membrane and does not adsorb to a C8 reverse phase column matrix (Lichroprep_) when applied in $H_2O$.

Figure 15:
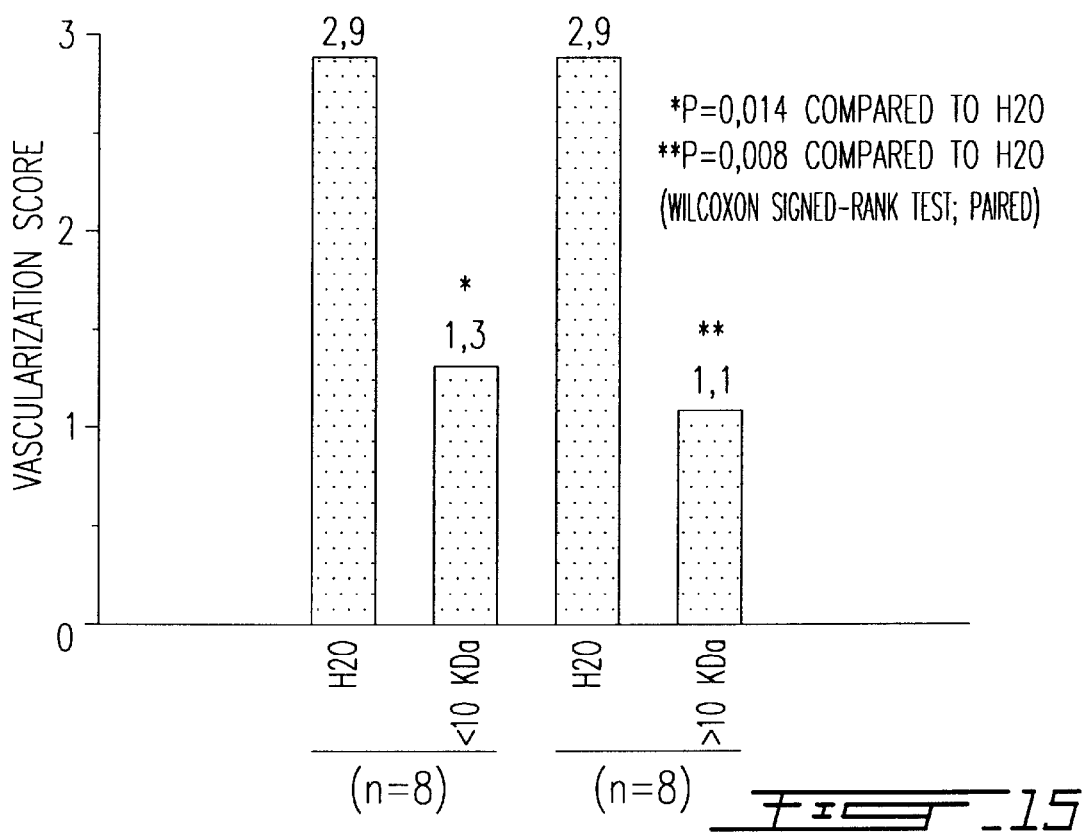
FIG. 15 shows the EVT results obtained with two fractions of liquid extract of shark cartilage of our invention (DOUP), one having molecular weight lower than 10,000 Da, the other one having molecules higher than 10,000 Da.

In vivo assay:

Embryonic vascularization test (EVT):

The liquid cartilage extract was fractionated using a tangential flow filtration apparatus and a 10 kDa filter (Pellicon, Millipore). The lower and higher than 10 kDa fractions of the liquid cartilage extract were tested in the same conditions. They were shown equally potent (FIG. 15) in inhibiting neovascularization. This contrast with the anti-collagenolytic activity which is not present in the fraction over 10 kDa.

a. Fraction <10 kDa: The anti-angiogenic factor in this fraction behaved as the anti-collagenolytic factor during the purification steps described above.

b. Fraction >10 kDa: The fraction was chromatographed on a gel permeation chromatography column (Sephacryl S-300, Pharmacia). A fraction (S300-4) having anti-angiogenic activity was characterized on SDS-PAGE. The active fraction (S300-4) had several protein bands having molecular weights of between approximately 8 and 18 kDa (compared with BioRad SDS-PAGE marker proteins). This fraction was further fractionated using anion exchange chromatography (Mono-Q, Pharmacia) using 25 mm Tris-HCl pH 8.0 and a 0 to 1.0M NaCl gradient. A fraction eluting at between 0.8–1.0M NaCl had high anti-angiogenic activity. Fractions eluting between 0.3–0.6M NaCl and 0.08–0.2M NaCl had lesser anti-angiogenic activity.

COMPARISON WITH PRIOR ART PRODUCTS

Definition of the Prior Art

Since we are not the first to find a great interest in cartilage extracts, we have verified the unique character of the shark cartilage liquid extract prepared by the present process in side-by-side comparison tests with two products described or deducible from the prior art, namely products prepared by the process of Balassa (U.S. Pat. No. 4,822,607) and Oikawa et al.(op. cit.).

Oikawa et al. describe a method by which two main fractions are obtained, one having molecules of molecular weights comprised between 1 and 10 kDa, the second having components heavier than 10 kDa. They assign anti-angiogenic properties only to the first fraction, the other being said devoid of any anti-angiogenic activity in CAM test. For adequate comparison of Oikawa's products, we have fractionated our total liquid extract in two corresponding fractions, and we retained the one having 0 to 10 kDa.

Since Balassa describes a process for extracting a total liquid extract, we have compared our total liquid cartilage extract (0 to 500 kDa) to the product prepared by reproducing Balassa's method, replacing the calve cartilage by shark cartilage as the starting material.

We assume that if Balassa and Oikawa describe a process equivalent to ours, the patterns obtained on FPLC, HPLC, and CZE should overlap substantially, and the same anti-angiogenic activity should be revealed on EVT. All samples were made to a final concentration of 12 μg/μL (dry weight/volume solution) prior to FPLC and HPLC chromatography. Oikawa's product was centrifuged and filtered prior to chromatography because it contained insoluble material.

Samples Preparation

Figure 18B:
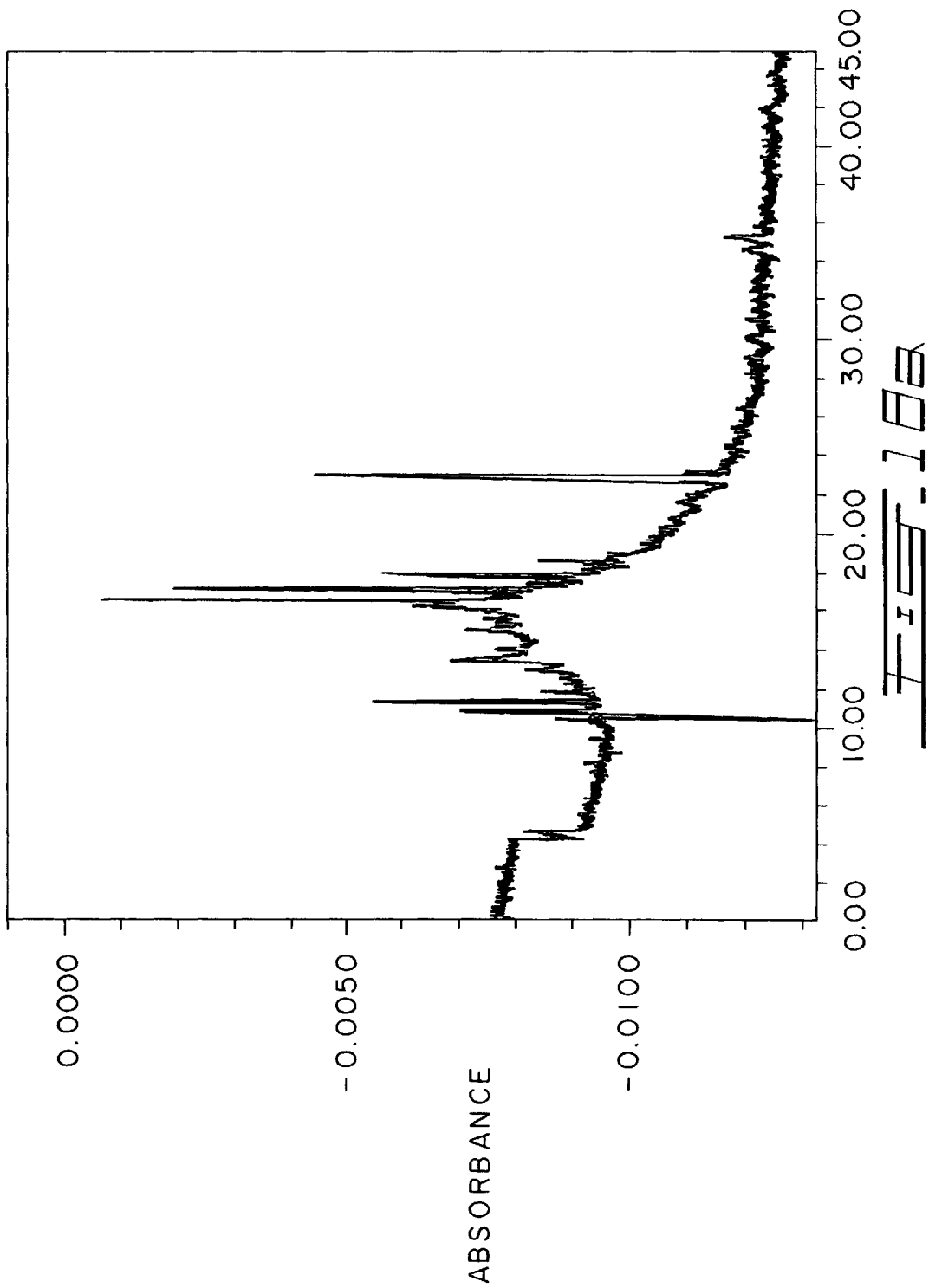
FIGS. 18a), b) and c) show a CZE comparison of the liquid extract of the same extracts defined in FIGS. 16b), a) and c), respectively. A=DUP; B=BAL; C=OIK.
Figure 18C:
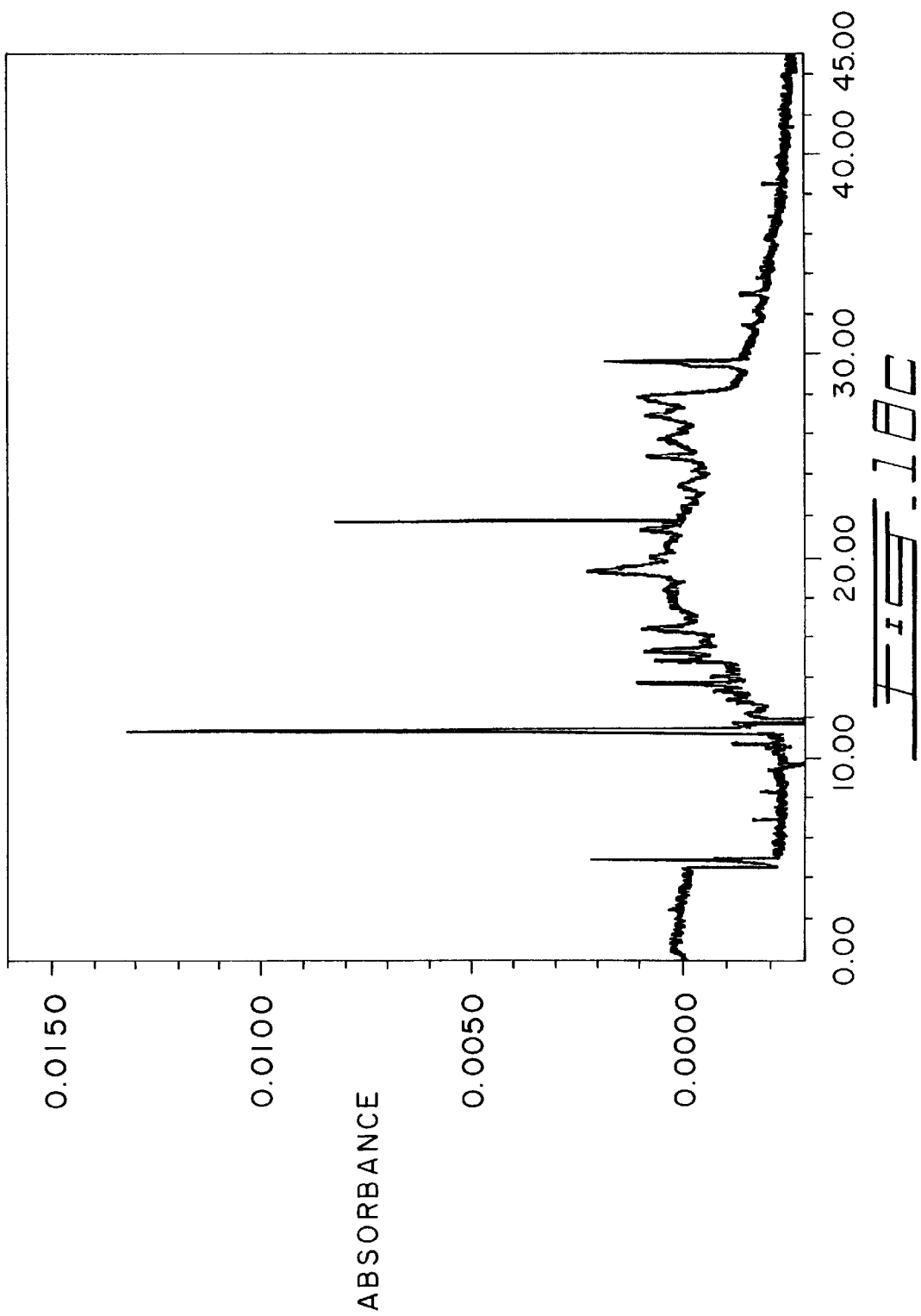

Shark cartilage samples extracted by the three methods were labelled (with estimated dry weight per volume of solution) as follows:

1) DUP is the preparation of the present invention fractionated to contain molecules between 0 to 500 kDa (12 µg/µl);

2) BAL is the preparation according to the recipe of Balassa et al. (12 µg/µl);

3) OIK is the preparation of fraction 3 according to Oikawa et al. All samples were made to a final concentration of 12 µg/µl (dry weight/volume) prior to any analysis. The OIK sample had a high amount of insoluble material which could be pelleted readily by centrifuging at 13,200 RPM or filtering through a 0.2 µm membrane. Removal by filtration of insoluble material was essential prior to FPLC, HPLC, and CZE (FIGS. 16, 17, 18).

FPLC Comparison

Conditions:

Superose 12 (Pharmacia); gel permeation column. Samples were run on a Superose 12 (10/30) gel permeation column with phosphate buffered saline (PBS) as eluent at a flow rate of 0.5 ml/min (chart speed=0.25 cm/min). A 100 µl aliquot of the concentration adjusted samples were filtered through a 0.2 µm membrane before injection. $OD_{280}$ was monitored.

The column was calibrated with the following standards (MW in Das): catalase (232,000), aldolase (158,000), albumin (56,000), ovalbumin (44,000), chymotrypsin (25,700), ribonuclease (13,700), insulin (5,700), insulin B chain (3500), insulin A chain (2500) bacitracin (1450), vitamin B-12 (1355). Molecular weights of the major peaks were calculated by the following equation: $Log_{10}MW=7.52-0.212\times RT$, where RT=elution volume in ml. $R^2=0.976$. Total column volume ($V_t$) was 21.93 ml as determined using cytidine (246 Da). Void volume ($V_o$) was determined to be 8.38 ml with blue dextran ($2\times10^6$ Da).

Results summary:

In FIG. 16a), our sample DUP had a first major peak (1) which eluted at 18.76 ml giving a molecular weight of about 3500 Da. Subsequent peaks at 22.7 (2) and 27.3 ml (3) were beyond the total column volume (21.93 ml, as determined by cytidine). These peaks appear to have some affinity for the column matrix.

Figure 16B:
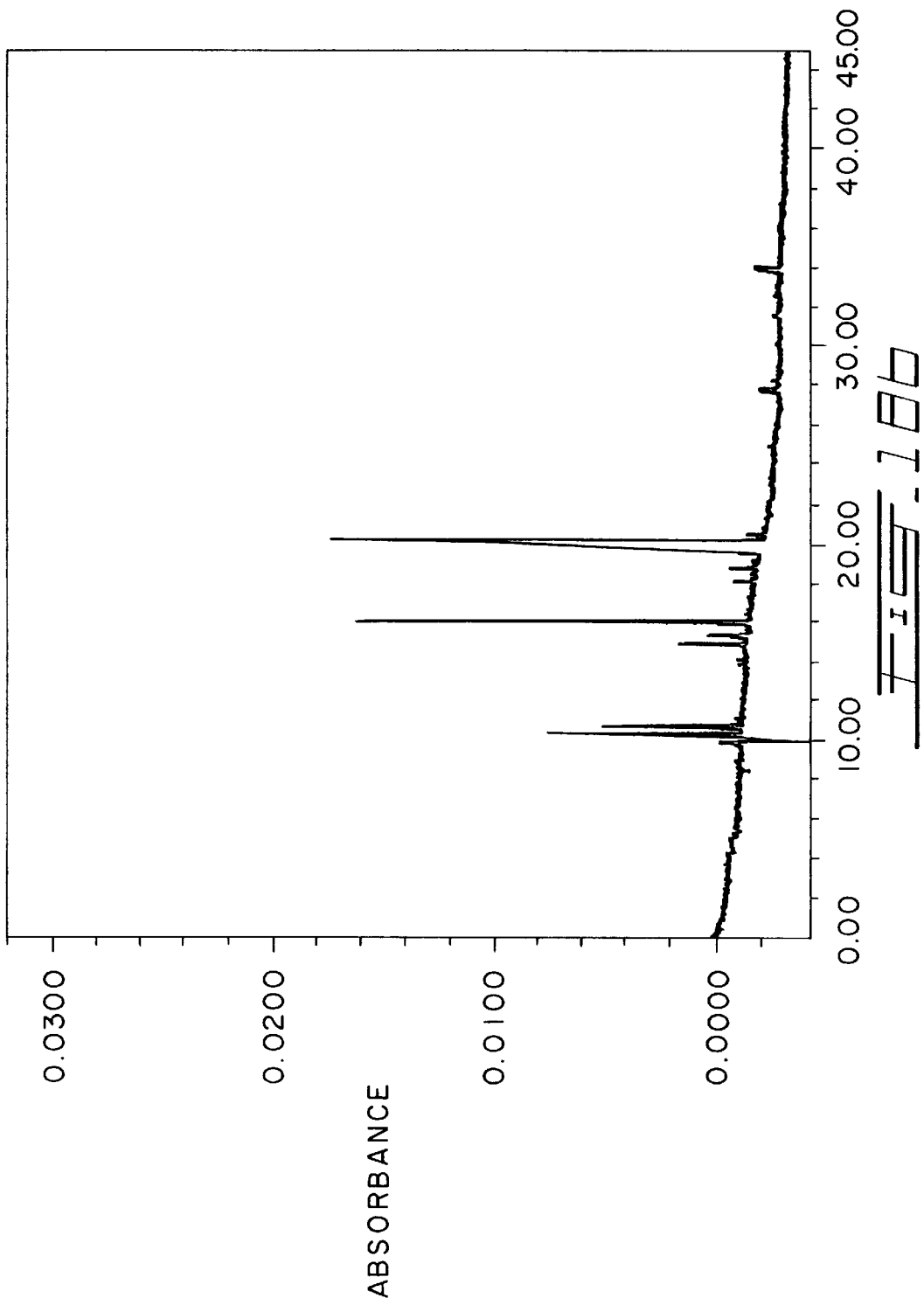
In FIGS. 16b) and c), BAL and OIK stand for extracts of the prior art, Balassa et al, and Oikawa et al., respectively.

In FIG. 16b), Balassa's sample BAL had a small peak (1) eluting near the $V_o$ of the column (8.4 ml), a peak (2) at 18.5 ml (4000 Da) and two peaks eluting after the $V_t$ (3) 22.6 min and (4) 28.2 ml.

In FIG. 16c), Oikawa's sample OIK also had a small peak (1) at the $V_o$, peak (2) at 18.9 ml (3300 Da), peak (3) at 21.5 ml (1000 Da) and small peak (4) at 27.3 ml.

In comparing the samples, it is notable that aside from the 3500 Da peak, that the major bands of the DUP sample were not observed at the same intensity in the other samples. The OIK sample did appear to have a small amount of the 27.3 ml peak. The BAL sample had a peak migrating at 28.2 ml which could correlate with one of the minor peaks in the DUP sample.

HPLC Comparison

Conditions:

CS-S-hexyl column 5 µm, 25×0.94 cm, CSC #059-085; reverse phase column.

Results summary:

For HPLC on a hexyl-reverse phase column, $OD_{210}$ and $OD_{280}$ were monitored simultaneously. 50 µl aliquots of centrifuged samples (all at 12 µg/µl) were loaded and eluted with 100% $H_2O$. Peaks for each chromatogram labelled according to $OD_{210}$ (eg. 1) and corresponding $OD_{280}$ peaks are noted by (eg. 1'). The $V_o$ of this column was 5.5 ml (1.4 min).

In FIG. 17a), DUP had 3 major peaks which were observed via $OD_{210}$ (1,2,3) and 2 minor peaks (4,5). Two side peaks were observed off of peak 1, labelled 1a and 1b. Significant $OD_{280}$ absorbances were associated peaks 1, 1a, 1b and 3. In comparison, the corresponding $OD_{280}$ absorption for peak 2 is much smaller relative to the $OD_{210}$.

In FIG. 17b) BAL showed more $OD_{210}$ peaks, but the intensities were lower relative to the DUP peaks. As far as overlap of peaks could give an indication of identity of molecules, only peaks 3 and 7 in the Balassa sample appear to correlate with the retention times of peaks in the DUP sample (peak 1a or 1b and peak 4, respectively).

In FIG. 17c), only three major peaks were observed (1,2,3) in OIK extract. Peaks 1 and 3 could correlate to peaks 1 and 3 of DUP sample but no side peaks of 1 were observed in the OIK chromatogram. The height of the peaks in the OIK sample were lower than the DUP. Therefore, FPLC and HPLC patterns are characteristic of distinguished products.

CZE Comparison

Conditions:

Apparatus: Beckman system (p/ace system 2050) with goal software (version 7.11 U); Capillary: Silice (TSPO 50375), 50 µm×97 cm; buffer: 2M formic acid; Coated solution, 5% p/v hexadimethrene bromide and 2% v/v ethylene glycol in water; Detector: UV (200 nm); Current: −30 kV; Injection: 0.5 psi, 20 seconds; Temperature: 22° C.

The capillary was conditionated wit 1M NaOH (20 psi, 20 min), water (20 psi, 10 min), Coated solution (20 psi, 20 min), and buffer (20 psi, 10 min). Then conditions were settled for a run: Buffer (20 psi, 2 min), sample injection (0.5 psi, 20 sec.), run (−30 kV, 45 min), 1M NaOH (20 psi, 3.5 min), water (20 psi, 3.5 min.), coated solution (20 psi, 4 min), and buffer (20 psi, 4 min.).

Each samples (BAL, DUP, OIK fraction 3) were resuspended at 16.5 mg/ml. pH of each solution was 7.1, 6.8, and 8.2 in BAL, DUP and OIK, respectively. NaCl concentration of each solution was 2.08, 4.37, and 0.71 mg/ml in BAL, DUP, and OIK, respectively.

Results summary:

The molecular profile of each sample (BAL, DUP, and OIK-3) is shown in FIG. 18. The comparison of DUP and BAL samples showed that the BAL sample was containing a larger proportion of peaks with a % area<1. BAL and DUP share the peaks at MT/EOF=1.06, 1.54, 1.59, 1.66, and 3.22. The peaks with the ratio of 1.06, 1.54, and 3.22 have a similar % area in BAL and DUP whereas peaks at ratio 1.59 is 8 times more intense than in BAL and the opposite is seen at the ratio 1.66.

DUP and OIK samples present a very different electrochromatogram. OIk has one major peak with several minor peaks. None of these peaks can be related to one of the DUP sample.

EVT Comparison

The anti-angiogenic potential of the samples DUP, BAL and OIK was analyzed on EVT (FIG. 19). No significant anti-angiogenic activity was retrieved in Balassa's extract. The DUP crude extract was compared to the fraction 3 in Oikawa OIK. Both DUP and OIK were almost equivalent. Oikawa et al. nevertheless taught away from the present invention since they mentioned that no activity was detectable in the fraction of molecular weight higher than 10 kDa, which is in contradiction with our results of FIG. 15.

Therefore, despite similarities between Balassa's and our processes, the products obtained by both processes are clearly not the same.

Amino Acid Content Comparison

The protein content of BAL, DUP and OIK samples (all of 16.5 mg/ml of dry weight) was measured by the method of Lowry; results show values of 3.31, 0.27, and 4.15 mg/ml for BAL, DUP, and OIK sample, respectively. The ratio of protein/dry weight is very different when DUP sample is compared to BAL and OIK.

Figure 20A:
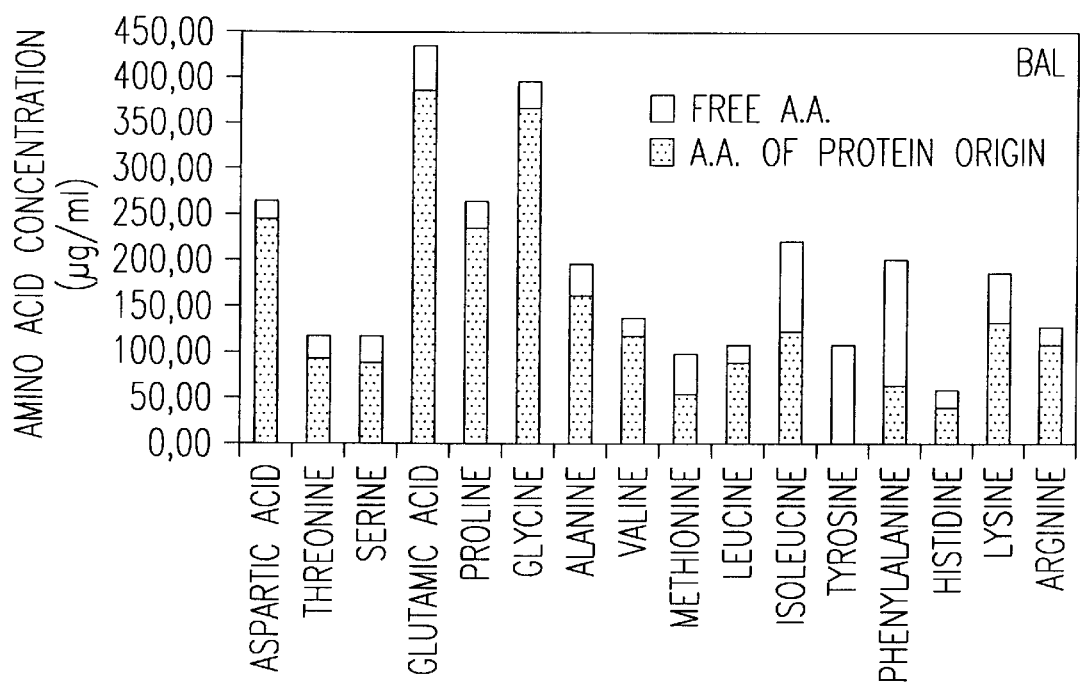
FIGS. 20a), b) and c) illustrate a comparison of the amino acid content of the same extracts defined in FIGS. 16b), a), and c), respectively.
Figure 20B:
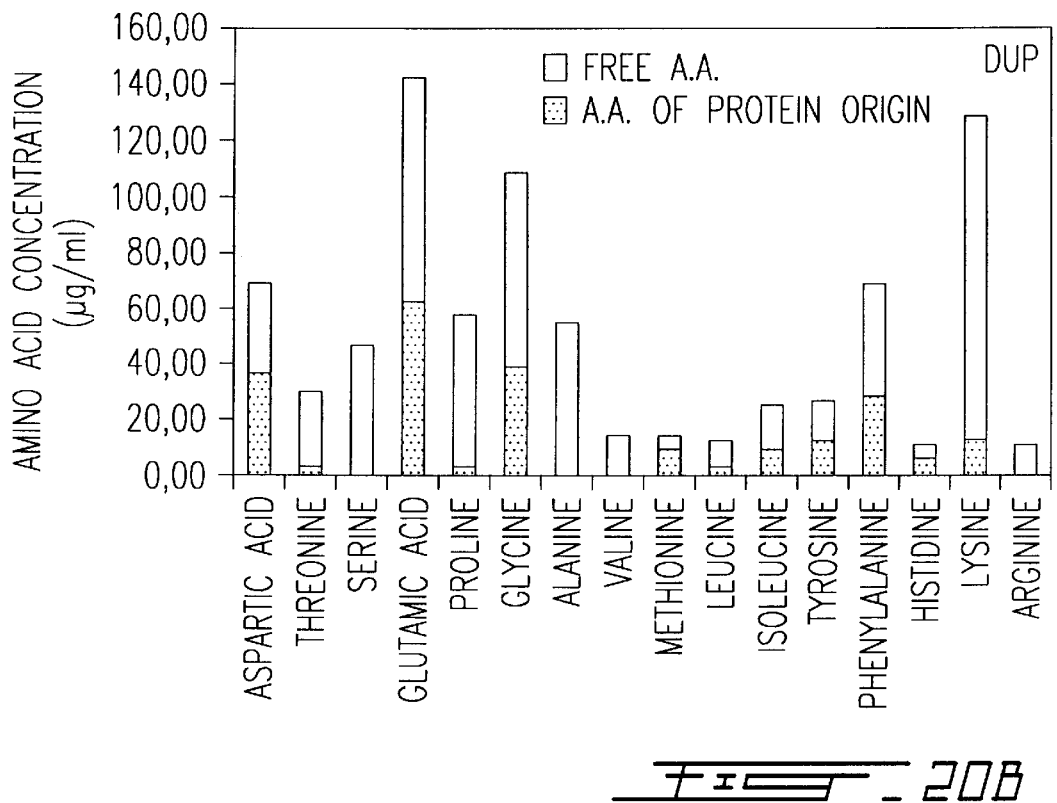
Figure 20C:
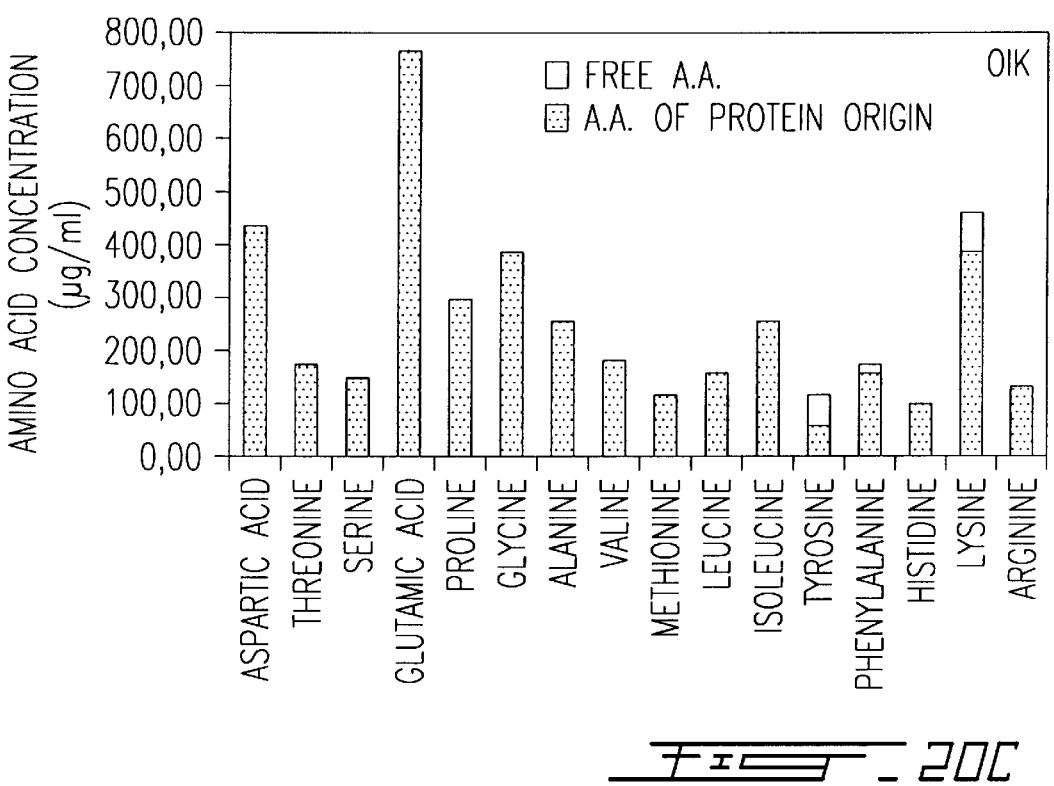
Figure 21A:
FIGS. 21a), b), c) and d) illustrate the significant improvement of the condition of two patients suffering of psoriasis, one with hyperkeratosis 21 a) and b), and the other one without hyperkeratosis 21 c) and d), when treated with a topical composition containing an effective amount of concentrated liquid cartilage extract (FIGS. 21b) and d) compared with their initial condition (FIGS. 21a) and c).
Figure 21B:
Figure 21C:
Figure 21D:

Analyses were performed to further analyse the amino acid content of each liquid cartilage preparation. FIG. 20 illustrates the proportion of each amino acid in BAL, DUP, and OIK samples. The proportion of free amino acids vary between each cartilage preparation: 23%, 73%, and 4% in BAL, DUP, and OIK samples, respectively. Obviously the proportion of amino acids from protein origin also vary between each cartilage preparation: 77%, 27%, and 86% in BAL, DUP, and OIK samples, respectively. See following table for raw data:

| Cartilage preparation | Free a.a. content ($\mu$g/ml) | a.a. from protein origin ($\mu$g/ml) |
|---|---|---|
| BAL | 675 | 2314 |
| DUP | 604 | 223 |
| OIK | 181 | 3910 |

Conclusions

The two prior art products (BAL, OIK) that have been compared to ours (DUP) are yet considered as classical processes to prepare cartilage extracts. The above results show that the present process (DUP) provides a product of unexpectedly good activity, as far as anti-angiogenic, anti-tumoral, anti-inflammatory, and anti-collagenolytic activities are concerned. We can assume that the present process has indeed succeeded in recovering a multiplicity of hydro-soluble inhibitory factors in one single extract.

Direct comparison of BAL, DUP and OIK molecular profiles and protein content demonstrated that each cartilage preparations have particular characteristics. Although they seem to share some constituants it is evident that their ratio one to another is different. This is particularly important considering that DUP is anti-tumoral when administrated orally at a dosage range below about 75 mg/Kg and looses gradually this effect at higher dosage. This result suggests that the amount of more than a single factor is critical in the DUP liquid cartilage extract. Therefore, different cartilage preparations like BAL, DUP and OIK may show very different biological properties since the proportion of each individual components vary between them.

CLINICAL TRIALS

Preparation of Liquid Extracts for Clinical Trials

Preliminary clinical trials were performed with shark cartilage liquid extract of the present invention. The liquid extract obtained after ultrafiltration was filtered of a millipore filter of a porosity of 0.22 $\mu$m. The microbial limit of the liquid extract was controled according to U.S. Pat. No. XXIII <61> standard. The liquid extract was distributed in 7 ml aliquotes (about 85 mg of proteins) in aseptic flasks, frozen at $-60°$ C. overnight and further stored at $-20°$ C. until utilization.

Anti-Angiogenic Effect

The liquid cartilage extract was used for treating angiogenesis-dependent diseases. Three different types representative of angiogenesis-dependent diseases were tested in the practice in human; the first type being cancer (prostate cancer), the second type being dermatological disorders (psoriasis), and the third type being arthritis (rheumatoid arthritis and osteoarthritis). The examples below will illustrate and indicate at least the anti-angiogenic activity of the liquid extract.

The results shown hereinbelow are very encouraging and are deemed predictive of the usefulness of the crude permeate and fractions thereof in the treatment of all angiogenesis-dependent diseases, and not only to the ones specifically tested. Insofar as a disease has an angiogenic component, it is deemed that the cartilage extract of the present invention will be effective in this respect provided that it enters a composition containing an effective amount thereof and that this composition is in a suitable form for proper administration. Therefore, it will be appreciated that the present invention is not limited to the following specific compositions for use in the treatment of angiogenic diseases, since the person skilled in the art would be able to derive numerous compositions wherein choice is guided by the mode of administration thereof and the targeted ill tissue. Compositions may be administered by different routes e.g. topical, oral, sublingual, rectal, intravenous, intramuscular, intraocular, intraperitoneal, by diffusion, etc.

Because of the fishy taste and smell of the cartilage extract, flavouring agents or fragrances may be added or other gallenic compositions (liposomes, encapsulation, patch, etc . . . ) can be designed to encourage patient's compliancy. The term "patient" is meant to designate human or animal patient.

Cancer:

One patient suffering of prostate cancer has added the liquid cartilage extract to its diet and shows significant health improvement since. An adenocarcinoma was diagnosed in 1986. At that time, radiotherapy was undertaken. In 1991, the PSA (Prostatic serum antigen) level was 138 $\mu$g/L, when the normal acceptable higher limit is 4 $\mu$g/L. The patient then underwent a completely different therapy by castration combined with anti-androgen therapy (EUFLEX). This treatment was efficient during three years, after which PSA level began to rise again. Since June 1994, this patient added the liquid cartilage extract to its diet (daily oral dose of about 75 mg of dry weight/7 ml of extract, equivalent to about 1–1.5 mg/kg of body weight/day). The PSA levels decreased gradually from 12 to below 4.0 $\mu$g/ml (normal limit), the last result being obtained in April 1996. This dose regimen would have to be modified at will in accordance with the route of administration, the bioavailability of the active ingredients and the desired aggressiveness with which the pathology is to be controlled. In this case, the liquid extract is probably absorbed in the gastro-intestinal tract in substantial proportions. One can rely upon the results obtained with DMBA-treated rats and inoculated mice (see above). At this time, the non-toxicity has been verified in rat, mouse (see above-examples), and monkey (data not shown).

Oral administration of the liquid extract in DMBA-treated rats and DA3-implanted mice suggest a dosage rate between 1 to 300 mg/kg of body weight, which presumably had a great contribution to the inhibition of tumor progression and tumoral vascularization in animal models. Intraperitoneal administration of the liquid extract in mice (DA3-model) demonstrated that the route of administration is important to obtain an effective dosage in inhibiting tumoral progression. This suggests that the dose rate of 1 mg/kg effective in the prostate cancer case could be lowered to almost 0.01 mg/kg if a parental administration route is selected. It is therefore assumed that a dose of about 0.01 to about 200 mg/Kg of body weight per day is an approximative reasonable range of median doses ($ED_{50}$) for treating cancer, at least partly by reducing or abolishing angiogenesis.

Several other patients added liquid cartilage extract to their diet (daily oral dose of about 75 mg of dry weight/7 ml of extract, equivalent to about 1–1.5 mg/kg of body weight/ day) in combination with more traditional therapies (surgery, chemotherapy, antihormonotherapy, etc.). Summary of some medical cases are provided in the following table. The results suggest that combination therapy with liquid cartilage extract may increase survival rate and quality of life of patients suffering of solid tumors.

| Type of cancer | Medical History |
| --- | --- |
| Urinary bladder | Urinary bladder 70-year old man; underwent ablative surgery of several lesions (2 cm and 1.5 cm) and added liquid cartilage extract to its diet; no residual carcinoma since 09/94. |
| Ovarian adenocarcinoma | 47-year old woman; lesions of 15 cm (right), 11 cm (left) and several 2 cm lesions; underwent surgery and chemotherapy in 1991; relapse treated by chemotherapy in 1992; second relapse treated by chemotherapy in 1993; addition of liquid cartilage extract to the diet in 1994; malignant neoplasm of reduced mass since. |
| Rhabdomyosarcoma | 63-year old man; infiltrating tumor of 11 cm in diameter (450 g); underwent surgery and chemotherapy; relapse treated by radiotherapy and addition of liquid cartilage extract to the diet; tumor showing necrosed tissue and stability since. |
| Pancreatic carcinoma liver metastases | 45-year old woman; pancreatic lesion (9 cm) + with liver metastases; chemotherapy and addition of liquid cartilage extract to the diet since; tumor regressed by 80% in 1994; tumor disappeared in 1995. |
| Mammary adenocarcinoma | 67-year old woman; surgery in 1978; relapse and lung metastases (1994); Megace and addition of liquid cartilage extract to the diet; since, partial regression of tumors in size (1.5 cm → 1 cm) and number (12 → 6). |

Psoriasis:

The following dermatological composition was made and tried to verify its efficacy in patients suffering of psoriasis:

EMULGADE CLB 29% (W/W)
20x crude permeate 69.5% (W/W)
GERMABEN II 1% (W/W), and
Lavandula Angustifolia 0.5% (W/W)

EMULGADE CLB, a mixture of stearate esters, fatty alcohols and nonionic emulsifiers (purchased from Henkel Canada Ltd.) was heated at 65–70° C. under agitation. Heating was stopped while the mixture was kept under agitation. When the mixture reached a temperature of 45° C., the essential oil Lavandula Augustifolia and the preservative agents GERMABEN II (diazonidyl urea 30%, methylparaben 11%, propylparaben 3% and propylene glycol 56%; purchased from Sutton Laboratories, NJ, U.S.A.) were added.

When the temperature of the mixture reached 30° C., the liquid cartilage extract was added. The composition so obtained was a smooth non-greasy cream; by varying the percentage of EMULGADE, other forms of various viscosity dermatological compositions can be obtained, in accordance with the manufacturer's directives (milk, lotion, ointment). Other vehicles or excipient might be used to obtain pastes, gels and any other form of transdermal preparation.

The above formulation was given twice daily during a period of twelve weeks to a panel of 9 patients (topical application) suffering of psoriasis that had been responsive to the conventional therapies tried but became refractory to them after a while. For this study, patients were selected for the similar and symmetrical extent of psoriasis on both side members. These trials were conducted in a double-blind fashion, neither the dermatologist nor the patients knowing which affected side was treated with the composition containing the cartilage extract and which one was treated with a control-composition. Remarkable improvement was observed in five patients whose psoriasis was not complicated by hyperkeratosis; for those having hyperkeratosis, the results were moderately good. Photographs of parts of two patients' bodies are shown in FIGS. 21. In FIG. 21 a and b, it is demonstrated that a patient affected by psoriasis with hyperkeratosis has nevertheless shown a very significant reduction of the erythema, associated with no prurit, after only one month of treatment. The hyperkeratosis remained, however, important. Photographs of the second patient suffering of psoriasis not complicated with hyperkeratosis (FIG. 21 c and d) showed a much better improvement after a three month-treatment. Since psoriasis appears to be a multifactorial disease, it is assumed that the response of the patients depends on the importance of the involvement of components like angiogenesis and inflammation in the establishment and in the perpetuation of this condition. The anti-angiogenic activity is indeed present in our extract, as shown in DMBA-treated rats (FIG. 5), endothelial cell proliferation (FIG. 7) and EVT (FIG. 10). The anti-inflammatory activity has also been verified (CHS model in mice). It is probable that better results might be obtained if this kind of formulation is complemented with other therapeutic agents addressing to other factors involved (keratolytic agents, additional anti-inflammatory agents, antihistaminics, immunosuppressors, etc.).

This complementation may take the form of amending the formulation to include an effective amount of a keratolytic agent, for example. It could also be achieved by the separate administration of such a complementary therapeutic agent, concurrently or in alternation with the application of the present topical formulation. Furthermore, the complementary medication does not need to be administered by the same route.

The above formulation has shown no systemic effect (the effect being limited to the treated areas) and no secondary effect despite the high proportions in liquid cartilage extract.

Arthritis:

Patients suffering of arthritis have tried on a voluntary basis one to two units of 7 ml total liquid extract per day for several months. These patients saw their condition improved gradually by recovery of joint function, diminution of pain and inflammation (up to about 60%). Since arthritis has angiogenic and inflammatory components, the above effect can be attributed to anti-angiogenic and anti-inflammatory activities of the cartilage extract.

A pilot clinical study was then conducted by a group of specialists in rheumatology. Seven voluntary and enlightened subjects aged between 39 and 60 years of age and suffering from rheumatoid arthritis enroled in the study. Diagnosis was established based on the classification criterias in the revised edition of the American Rheumatism Association's (Arnett, F. C. et al., 1988, Arthritis & Rheumatism, vol. 31, 315–325).

The treatment lasted 30 days and consisted in ingesting a daily dose of 21 ml of liquid shark cartilage extract (12 mg/ml of dry weight). The efficacy of the treatment was determined with an articular index for the assessment of joint tenderness (Ritchie, D. M. et al., 1968, Quaterly J. Med, New Series XXXVII, vol. 147, 393–406). The index is based on the summation of a number of quantitative evaluations of the pain experienced by the patient when joints are subjected to firm pressure exerted over the articular margin or in some instances upon moving the joint. The results show that 4 patients out of 7 have improved when treated with the liquid cartilage extract (Table below), suggesting that the product may be useful in the treatment of rheumatoid arthritis or other conditions complicated by chronic inflammation.

| Patient | Age | Ritchie's INDEX | | |
|---|---|---|---|---|
| (no) | (years) | Day 0 | Day 30 | Improvement |
| 1 | 60 | 30 | 22 | Yes |
| 2 | 43 | 8 | 8 | No |
| 3 | 52 | 12 | 12 | No |
| 4 | 41 | 15 | 19 | No |
| 5 | 46 | 5 | 3 | Yes |
| 6 | 39 | 6 | 2 | Yes |
| 7 | 55 | 14 | 7 | Yes |

Spider veins:

A total of 16 panelists were recruited for the study. The panelists had visible but not excessive telangiectasia on the face. The panel was divided in two groups of 8 each. Group A was provided with a cholesterol liposomal base containing 5% liquid cartilage extract while the second group (B) was provided with the cholesterol liposomal base alone. The products were used on the full face, twice a day for 3 months. A fiber optic surface microscope was used to obtain images of a minimal of 4 sites of the face showing spider veins. The images were analyzed for grey values via the Zeiss Ibas Image Analyzer. Integrated Optical Density (IOD) was calculated for each site for each panelist. The four sites on each panelist were averaged for each time point.

Figure 22:
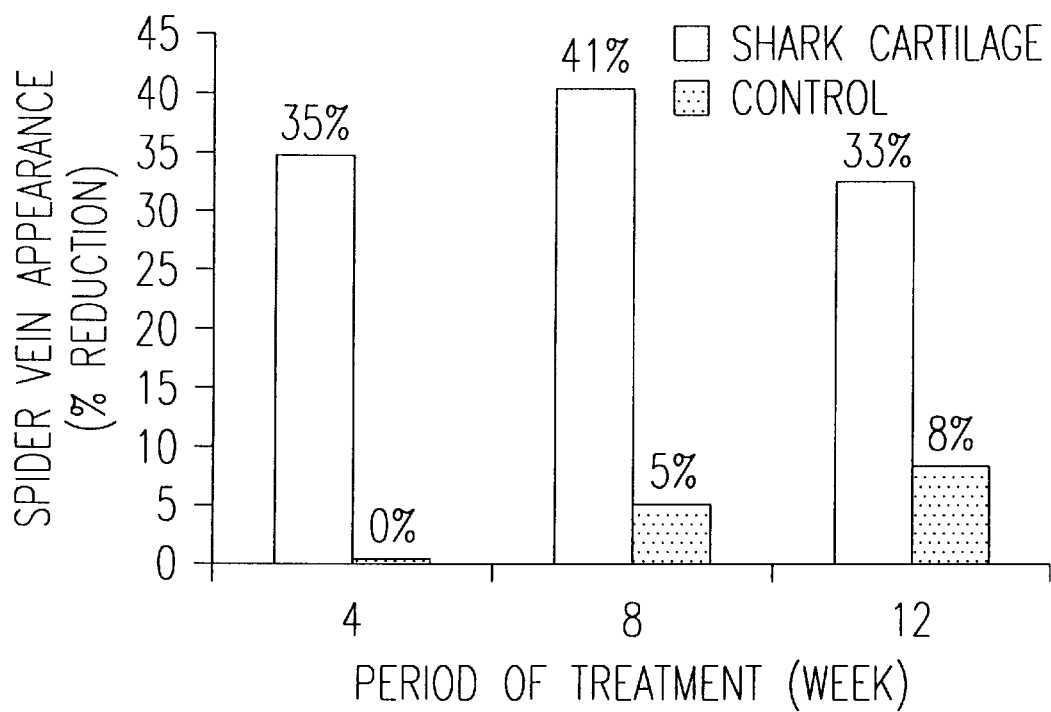
FIG. 22 shows the improvement of the appearance of spider veins in the visage of humans treated with liquid cartilage extract.

The results show there was a 35% decrease in the IOD after 4 weeks and this effect maintained for the course of the study (FIG. 22). The empty cholesterol liposomal base exhibited a background improvement of 5% and 8% after 8 and 12 week use, respectively.

Peri-orbital dark circles:

Skin coloration is not entirely due to the presence or absence of melanin, but also blood supply and plasma contents. When the blood flow is sluggish and greater amounts of oxygen are removed for metabolism, the skin appears bluish in color. These color differences are exaggerated in the eye area because of the thinness of the skin (Oresajo et al. (1987) Cosmetics & Toiletries 102: 29–34). Vascular changes in the septa that are present under the eye can also exacerbate the appearance of dark circles. Dark circles around the eyes also appear due to fat deposition, edema under the eyelids and leakage of blood vessels around the eye area. Clinical study was designed to evaluate the effect of shark cartilage liquid extract on controlling angiogenesis around the eye area thereby reducing the appearance of peri-orbital dark circles.

A total of 18 female volunteers between the age of 18–65 participated in the study. The panelists exhibited distinct Dark circles around the eyes. All panelists were normal in health with no evidence of acute or chronic diseases including dermatologic or ophthalmologic problems.

Subjects exhibiting current sunburn, rashes, scratches, burn marks, etc., which might interfere with evaluation of test results were excluded from the study. Pregnant or lactating females were also excluded. The test site was devoid of warts, moles, sunburn, subtan, scars, and active dermal lesions observed upon observation.

The panel was divided in two groups, 10 in group A and 8 in group B, each corresponding to the vehicle containing 5% liquid cartilage extract or the vehicle alone, respectively. The panelists were provided with enough product to be applied around the eye area at least twice a day for 12 weeks. Measurements were obtained at baseline, and after 4, 8, and 12 weeks. At each visit photographs were obtained and analyzed via Image Analysis.

Figure 23:
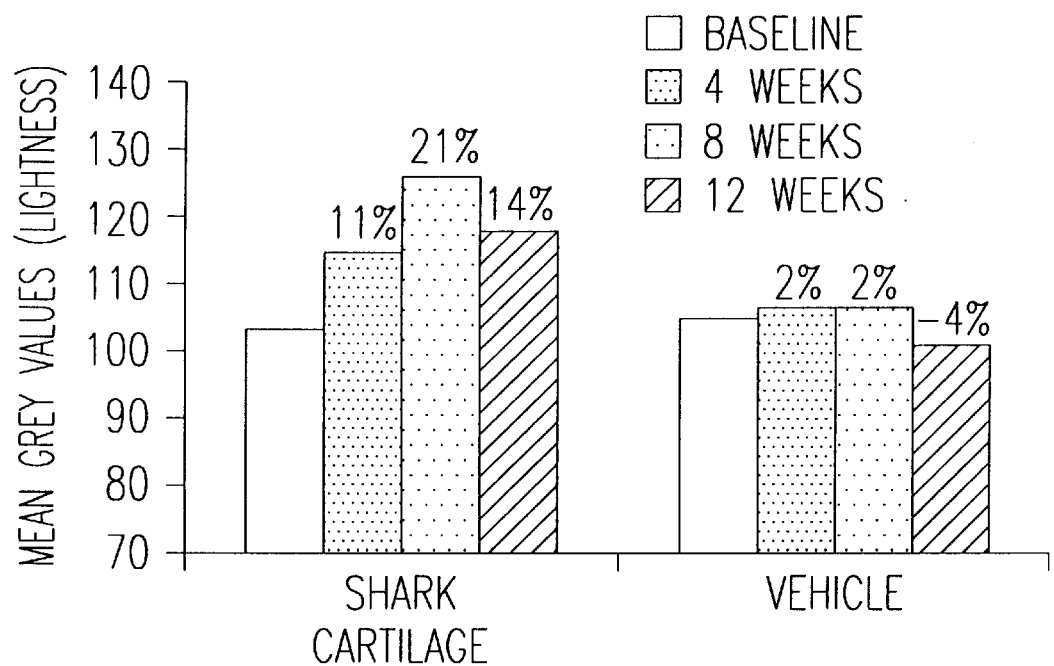
FIG. 23 shows the improvement of the appearance of dark circles around the eyes of humans treated with liquid cartilage extract.

Photographs were analyzed for the grey values which depict darkness/lightness of skin. It is clear that the group treated with liquid cartilage extract exhibited a good increase in grey values (which depicts lightening of dark coloration). After 4, 8, and 12 weeks there was 11%, 21%, and 14% lightening of the skin under the eye area of the group treated with the liquid cartilage extract. The group treated with the vehicle alone did not show any change (FIG. 23).

Varicose veins:

A total of 20 panelists completed the study. The panelists had visible but not excessive telangiectasia on the legs. The panel was divided in two groups, Group A (n=9) was provided a liquid cartilage extract containing cream while Group B (n=11) was provided a vehicle cream alone to be used on the full legs, twice a day for 3 months. A fiber optic microscope was used to obtain images of 2–4 sites of the legs showing varicose veins. The images were analyzed for grey values via the Zeiss Ibas analyzer. Integrated Optical Density (IOD) was calculated for each site for each panelist. All the sites on each panelist were averaged for each time point.

Figure 24:
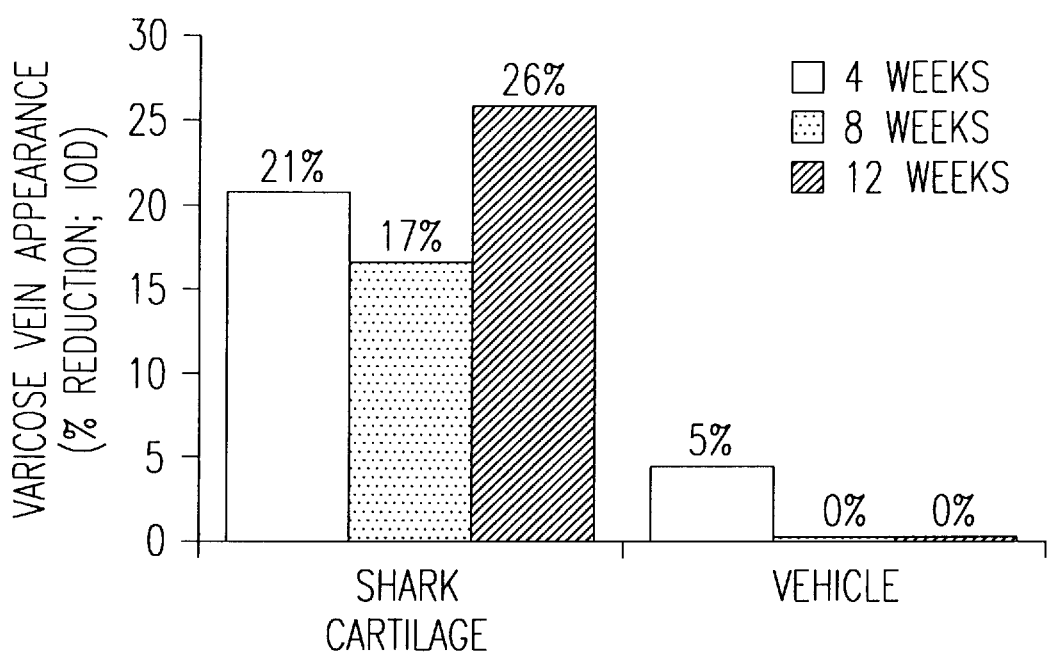
FIG. 24 shows the improvement of the appearance of varicose veins on the legs of humans treated with liquid cartilage extract.

Results are illustrated on FIG. 24. There was 21%, 17% and 26% decrease in the IOD after 4, 8 and 12 weeks of use, respectively. The control vehicle exhibited a background improvement of 5%, 0% and 0% after 4, 8 and 12 weeks of use, respectively.

Other potential clinical and veterinary applications:

Ophthalmology: A decrease in vision or blindness can be caused by a number of conditions characterized by abnormal blood vessel growth or neovascularization. These include corneal neovascularization (caused by chemical or physical irritation), corneal infection, corneal graft rejection, neovascular glaucoma, macular degeneration, herpes virus keratitis, and diabetic retinopathy. The liquid cartilage extract could act upon these clinical conditions by inhibiting the formation of new blood vessels, and by reducing telangiectasis and inflammation.

Wound repair: Wound repair involves a complex interaction between cells, biochemical mediators, extracellular matrix molecules, and the cellular microenvironment. After full-thickness wounding, granulation tissue (fibroblasts, capillaries, and inflammatory cells) first grows from the wound edge in a characteristic sequence. Fibroblasts begin to migrate into the wound space from connective tissue at the wound edge within 24 hours. As they move, fibroblasts produce matrix molecules (collagen and glycosaminoglycans), which form an extracellular matrix. The first capillary buds can be seen in the perfused microcirculation at the wound edge as early as 18 hours after wounding. These buds grow into the wound space and provide the new capillary network for the wound connective tissue. Fibroblast proliferation and migration and capillary growth continue as a unit until the wound space is completely filled with new tissue. Some wound repair conditions that are complicated by overexpression of granulation factors, such as hypertrophic scarring and the healing of the skin of badly burned person, could benefit of the administration of liquid cartilage extract (orally or topically) since decreasing the angiogenic process would slow down the process of wound healing.

Papuloscuamous skin disease: The beneficial effect of liquid cartilage extract on psoriasitic lesions suggests that other diseases having common characteristics could also profit of local or systemic administration of the liquid extract. The papulosquamous skin diseases are characterized by red to violaceous papules and plaques that result from thickening of the epidermis and/or underlying dermal inflammation and include psoriasis, Reiter's syndrome, pityriasis rosea, lichen planus, pityriasis rubra pilaris, secondary syphilis, mycosis fungoides, and ichthyosiform eruptions.

Alopecia: The ligature of small lateral arteries driving blood flow to the scalp has been successful to prevent hair loss caused by androgen overexposure. Local application of liquid cartilage extract on some region of the scalp could prevent hair loss by decreasing the vascular network and consequently the exposure to hormones.

Veterinary applications: Solid and/or liquid cartilage extracts may be administred to animals for the same therapeutical and cosmetical applications that have been described for humans.

Non-Anti-Angiogenic Effect

Acne:

Even though acne is not to the inventors' knowledge, classified as a disease or disorder having an angiogenic component, it was nevertheless tempting to test the liquid cartilage extract in patients so affected on the basis that the liquid extract is also anti-inflammatory. For experimenting the cartilage extract in patients affected by acne, the following gel formulation was made:

| |
|---|
| CARBOPOL 1.2% |
| Purified water 77.2% |
| NaOH 0.3% |
| PHENOXETOL 0.3% |
| TWEEN 80 0.3% |
| Liquid cartilage extract 20.0% |
| 40 × Aloes extract 0.5% |

Figure 25A:
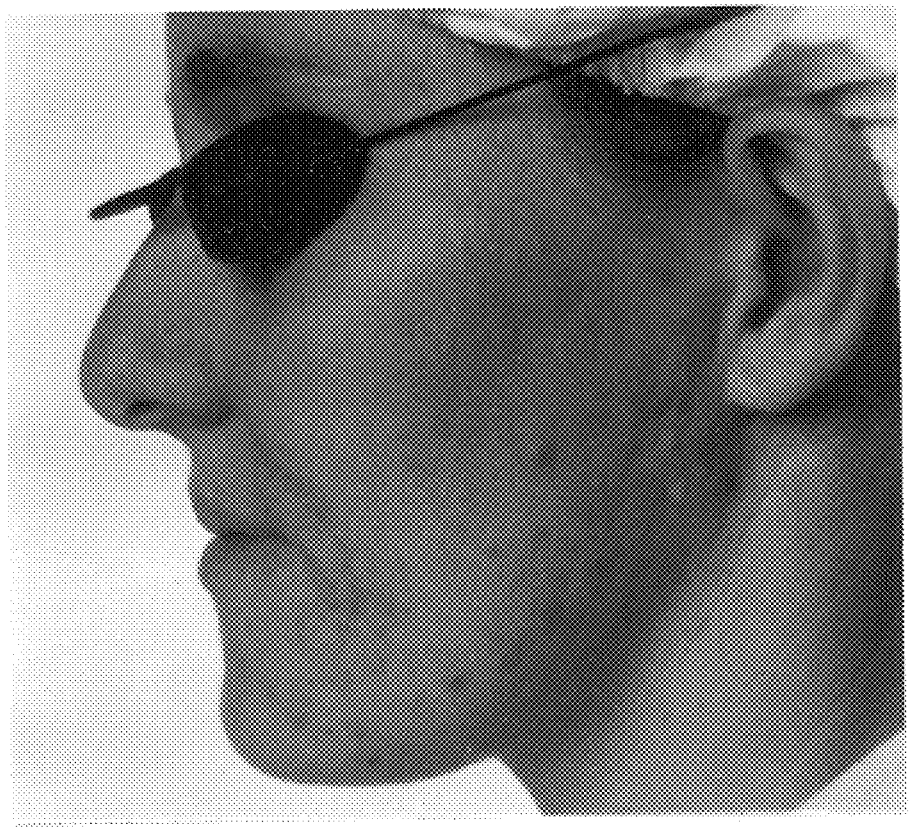
FIGS. 25a) and b) illustrate the significant improvement of the condition of a patient suffering of acne when treated with a topical composition containing an effective amount of liquid cartilage extract (FIG. 25b) compared with her initial condition (FIG. 25a).
Figure 25B:

The liquid cartilage extract contains 9–12 mg/ml of dry weight. This formulation shows a remarkable improvement of the aspect of the skin of patients affected by more or less severe forms of acne (inflammatory acne and kystic acne). FIG. 25 shows the significant improvement of the condition of a patient suffering of acne when treated with the topical liquid extract containing vehicle during 12 weeks.

These results may be due to an anti-angiogenic effect (thus revealing an angiogenic component in acne), or they may be due to active ingredients that have an effect other than anti-angiogenic (an anti-inflammatory effect, for example). All the results obtained in the above clinical trial show the great potential of the cartilage liquid extract in the treatment of angiogenesis-dependent and/or inflammatory diseases. The amount of cartilage extract as well as the formulation thereof may be varied at will to fulfil specific needs.

One can note that, on a proteic content basis, the topical and all other compositions may contain a wide range of doses of the cartilage extract. Among the three specific categories of cases tested, very different dosages and/or formulations have been used.

Skin irritancy:

Since angiogenesis is often associated to inflammation in numerous diseases, it would be desirable to assign each activity separately in the cartilage extract. In this regard, a skin irritation model wherein no angiogenesis is suspected to occur has been chosen to test the extract for its anti-inflammatory and soothing activity. Nine volunteers with a history of skin sensitivity to Balsam of Peru were chosen for the study. The test compounds were as follows:

1. 1× Shark cartilage 50% in D-MEM media
2. 1× Shark cartilage 20% in D-MEM media
3. 1× Shark cartilage 10% in D-MEM media
4. Cola nitida (Indena) 10% Hydro-alcohol 1:1.

Figure 26:
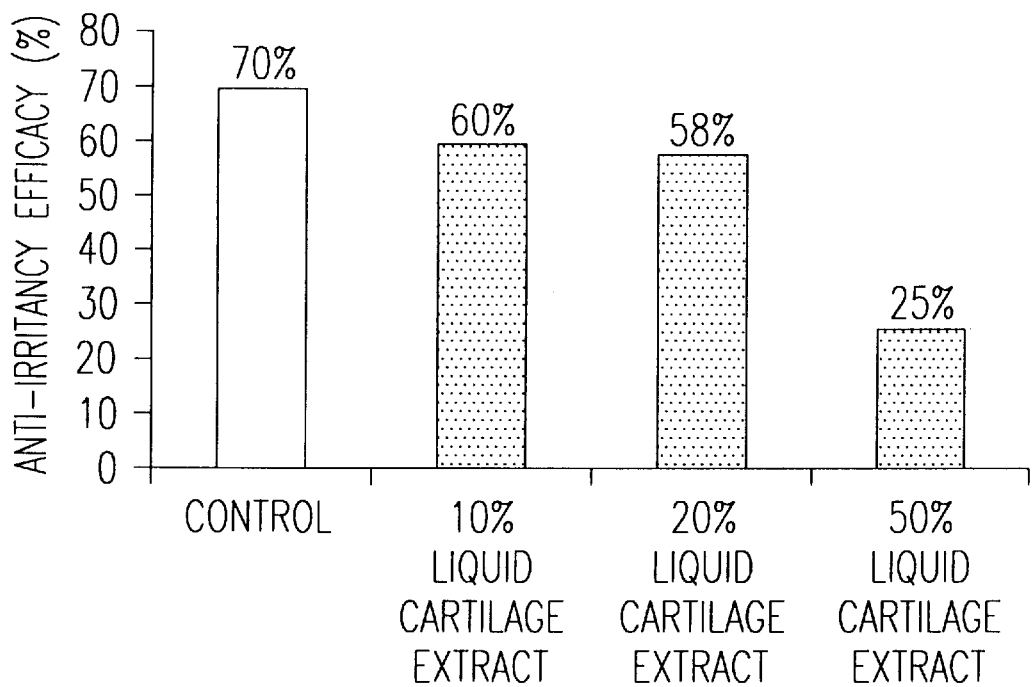
FIG. 26 shows the anti-inflammatory potential of the liquid cartilage extract on human skin.

The 4 test compounds were applied on the ventral forearms of the panelists. The material was allowed to absorb for twenty minutes and then Balsam of Peru, an irritant, was applied on the test sites. Skin irritation was measured in terms of increase in skin redness. The degree of redness was measured with a Minolta Chromameter and compared with the positive and negative controls. The positive control was the colour of skin treated with Balsam of Peru alone and the negative control was a skin site treated with cola solution and challenged like the test products. Statistical significance was calculated via two tailed probability T-test. FIG. 26 shows that cola at 10% was 70% active. Shark cartilage was 58% and 60% as anti-irritant at 20% and 10% concentrations, respectively. There was no dose-response effect. These results suggest that the cartilage extract contains anti-inflammatory and soothing activity which is remote from an anti-angiogenic effect.

Cancer:

A female patient 53 years old was diagnosed a large cell non-Hodgkin's lymphoma of the B type. CAT scan analysis revealed adenopathies around the carotid and the jugular vein (2.5 cm in diameter) and a voluminous adenopathy over the right renal hilus. The patient refused chemotherapy and added the liquid cartilage extract to her diet (October 1993)(daily oral dose of about 75 mg of dry weight/7 ml of extract, equivalent to about 1–1.5 mg/kg of body weight/day). Three months later (January 1994) CAT scan analysis revealed adenopathies in the neck completely resorbed. By November 1994 the abdominal adenopathy has decreased in volume by 75%. The disease is stable since and the patient feels in good health.

This result suggests that some non solid cancer may also respond to the anti-tumoral activity of the liquid cartilage extract.

Barrier protection of the skin:

A panel of six healthy volunteers participated in the study. The panelists received a cream containing the liquid cartilage extract to be applied on the right forearm and the vehicule only to be applied on the left forearm, twice a day for four weeks.

The panelists were female, ages 21–45, with no evidence of acute or chronic disease including dermatological or ophthalmological problems. Subjects exhibiting current sunburn, rashes, burn marks, etc., which might interfere with evaluation of test results, were excluded from the study. The test site was devoid of warts, nevi, moles, sunburn, suntan, scars and active dermal lesions observed upon examination. On the day of the test, the panelists were instructed to refrain from using any lotions, creams or other products on the face. During the course of measurements, the panelists were equilibrate for at least 30 minutes prior to testing in a controlled environment of 20–22° C. temperature and 40% relative humidity.

The test site was the right and left volar forearms. A small area (3.5 cm×7 cm) was marked on each arm and basal transepidermal water loss (TEWL) measurements were obtained from three sites within this area (Pinnagoda et al. (1990) Contact Dermatitis 22: 164–178; Grove (1994) in *The effects of aging in oral mucosa and skin,* Ed. Squier & Hill, CRC Press, pp 124–125).

A sticky (Tuck) tape was used to cover the test area and, after a firm stroke in both directions, the tape was peeled off (Elias (1993) J. Invest. Dermatol. 80: 044s–049s). A total of 5 strippings were obtained. TEWL was recorded again. Strippings followed by TEWL measurements were continued in groups of 5. The strippings were stopped when the TEWL approached 18 $G/M^2/Hr$. TEWL was measured again at the end of the last stripping sequence. The number of strippings required to damage the skin barrier was calculated by noting the number of maximum strippings for each arm, at each time point that exhibited a TEWL of 18 $G/M^2/Hr$ or more. The results were analyzed for statistical significance between treatment at various time points versus baseline using the one tailed rank coefficient Z test.

Figure 27:
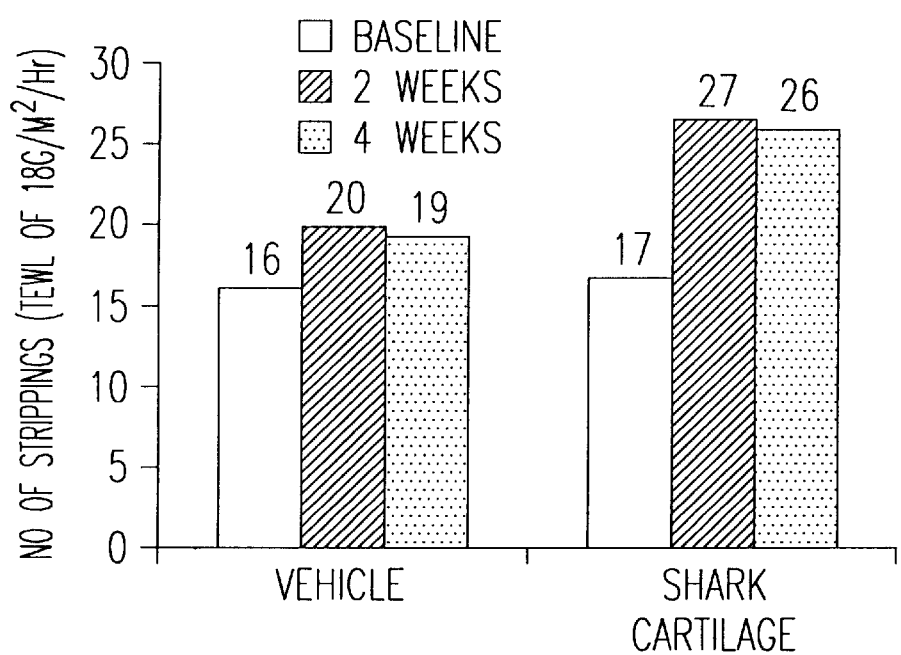
FIG. 27 shows the improvement of the barrier function of the skin of humans treated with liquid cartilage extract.

Vehicle treated arm did not appear to exhibit much improvement since only 26% and 21% more stripping was required to damage skin after 2 week and 4 week treatments, respectively. There was a significant improvement ($p<0.05$) in barrier condition of each of the panelists after treatment with liquid cartilage extract product for 2 and 4 weeks when 60% and 55% more strippings were required to disrupt skin barrier (FIG. 27).

Therefore, liquid cartilage extract has proven to be useful in strengthening skin barrier against physical damage.

Eczema:

The liquid cartilage extract was tested in beauty salon on the basis of its ability to decrease the the inflammatory lesions caused by eczema. The beautician applying the liquid extract-containing cream suffers since many years of chronic eczema in her hands. Interestingly, the uses of the cartilage-containing cream decreased significantly the expression of eczema in her hands. She is now using successfully the cartilage-containing cream to prevent the expression of eczema.

Warts:

A 36 years old female with a history of plantar warts was treated by a dermatologist for almost three years to control wart progression and associated pain. Among the treatments there was liquid Nitrogen, Salicilic acid (40%), Anaerobia, Nitric acid, and sulfuric acid. These treatment were generally every week for a duration of three months and the results were almost nil. In March 1996 she applied daily (5 minutes) the shark cartilage liquid extract directly on the warts; two weeks later a pink zone of new epidermis formed around the warts; the following week warts were gone. Therefore, this result suggests that the liquid cartilage extract may help in the treatment of warts.

Other potential clinical and veterinary applications:

Graft rejection: Inflammation is one of the major factor involved in the mortality of transplanted cells. Therefore, tissue graft could benefit from the anti-inflammatoty components present in our shark cartilage liquid extract.

Multiple sclerosis: The cause of multiple sclerosis are unknown. The tissue response has features of an immunopathologic process, with perivenular mononuclear cell infiltration and absence of any overt histopathologic evidence of an infection. Matrix metalloproteinases are important factors involved in inflammatory response. Since liquid cartilage extract is a powerful inhibitor of matrix metalloproteinases it may be useful in the treatment of multiple sclerosis.

Fibrosis: Current concepts suggest that fibrosis ressembles normal wound healing, but fail to terminate, leading to the replacement of normal tissue with scar. Most fibrotic reactions appear secondary to trauma, infection, inflammation or, for unknown reasons, may have a genetic component. Typically TGF-$\beta$ is overproduced and induces the proliferation of fibroblastic cells and the overproduction of collagen. Since an excessive deposition of collagen is the hallmark of fibrosis, we suggest that liquid cartilage extract which can delay the formation of granulation tissue could have long term benefits in suppressing fibrotic reactions.

Inflammatory bowel disease: The etiology of inflammatory bowel disease is unknown, but abnormal intestinal immunity is involved in the pathogenesis of Crohn's disease and ulcerative colitis. Mucosal mononuclear cells display altered antibody production, proliferation, cytotoxicity and cytokine synthesis (FGF, PDGF, EGF, TNF). Liquid cartilage extract has shown anti-inflammatory activity and then oral administration may prove to be helpful in the therapeutical treatment of inflammatory bowel disease.

Heart diseases: Endothelial dysfunction of coronary resistance vessels can account for abnormalities of the coronary microvasculature and possibly myocardial ischemia and chest pain. At a cellular level, endothelial dysfunction is associated with reduced expression of nitric oxide (NO), an endothelium-derived relaxing factor. NO synthesis allows the vascular system to maintain a state of vasodilatation thereby regulating arterial pressure. A deficit in endogenous synthesis of NO contributes to such conditions as arterial hypertension, pulmonary hypertension and heart disease. We have preliminary results from cultured endothelial cells that the liquid cartilage extract increases NO production. The liquid extract might therefore, through NO, prove to be helpful in some heart disease conditions as well as in pediatric patients with congenital heart disease complicated by pulmonary artery hypertension.

Moreover, liquid cartilage extract may help to decrease inflammation-associated complications in atherosclerosis.

Scleroderma: Scleroderma (Hard skin) is an uncommon disease marked by increases in fibrotic connective tissue of skin and often of visceral organs as well. It often appears as a hyperkeratinization of localized skin patches. Hyperkeratinization is a cellular process in which keratinocytes of the skin fully differentiate and accumulate rigid keratin fibers. This skin condition might lead to limited joint mobility if skin in a periarticuar area is affected. When added to an experimental system in which keratinocyte differentiation is encouraged, the liquid cartilage extract partially prevents the differentiation, or keratinization, process. Therefore, the liquid extract might be beneficial for such skin conditions by preventing overaccumulation of fully differentiated keratinocytes.

Veterinary applications: Solid and/or liquid cartilage extracts may be administred to animals for the same therapeutical and cosmetical applications that have been described for humans.

COSMETIC APPLICATIONS AND COMPOSITIONS:

The above tests and trials have shown that the cartilage extract of this invention may find numerous medical applications. Among the diverse activities recovered in this extract, anti-angiogenic, anti-collagenolytic, anti-inflammatory and the inhibitory effect on PKC-induced differentiation are particularly desirable in cosmetic applications. Since the cartilage extract of the present invention has shown an antagonist effect of PKC-mediated cellular events, and since such antagonist effect is suggested in the art as one improving the skin barrier function, a method for improving the barrier function in mammalian skin which comprises the step of applying to the skin a composition which comprises the cartilage extract and a pharmaceutically acceptable carrier, and such a composition are under the scope of this invention. Other or similar compositions can also be conceived to be used in a method for soothing skin or for reducing inflammation in mammalian skin. Inflammation can be caused by various agents such as chemical irritant, physical abrasion and exposure to ultraviolet radiation. Compositions and methods for inhibiting collagenase in skin are also contemplated. Collagenase and inflammation are linked to premature aging (degradation of collagen), and therefore the antagonist activities recovered in the cartilage extract could also be put to contribution in compositions and methods for retarding premature aging, and for regulating wrinkles or atrophy in mammalian skin. As causes of wrinkles or atrophy are listed, by way of examples, age, exposure to ultraviolet radiation or to environmental pollutant. Topical compositions may comprise an effective amount of shark cartilage, to be determined for each specific application. In general, these compositions may contain from about 0.1 to about 75 weight percent of a liquid cartilage extract and from about 25 to 99.9 weight percent of a pharmaceutically acceptable vehicle. These compositions may contain an anti-oxidant such as an agent which prevents the formation of lipid peroxides in skin. Examples of such anti-oxidant are tocopherol, tocopherol derivatives, ascorbic acid, ascorbic acid derivatives and BHT. The compositions can be complemented with anti-inflammatory agents like a phospholipase A2 inhibitor or the botanically-derived anti-irritants cola and green tea extract. Topical compositions may take diverse forms such as solutions, suspensions, lotions, tinctures, gels, creams, sprays, emulsions, sticks, ointments or liposomes (at least a portion of the liquid cartilage extract being present in liposomes). Other cosmetic applications include dark circle around the eyes and skin barrier function.

CONCLUSIONS

The process of the present invention has been demonstrated as one that provides for the production of cartilage extracts of a great clinical value. The shark cartilage extracts produced by this novel process comprises a multiplicity of activities that are recovered in good yields. The cartilage extracts, particularly the liquid extract and fractions thereof have a great potential since they are non-toxic to normal cells while they are effective in a large variety of diseases or conditions.

For all predicted applications (from ophthalmic drops to dermatological and cancer drug formulations), it is presumed that a minimal final protein concentration of the total liquid extract could be very low (from about 0.01 mg/ml). This lower range of doses depends on the accessibility and on the permeation of the active ingredients to the site of action as well as on the efficient capture of these ingredients and the sensitivity or response of the tissue to angiogenic inhibitors. The highest limit of the final protein concentration in formulations for some applications is not currently known. The highest final concentrations tried were a topical administration of about 9 mg/ml of proteins in the formulation for the psoriasis cases and an oral administration of about 12 mg/ml in the dose unit of 7 ml administered daily in the cancer cases and 21 ml in the arthritis trial.

The shark cartilage liquid extract may lose some of its activities when lyophilized. However, the addition of stabilizers or protective agents as known in the art prior to lyophilization may preserve sensitive activities and make possible the administration of higher doses of the cartilage extract in the dry state.

Required Material:

Coolers

Surgical instruments

Meat chopper

Plastic bags

Industrial blender (Waring 3-speed blender bought from Fisher Scientific)

A system of purification of water (inverse osmosis and 0.1 $\textcircled{E}$m filtration; Continental Water System, model PRE 2202, serial number 91089, Modulab Bioscience RQ/Polishing System bought from Fisher Scientific, Montreal, Quebec). This system provides an apyrogenic water of high quality.

A precision balance Mettler, series AE bought from Fisher Scientific

Centrifuge Sorvall RC-285 bought from DuPont Canada

Centrifuge CEPA

Nylon pocket of a porosity of 1 $\mu$M

An autoclave (automatic vapour sterilizer Sanyo, model MAC 350P)

Nalgene 500 ml containers sterilized at 132° C. for 10 minutes and dried for 35 minutes Conical filters of 24 $\mu$m porosity Whatman Reeve Angel Ultrafiltration column (Molecular weight cut-off: 500 kDa and 1 kDa when applicable; Surface: 25 square feet; Flow: 130 L/minute; Inlet pressure: 30 psi; Outlet pressure: 5 psi; bought from Koch Membrane Systems Inc., Wilmington, Mass., USA)

Sanitary centrifuge pump (Monarch Industries, model ACE-S100, type A) for providing a 130 L/minute flow sterile hut (laminar flow hut NuAire bought from Ingram & Bell)

Millipack-60 0.22 $\mu$m sterile filters

Sterile clear or amber glass bottles

Concentrator DC-10 Amicon

Rotofor Biorad 170–2950

Amicon filters SIOY10, SIOY30 and SIOY100 of cut-off values of 10, 30 and 100 kDa, respectively FPLC Pharmacia 216007 (computer Pharmacia 216014)

Hilstand S-300 26 mm/60 cm (Pharmacia)

Superose S-12 10 mm/30 cm (Pharmacia)

Lyophilizer Labconco 10273 A

This invention has been described hereinabove, and it should be appreciated that it would be well within the ability and the knowledge of the person skilled in the art, without departing from the teachings of this disclosure, to bring modifications by replacing some elements of this invention as practised by their equivalents, which would achieve the same goal thereof. These obvious variations are deemed covered by this application.

What is claimed is:

1. A method for improving mammalian skin barrier function which translates into more resistance to transepidermal water loss, said method comprising the step of applying to the skin a therapeutically effective amount of a shark cartilage extract obtained by a process comprising the steps of:

a) homogenizing shark cartilage in an aqueous solution in conditions which are substantially non-denaturing towards biologically active components extracted from cartilage, until the cartilage is reduced to solid particles whose size is lower than or equal to about 500 $\mu$m;

b) extracting said biologically active components into said aqueous solution, which results in a mixture of solid particles and of crude liquid extract having said biologically active components;

c) separating said crude liquid extract from said solid particles; and d) further separating the crude liquid extract so as to obtain a final liquid extract containing cartilage molecules having a molecular weight lower than about 500 Kilodaltons (KDa).

2. A method for soothing irritated mammalian skin, said method comprising the step of applying to the skin a therapeutically effective amount of a shark cartilage extract obtained by a process comprising the steps of:

a) homogenizing shark cartilage in an aqueous solution in conditions which are substantially non-denaturing towards biologically active components extracted from cartilage, until the cartilage is reduced to solid particles whose size is lower than or equal to about 500 $\mu$m;

b) extracting said biologically active components into said aqueous solution, which results in a mixture of solid particles and of crude liquid extract having said biologically active components;

c) separating said crude liquid extract from said solid particles;

d) further separating the crude liquid extract so as to obtain a final liquid extract containing cartilage molecules having a molecular weight lower than about 500 Kilodaltons (KDa); and e) filtering said final liquid extract on a membrane having a nominal molecular weight cut-off value of about 0.1 KDa, whereby said final liquid extract comprises molecules of a molecular weight lower than about 500 KDa and is enriched in molecules having a molecular weight of more than about 0.1 KDa.

3. A method for reducing inflammation in mammalian skin, said method comprising the step of applying to the skin a therapeutically effective amount of a shark cartilage extract obtained by a process comprising the steps of:

a) homogenizing shark cartilage in an aqueous solution in conditions which are substantially non-denaturing towards biologically active components extracted from cartilage, until the cartilage is reduced to solid particles whose size is lower than or equal to about 500 $\mu$m;

b) extracting said biologically active components into said aqueous solution, which results in a mixture of solid particles and of crude liquid extract having said biologically active components;

c) separating said crude liquid extract from said solid particles;

d) further separating the crude liquid extract so as to obtain a final liquid extract containing cartilage molecules having a molecular weight lower than about 500 kilodaltons (KDa); and e) filtering said final liquid extract on a membrane having a nominal molecular weight cut-off value of about 0.1 KDa, whereby said final liquid extract comprises molecules of a molecular weight lower than about 500 KDa and is enriched in molecules having a molecular weight of more than about 0.1 KDa.

4. A method as defined in claim 3 wherein said inflammation is caused by physical abrasion.

5. A method as defined in claim 3, wherein said inflammation is caused by chemical irritant.

6. A method as defined in claim 3 wherein said inflammation is caused by ultraviolet radiation.

7. A method for inhibiting collagenase activity in mammalian skin, said method comprising the step of applying to the skin a therapeutically effective amount of a shark cartilage extract obtained by a process comprising the steps of:

a) homogenizing shark cartilage in an aqueous solution in conditions which are substantially non-denaturing towards biologically active components extracted from cartilage, until the cartilage is reduced to solid particles whose size is lower than or equal to about 500 $\mu$m;

b) extracting said biologically active components into said aqueous solution, which results in a mixture of solid particles and of crude liquid extract having said biologically active components;

c) separating said crude liquid extract from said solid particles;

d) further separating the crude liquid extract so as to obtain a final liquid extract containing cartilage molecules having a molecular weight lower than about 500 Kilodaltons (KDa); and e) filtering said final liquid extract on a membrane having a nominal molecular weight cut-off value of about 0.1 KDa, whereby said final liquid extract comprises molecules of a molecular weight lower than about 500 KDa and is enriched in molecules having a molecular weight of more than about 0.1 KDa.

8. A method for regulating wrinkles or atrophy in mammalian skin, said method comprising the step of applying to the skin a therapeutically effective amount of a shark cartilage extract obtained by a process comprising the steps of:

a) homogenizing shark cartilage in an aqueous solution in conditions which are substantially non-denaturing towards biologically active components extracted from cartilage, until the cartilage is reduced to solid particles whose size is lower than or equal to about 500 $\mu$m;

b) extracting said biologically active components into said aqueous solution, which results in a mixtur eof solid particles and of crude liquid extract having said biological active components;

c) separating said crude liquid extract from said solid particles; and d) further separating the crude liquid extract so as to obtain a final liquid extract containing cartilage molecules having a molecular weight lower than about 500 Kilodaltons (KDa).

9. A method for reducing acne in mammalian skin, said method comprising the step of applying to the skin a therapeutically effective amount of a shark cartilage extract obtained by a process comprising the steps of:

a) homogenizing shark cartilage in an aqueous solution in conditions which are substantially non-denaturing towards biologically active components extracted from cartilage, until the cartilage is reduced to solid particles whose size is lower than or equal to about 500 $\mu$m;

b) extracting said biologically active components into said aqueous solution, which results in a mixture of solid particles and of crude liquid extract having said biologically active components;

c) separating said crude liquid extract from said solid particles;

d) further separating the crude liquid extract so as to obtain a final liquid extract containing cartilage molecules having a molecular weight lower than about 500 Kilodaltons (KDa); and e) filtering said final liquid extract on a membrane having a nominal molecular weight cut-off value of about 0.1

KDa, whereby said final liquid extract comprises molecules of a molecular weight lower than about 500 KDa and is enriched in molecules having a molecular weight of more than about 0.1 KDa.

10. A method for treating psoriasis in mammalian skin, said method comprising the step of applying to the skin a therapeutically effective amount of a shark cartilage extract obtained by a process comprising the steps of:
   a) homogenizing shark cartilage in an aqueous solution in conditions which are substantially non-denaturing towards biologically active components extracted from cartilage, until the cartilage is reduced to solid particles whose size is lower than or equal to about 500 μm;
   b) extracting said biologically active components into said aqueous solution, which results in a mixture of solid particles and of crude liquid extract having said biologically active components;
   c) separating said crude liquid extract from said solid particles;
   d) further separating the crude liquid extract so as to obtain a final liquid extract containing cartilage molecules having a molecular weight lower than bout 500 Kilodaltons (KDa); and
   e) filtering said final liquid extract on a membrane having a nominal molecular weight cut-off value of about 0.1 KDa, whereby said final liquid extract comprises molecules of a molecular weight lower than about 500 KDa and is enriched in molecules having a molecular weight of more than about 0.1 KDa.

11. A method for retarding premature aging in mammalian skin, said method comprising the step of applying to the skin a therapeutically effective amount of a shark cartilage extract obtained by a process comprising the steps of:
   a) homogenizing shark cartilage in an aqueous solution in conditions which are substantially non-denaturing towards biologically active components extracted from cartilage, until the cartilage is reduced to solid particles whose size is lower than or equal to about 500 μm;
   b) extracting said biologically active components into said aqueous solution, which results in a mixture of solid particles and of crude liquid extract having said biologically active components;
   c) separating said crude liquid extract from said solid particles; and
   d) further separating the crude liquid extract so as to obtain a final liquid extract containing cartilage molecules having a molecular weight lower than about 500 Kilodaltons (KDa).

12. A method of decreasing the expression of eczema in mammalian skin, said method comprising the step of applying to the skin a therapeutically effective amount of a shark cartilage extract obtained by a process comprising the steps of:
   a) homogenizing shark cartilage in an aqueous solution in conditions which are substantially non-denaturing towards biologically active components extracted from cartilage, until the cartilage is reduced to solid particles whose size is lower than or equal to about 500 μm;
   b) extracting said biologically active components into said aqueous solution, which results in a mixture of solid particles and of crude liquid extract having said biologically active components;
   c) separating said crude liquid extract from said solid particles; and
   d) further separating the crude liquid extract so as to obtain a final liquid extract containing cartilage molecules having a molecular weight lower than about 500 Kilodaltons (KDa).

* * * * *

UNITED STATES PATENT AND TRADEMARK OFFICE
CERTIFICATE OF CORRECTION

| | | |
|---|---|---|
| PATENT NO. | : 6,028,118 | Page 1 of 1 |
| APPLICATION NO. | : 08/693535 | |
| DATED | : February 22, 2000 | |
| INVENTOR(S) | : Eric Dupont et al. | |

It is certified that error appears in the above-identified patent and that said Letters Patent is hereby corrected as shown below:

On the title page of the patent, insert item (60):

-- Related U.S. Application Data

Continuation-in-part of application No. 08/550,003, October 30, 1995, now U.S. Pat. No. 6,025,334, which is a continuation-in-part of application No. 08/384,555, February 3, 1995, now U.S. Pat. No. 5,618,925, which is a continuation-in-part of application No. 08/234,019, April 28, 1994, now abandoned. --

The specification, at page 1, before the first line, insert:

--CROSS REFERENCE TO EARLIER FILED APPLICATIONS

This application is a continuation-in-part of application Serial No. 08/550,003, filed October 30, 1995, now U.S. Pat. No. 6,025,334 issued February 15, 2000, which is a continuation-in-part of application Serial No. 08/384,555, filed February 3, 1995, now U.S. Pat. No. 5,618,925 issued April 8, 1997, which is a continuation-in-part of application Serial No. 08/234,019 filed April 28, 1994, now abandoned. --

Signed and Sealed this

Fourth Day of September, 2007

JON W. DUDAS
*Director of the United States Patent and Trademark Office*